(12) United States Patent
Ebbini et al.

(10) Patent No.: US 10,231,712 B2
(45) Date of Patent: Mar. 19, 2019

(54) DUAL MODE ULTRASOUND TRANSDUCER (DMUT) SYSTEM AND METHOD FOR CONTROLLING DELIVERY OF ULTRASOUND THERAPY

(75) Inventors: Emad S. Ebbini, Edina, MN (US); Andrew J. Casper, Eau Claire, WI (US); Dalong Liu, Saint Paul, MN (US); John R. Ballard, Saint Bonifacius, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 752 days.

(21) Appl. No.: 13/702,813

(22) PCT Filed: Jun. 9, 2011

(86) PCT No.: PCT/US2011/039837
§ 371 (c)(1),
(2), (4) Date: Feb. 19, 2013

(87) PCT Pub. No.: WO2011/156624
PCT Pub. Date: Dec. 15, 2011

(65) Prior Publication Data
US 2013/0144165 A1 Jun. 6, 2013

Related U.S. Application Data

(60) Provisional application No. 61/353,096, filed on Jun. 9, 2010, provisional application No. 61/475,550, filed on Apr. 14, 2011.

(51) Int. Cl.
*A61B 8/00* (2006.01)
*A61B 8/08* (2006.01)
(Continued)

(52) U.S. Cl.
CPC ............ *A61B 8/54* (2013.01); *A61B 8/4488* (2013.01); *A61B 8/5223* (2013.01); *A61N 7/02* (2013.01);
(Continued)

(58) Field of Classification Search
CPC .......... A61B 8/00; A61B 8/54; A61B 8/5223; A61B 8/4488; A61B 8/485; A61B 8/0816;
(Continued)

(56) References Cited

U.S. PATENT DOCUMENTS 5,694,936 A * 12/1997 Fujimoto ................ A61N 7/02
600/439
5,906,580 A * 5/1999 Kline-Schoder et al. .... 600/459
(Continued)

FOREIGN PATENT DOCUMENTS

WO  WO 2006018761 A1 * 2/2006 ............. A61N 5/103
WO  2006/042201 A1  4/2006
(Continued)

OTHER PUBLICATIONS

U.S. Appl. No. 61/353,096, filed Jun. 9, 2010, Ebbini et al.
(Continued)

*Primary Examiner* — Sanjay Cattungal
(74) *Attorney, Agent, or Firm* — Mueting Raasch & Gebhardt, PA

(57) ABSTRACT

A dual-mode ultrasound system provides real-time imaging and therapy delivery using the same transducer elements of a transducer array. The system may use a multi-channel driver to drive the elements of the array. The system uses a real-time monitoring and feedback image control of the therapy based on imaging data acquired using the dual-mode ultrasound array (DMUA) of transducer elements. Further, for example, multi-modal coded excitation may be used in
(Continued)

both imaging and therapy modes. Still further, for example, adaptive, real-time refocusing for improved imaging and therapy can be achieved using, for example, array directivity vectors obtained from DMUA pulse-echo data.

47 Claims, 45 Drawing Sheets

(51) Int. Cl.
A61N 7/02 (2006.01)
A61N 7/00 (2006.01)
(52) U.S. Cl.
CPC .............. A61B 8/0816 (2013.01); A61B 8/485 (2013.01); A61N 2007/0052 (2013.01); A61N 2007/0095 (2013.01); A61N 2007/027 (2013.01)
(58) Field of Classification Search
CPC ................ A61N 7/02; A61N 2007/027; A61N 2007/0095; A61N 2007/0052
See application file for complete search history.

(56) References Cited

U.S. PATENT DOCUMENTS

| | | | |
|---|---|---|---|
| 6,770,031 B2 | 8/2004 | Hynynen et al. | |
| 6,951,540 B2 | 10/2005 | Ebbini et al. | |
| 7,063,666 B2 | 6/2006 | Weng et al. | |
| 2003/0220636 A1* | 11/2003 | Bowman et al. | ............... 606/28 |
| 2003/0225331 A1* | 12/2003 | Diederich et al. | ............ 600/437 |
| 2004/0015079 A1* | 1/2004 | Berger | ................ G01S 7/52025 600/437 |
| 2004/0106880 A1* | 6/2004 | Weng | .................... A61B 8/4422 601/2 |
| 2004/0210135 A1* | 10/2004 | Hynynen et al. | ............. 600/439 |
| 2005/0102009 A1* | 5/2005 | Costantino | .............. A61B 8/463 607/96 |
| 2005/0249667 A1* | 11/2005 | Tuszynski | ................ A61N 7/00 424/9.3 |
| 2005/0267453 A1 | 12/2005 | Wong et al. | |
| 2007/0055155 A1* | 3/2007 | Owen et al. | ................... 600/439 |
| 2007/0129633 A1 | 6/2007 | Lee et al. | |
| 2008/0027320 A1* | 1/2008 | Bolorforosh | ............. A61B 8/12 600/439 |
| 2008/0221448 A1 | 9/2008 | Khuri-Yakub et al. | |
| 2008/0228075 A1* | 9/2008 | Fraser | ................... A61B 8/0833 600/443 |
| 2009/0048546 A1 | 2/2009 | Appelman et al. | |
| 2009/0069680 A1* | 3/2009 | Abe | ......................... A61B 8/08 600/440 |
| 2010/0286520 A1* | 11/2010 | Hazard et al. | ................ 600/439 |
| 2011/0112405 A1* | 5/2011 | Barthe | ................. A45D 44/005 600/459 |
| 2011/0248714 A1* | 10/2011 | Salomir et al. | ............... 324/309 |
| 2012/0083692 A1 | 4/2012 | Stoll | |
| 2012/0283564 A1 | 11/2012 | Ebbini et al. | |

FOREIGN PATENT DOCUMENTS

| | | | | |
|---|---|---|---|---|
| WO | | 2008/053457 A2 | 5/2008 | |
| WO | | 2009/002492 A1 | 12/2008 | |
| WO | WO | 2009050719 A2 * | 4/2009 | .............. A61N 7/02 |
| WO | | 2011/156624 A2 | 12/2011 | |
| WO | | 2012/033584 A2 | 3/2012 | |
| WO | | 2012/142455 A2 | 10/2012 | |

OTHER PUBLICATIONS

U.S. Appl. No. 61/475,550, filed Apr. 14, 2011, Ebbini et al.
Ainsworth et al. "3D ultrasound measurement of change in carotid plaque—A tool for rapid evaluation of new therapies," 2005. *Stroke.* 36(9):1904-1909.
Amini et al., "Noninvasive Estimation of Tissue Temperature via High-Resolution Spectral Analysis Techniques," *IEEE Transactions on Biomedical Engineering*, Feb. 2005; 52(2):221-228.
Arthur et al., "In vivo change in ultrasonic backscattered energy with temperature in motion-compensated images," *International Journal of Hyperthermia*, 2008; 24(5):389-398.
Aubry et al., "Transcostal high-intensity-focuses ultrasound: Ex vivo adaptive focusing feasibility study," *Phys. Med. Biol.*, 2008; 53:2937-2951.
Ballard et al., "Monitoring and Guidance of HIFU Beams with Dual-Mode Ultrasound Arrays," $31^{st}$ *Annual International Conference of the IEEE EMBS*, Minneapolis, MN; Sep. 2-6, 2009:137-140.
Ballard et al. "Adaptive Transthoracic Refocusing of Dual-Mode Ultrasound Arrays," 2010. *IEEE Transactions on Biomedical Engineering.* 57(1):93-102.
Bischof et al. "Rectal Protection During Prostate Cryosurgery: Design and Characterization of an Insulating Probe," *Cryobiology* 1997; 34:80-92.
Blake et al. "A Method to estimate wall shear rate with a clinical ultrasound scanner," 2008. *Ultrasound in Medicine and Biology.* 34(5):760-774.
Blana et al., "First analysis of the long-term results with transrectal HIFU in patients with localized prostate cancer," *Euro Urology*, Jun. 2008; 53(6):1194-1203.
Bohn et al., "An analysis package comparing pid antiwindup strategies," *Control Systems Magazine*, IEEE, Apr. 1995; 15(2):34-40.
Botros et al., "Two-step hybrid virtual array-ray (VAR) technique for focusing through the rib cage," *IEEE Trans. Ultrason. Ferroelectr., Freq. Control*, Jul. 1998; 45(4): 989-1000.
Bracewell et al. "Two-dimensional Imaging". Printice-Hall Signal Processing Series. 1995. Cover page, Title Page, Copyright Page, and Table of Contents. 11 pages total.
Casper et al., "Realtime Control of Multiple-focus Phased Array Heating Patterns Based on Noninvasive Ultrasound Thermography," *IEEE Trans. Biomed. Eng.*, Jan. 2012; 59(1):95-105.
Cespedes et al. "Echo decorrelation from displacement gradients in elasticity and velocity estimation" 1999. *IEEE Trans. UFFC.* 46:791-801.
Chan et al., "An image-guided high intensity focused ultrasound device for uterine fibroids treatment," *Med. Phys.*, 2002; 29:2611-2620.
Chapelon et al., "New piezoelectric transducers for therapeutic ultrasound," *Ultrasound Med. Biol.*, Jan. 2000; 26(1):153-159.
Chew et al. "Waves and Fields in Inhomogeneous Media". 1990. Van Nostrand Reinhold, New York, NY. Cover Page, Title Page, Copyright Page, and Table of Contents. 12 pages total.
Curiel et al., "1.5-D high intensity focused ultrasound array for non-invasive prostate cancer surgery," *IEEE Trans. Ultrason., Ferroelectr., Freq. Control*, Feb. 2002; 49(2):231-242.
Dalong et al., "Viscoelastic property measurement in thin tissue constructs using ultrasound," *IEEE Trans. Ultrason. Ferroelecdt. Freq. Contr.*, 2008; 55(2):368-383.
Ebbini et al., "A cylindrical-section ultrasound phased-array applicator for hyperthermia cancer therapy," *IEEE Trans. Ultrasonics, Ferroelectrics, and Frequency Control*, 1988; 35(5): 561-572.
Ebbini et al., "Multiple-focus ultrasound phased array pattern synthesis—Optimal driving signal distributions for hyperthermia," *IEEE Transactions on Ultrasonics Ferroelectrics and Frequency Control*, Sep. 1989; 36(5): 540-548.
Ebbini, "Deep-localized hyperthermia with ultrasound phased arrays using the pseudoinverse pattern synthesis methods," Ph.D. Dissertation, University of Illinois, Urbana, IL; 1990.
Ebbini et al., "Experimental evaluation of a prototype cylindrical section ultrasound hyperthermia phased-array applicator," *IEEE Transactions on Ultrasonics Ferroelectrics and Frequency Control*, Sep. 1991; 38(5):510-520.
Ebbini et al., "Optimization of the intensity gain of multiple-focus phased-array heating patterns," *Int. J. Hyperthermia*, 1991; 7(6): 953-973.
Ebbini et al., "A spherical-section ultrasound phased array applicator for deep localized hyperthermia," *IEEE Trans. Biomedical Engineering*, 1991; 38(7):634-643.

(56) References Cited

OTHER PUBLICATIONS

Ebbini et al., "Optimal transversal filter bank for 3D real-time acoustical imaging," *Proc. 26th Annual Asilomar Conference on Signals, Systems and Computers*, 1992; 2:831-835.
Ebbini et al., "Lesion formation and visualization using dual-mode ultrasound phased arrays," *Proc. IEEE Ultrason. Symp.*, Oct. 2001; 2:1351-1354.
Ebbini, "Phase-coupled two-dimensional speckle tracking algorithm," *IEEE Trans. Ultrason. Ferroelect. Freq. Contr.*, 2006; 53(5):972-990.
Ebbini et al. "Dual-Mode Ultrasound Phased Arrays for Image-Guided Surgery," *Ultrason Imaging*; Apr. 2006; 28(2):65-82.
Ebbini et al., "Monitoring and Guidance of Minimally-Invasive Thermal Therapy Using Diagnostic Ultrasound," *31st Annual International Conference of the IEEE EMBS*, Minneapolis, MN; Sep. 2-6, 2009:4283-4286.
Ebbini, "Guest Editorial to the Special Issue on Therapeutic Ultrasound: Current Status and Future Directions," *IEEE Transactions on Biomedical Engineering*, Jan. 2010; 57(1):57-60.
Ebbini, "Guest Editorial to the Special Issue on Therapeutic Ultrasound: Trends at the Leading-Edge," *IEEE Transactions on Biomedical Engineering*, Jan. 2010; 57(1):5-6.
Ebbini et al., "Dereverberation of Ultrasound Echo Data in Vascular Imaging Applications," IEEE International Conference on Acoustics, Speech and Signal Processing (ICASSP), May 22-27, 2011:741-744.
Figueroa et al. "A computational framework for fluid-solid-growth modeling in cardiovascular simulations," 2009. *Computer Methods in Applied Mechanics and Engineering.* 198(45-46):3583-3602.
Fink, "Time reversal of ultrasonic fields. I. Basic principles," *IEEE Trans. Ultrason., Ferroelectr., Freq. Control*, Sep. 1992; 39(5):555-566.
Fleury et al., "New piezocomposite transducers capable of producing high-power levels suitable for therapy with reasonably wide bandwidth suitable for imaging," *Proc. 2nd Int. Symp. Ther. Ultrasound*, 2002; 1:428-436.
Fung et al. Biomechanics: Circulation, 2nd Ed. Springer, New York. 1997. Cover Page, Copyright Page, Table of Contents.
Goel et al., "Adjuvant Approaches to Enhance Cryosurgery," *Journal of Biomechanical Engineering*, 2009; 131(7):074003.
Gronningsaeter et al., "Vessel wall detection and blood noise reduction in intravascular ultrasound imaging," *IEEE Transactions on Ultrasonics, Ferroelectrics and Frequency Control*, IEEE, US, May 1, 1996; 43(3): pp. 359-369.
Haddadin et al. "Imaging strongly scattering media using a multiple frequency distorted Born iterative method". 1998. *IEEE Transactions of Ultrasonics Ferroelectrics and Frequency Control.* 45(6):1485-1496.
Haken et al., "Effect of mode conversion on ultrasonic heating oat tissue interfaces," *J. Ultrasound Med.*, 1992; 11:393-405.
Hermus et al. "Advanced carotid plaque imaging". 2010. *European Journ. of Vascular and Endovascular Surgery.* 39(2):125-133.
Hindley et al., "MRI guidance of focused ultrasound therapy of uterine fibroids: Early results," *Am. J. Roentgenology*, Dec. 2004; 183(6):1713-1719.
Hynynen et al., "Trans-skull ultrasound therapy: the feasibility of using image-derived skull thickness information to correct the phase distortion," *IEEE Trans. Ultrason, Ferroelectr., Freq. Control*, May 1999; 46(5): 752-755.
Ibbini et al., "N X N square-element ultrasound phased array applicator: Simulated temperature distributions associated with directly synthesized heating patterns," *IEEE Trans. Ultrason, Ferroelectr., Freq. Control*, 1990; 37(6):491-500.
Insana et al. "Maximum-likelihood approach to strain imaging using ultrasound". 2000. *J. Acoust. Soc. Am.* 107(3):1421-1434.
International Preliminary Report on Patentability and Written Opinion dated Dec. 10, 2012, for International Application No. PCT/US2011/039837, filed Jun. 9, 2011; 6 pgs.
International Preliminary Report on Patentability and Written Opinion dated Oct. 15, 2013, for International Application No. PCT/US2012/033584, filed Apr. 13, 2012; 12 pgs.
International Search Report dated Jan. 20, 2012, for International Application No. PCT/US2011/039837, filed Jun. 9, 2011; 4 pgs.
International Search Report dated Jun. 13, 2013, for Patent Application No. PCT/US2012/033584, filed Apr. 13, 2012; 6 pgs.
Ishida et al., "Development and animal experiment of variable focusing HIFU system for prostate cancer treatment," *3rd Int. Symp. THer. Ultrasound*, 2003; 1:382-387.
Karimi et al. "Estimation of Nonlinear Mechanical Properties of Vascular Tissues via Elastography," 2008. *Cardiovascular Engineering.* 8(4):191-202.
Kim et al. "Arterial vulnerable plaque characterization using ultrasound-induced thermal strain imaging (TSI)," 2008. *IEEE Transaction on Biomedical engineering.* 55(1):171-180.
Lee et al., "High Intensity Focused Ultrasound Effect on Cardiac Tissues: Potential for Clinical Application," *Echocardiography*, 2000; 17(6):563-566.
Li et al., "A new filter design technique for coded excitation systems," *IEEE Trans. Ultrasonics, Ferroelectrics, and Frequency Control*, 1992; 39(6):693-699.
Li et al., "Blocked Element Compensations in Phased Array Imaging," *IEEE Trans. Ultrasonics, Ferroelectrics, and Frequency Control*, 1993; 40(4):283-292.
Liu et al. "Real-Time 2-D Temperature Imaging Using Ultrasound," *IEEE Transactions on Biomedical Engineering.* Jan. 2010; 57(1):12-16.
Liu et al. "Viscoelastic property measurement in thin tissue constructs using ultrasound". 2008. *IEEE Trans. Ultrason. Ferroelect. Freq. Contr.* 55(2):368-383.
Lubinski et al. "Speckle tracking methods for ultrasonic elasticity imaging using short-time correlation". 1999. *IEEE Trans. UFFC.* 46:82-96.
Mahmoud et al. "In vivo vascular wall tissue characterization using a strain tensor measuring (STM) technique for flow-mediated vasodilation analyses". 2009. *Physics in Medicine and Biology.* 54(20):6217-6238.
Martin et al., "Investigation of HIFU produced emulsion for acoustic hemostasis," *Proc. 3rd Int. Symp. Ther. Ultrasound*, 2003; 1:351-356.
Maass-Moreno et al., "Noninvasive temperature estimation in tissue via ultrasound echo shifts. Part I. Theoretical model," *The Journal of the Acoustical Society of America*, 1996; 100(2514-2521).
McGough et al., "Direct Computation of ultrasound phased-array driving signals from specified temperature distribution for hyperthermia," *IEEE Trans. Biomedical Engineering*, 1992; 39(8):825-835.
McGough et al., "Mode scanning: heating pattern synthesis with ultrasound phased arrays," *Int. Journal of Hyperthermia*, 1994; 10(3):433-442.
Miller et al., "Fundamental limitations of noninvasive temperature imaging by means of ultrasound echo strain estimation," *Ultrasound in Medicine and Biology*, 2002; 28:1319-1333.
Mougenot et al., "Automatic spatial and temporal temperature control for MR-guided focused ultrasound using fast 3D MR thermometry and multispiral trajectory of the focal point," *Magnetic Resonance in Medicine*, Nov. 2004; 52(5):1005-1015.
Mougenot et al., "Three-dimensional spatial and temporal temperature control with MR thermometry-guided focused ultrasound (mrghifu)," *Magnetic Resonance in Medicine*, 2009; 61:603-614.
Moyle et al. "Inlet conditions for image-based CFD models of the Carotid bifurcation: Is it reasonable to assume fully developed flow?" 2006. *Journ. of Biomechanical Engr. Transactions of the ASME.* 128(3):371-379.
Nightingale et al., "On the feasibility of remote palpation using acoustic radiation force," *J. Acoust. Soc. Amer.*, Jul. 2001; 110:625-634.
Pesavento et al. "A time efficient and accurate strain estimation concept for ultrasonic elastography using iterative phase zero estimation". 1999. *IEEE Trans. UFFC.* 46(5):1057-1067.

(56) References Cited

OTHER PUBLICATIONS

Perrot et al., "High power density prototype for high precision transcranial therapy," *Proc. 3rd Int. Symp. Ther. Ultrasound*, 2003; 1:405-410.
Perrot et al., "Temperature estimation using ultrasonic spatial compounding," *IEEE Trans. Ultrason., Ferroelect., Freq. Contr.*, 2004; 51(5):606-615.
Poissonnier et al., "Control of prostate cancer by transrectal HIFU in 227 patients," *Eur. Urol.*, 2007; 51:381-387.
Prada et al., "The iterative time reversal process: Analysis of the convergence," *J. Acoust. Soc. Amer.*, 1995; 95:62-71.
Pramanik et al., "Thermoacoustic and photoacoustic sensing of temperature," *Journal of Biomedical Optics*, 2009; 14(5).
Rabben et al. "Ultrasound-based vessel wall tracking: an autocorrelation technique with RF center frequency estimation". 2002. *Ultrasound in Medicine and Biology.* 28(4):507-517.
Rabben et al. "An ultrasound-based method for determining pulse wave velocity in superficial arteries". 2004. *Journ. of Biomechanics.* 37(10):1615-1622.
Raghupathy et al. "Generalized Anisotropic Inverse Mechanics for Soft Tissues". 2010. *J. Biomech. Eng.* 132. Accepted 2010.
Revell et al., "Ultrasound Speckle Trackign for Strain Estimation," University of Bristol Department of Computer Science; Dec. 2003: 4pgs.
Ribbers et al. "Noninvasive two-dimensional strain imaging of arteries: Validation in phantoms and preliminary experience in carotid arteries in vivo". 2007. *Ultrasound in Medicine and Biology.* 33(4):530-540.
Salomir et al., "Hyperthermia by MR-guided focuses ultrasound: Accurate temperature control based on fast MRI and a physical model of local energy deposition and heat conduction," *Magnetic Resonance in Medicine*, 2000; 43:342-347.
Sanghvi et al., "Noninvasive surgery of prostate tissue by high-intensity focused ultrasound," *IEEE Trans. Ultrason., Ferroelectr., Freq. Contr.*, Nov. 1996; 43(6):1099-1110.
Sanghvi et al., "New developments in therapeutic ultrasound," *IEEE Eng. Med. Biol. Mag.*, Nov./Dec. 1996; 15(6):83-92.
Sapareto et al., "Thermal dose determination in cancer therapy," *Int. J. Rad. Onc. Biol. Phys.*, 1984; 10(6):787-800.
Schoenhagen et al. "Coronary imaging: Angiography shows the stenosis, but IVUS, CT, and MRI show the plaque". 2003. *Cleveland Clinic Journ. of Medicine.* 70(8):713-719.
Seip et al., "Characterization of a Needle Hydrophone Array for Acoustic Feedback during Ultrasound Hyperthermia Treatments," *Ultrasonics Symposium Proceedings*, 1992; 2:1265-1269.
Seip et al., "Non-Invasive Detection of Thermal Effects due to Highly Focused Ultrasonic Fields," *Ultrasonics Symposium Proceedings*, 1993; 2:1229-1232.
Seip et al., "Dynamic focusing in ultrasound hyperthermia treatments using implantable hydrophone arrays," *IEEE Trans. Ultrason., Ferroelectr., Freq. Control*, Sep. 1994; 41(5):706-713.
Seip et al., "Invasive and Non-Invasive Feedback for Ultrasound Phased Array Thermotherapy," *Ultrasonics Symposium Proceedings*, 1994; 3:1821-1824.
Seip et al., "Non-invasive Spatio-temporal Temperature Change Estimation Using Diagnostic Ultrasound," *Ultrasonics Symposium Proceedings*, 1995.
Seip et al., "Non-invasive estimation of tissue temperature response to heating fields using diagnostic ultrasound," *IEEE Trans. Biomed. Eng.*, 1995; 42(8):828-839.
Seip et al., "Noninvasive real-time multipoint temperature control for ultrasound phased array treatments," *IEEE Transactions on Ultrasonics Ferroelectrics and Frequency Control*, Nov. 1996; 43(6):1063-1073.
Seip et al., "High-intensity focused ultrasound (HIFU) phased arrays: Recent developments in transrectal transducers and driving electronics," *Proc. 3rd Int. Symp. Ther. Ultrasound*, 2003; 1:423-428.

Shen et al., "An Optimal Image Operator Design Technique for Coded-Excitation Ultrasound Imaging System," *IEEE Ultrasonics Symposium Proceedings*, 1994.
Shen et al., "Post-Beamforming Processing Technique for Enhancing Conventional Pulse-Echo Ultrasound Imaging Contrast Resolution," *IEEE Ultrasonics Symposium Proceedings*, 1995.
Shen et al. "A New Coded-Excitation Ultrasound Imaging System—Part I: Basic Principles," *IEEE Transactions on Ultrasonics, Ferroelectrics, and Frequency Control.* Jan. 1996; 43(1):131-140.
Shen et al. "A New Coded-Excitation Ultrasound Imaging System—Part II: Operator Design," *IEEE Transactions on Ultrasonics, Ferroelectrics, and Frequency Control.*, Jan. 1996; 43(1):141-148.
Shen et al. "Filter-Based Coded-Excitation System for High-Speed Ultrasonic Imaging," *IEEE Transactions on Medical Imaging*, Dec. 1998; 17(6):923-934.
Shung et al. "Scattering of ultrasound by blood". 1976. *IEEE Transactions on Biomedical Engineering*, vol. BME-23. 6:460-467.
Simon et al., "Estimation of Mean Scatterer Spacing Based on Autoregressive Spectral Analysis of Prefiltered Echo Data," *Ultrasonics Symposium Proceedings*, 1995.
Simon et al. "Two-Dimensional Temperature Estimation Using Diagnostic Ultrasound," *IEEE Transactions on Ultrasonics, Ferroelectrics, and Frequency Control.* Jul. 1998; 45(4):1088-1099.
Simon et al., "Combined ultrasound image guidance and therapy using a therapeutic phased array," *SPIE Med. Imag.*, May 1998; 3341:89-98.
Smith et al., "Control system for an MRI compatible intracavitary ultrasound array for thermal treatment of prostate disease," *International Journal of Hyperthermia*, May-Jun. 2001; 17(3):271-282.
Souchon et al., "Monitoring the formation of thermal lesions with heat-induces echo-strain imaging: a feasibility study," *Ultrasound in Medicine and Biology*, 2005; 31:251-259.
Steidl et al., "Dual-mode ultrasound phased arrays for noninvasive surgery: Post-beamforming image compounding algorithms for enhanced visualization of thermal lesions," *Proc. IEEE Int. Symp. Biomed. Imag.*, Jul. 2002; 429-432.
Steinman et al. "Flow imaging and computing: Large artery hemodynamics," 2005. *Annals of Biomedical Engineering.* 33(12):1704-1709.
Sumi, C. "Fine elasticity imaging utilizing the iterative rf-echo phase matching method". 1999. *IEEE Trans. UFFC*, 46(1):158-166.
Sun et al., "Focusing of therapeutic ultrasound through a human skull: A numerical study," *J. Acoust. Soc. Amer.*, 1998; 104:1705-1715.
Sun et al., "Adaptive real-time closed-loop temperature control for ultrasound hyperthermia using magnetic resonance thermometry," *Concepts in Magnetic Resonance Part B—Magnetic Resonance Engineering*, Oct. 2005; 27B(1):51-63.
Swillens et al. "Two dimensional flow imaging in the carotid bifurcation using a combined speckle tracking and phase-shift estimator: a study based on ultrasound simulations and in vivo analysis". 2010. *Ultrasound in Medicine and Biology.* 36(10):1722-1735.
Swillens et al. "Two-dimensional blood velocity estimation with ultrasound: speckle tracking versus crossed-beam vector Doppler based on flow simulations in a carotid bifurcation model". 2010. *IEEE Transactions on Ultrasonics Ferroelectrics and Frequency Control.* 57(2):327-339.
Tanter et al., "Focusing and steering through absorbing and aberrating layers: Application to ultrasonic propagation through the skull," *J. Acoust. SOc. Amer.*, 1998; 103:2403-2410.
Taylor et al. "Open problems in computational vascular biomechanics: Hemodynamics and arterial wall mechanics," 2009. *Computer Methods in Applied Mechanics and Engineering.* 198(45-46):3514-3523.
Tempany et al., "MR imaging-guided focuses ultrasound surgery of uterine leiomyomas: A feasibility study," *Radiology*, Nov. 2003;226:897-905.
Thomenius et al., "Evolution of ultrasound beamformers," *Proc. IEEE Ultrason. Symp.*, 1996; 1615-1622.

(56) References Cited

OTHER PUBLICATIONS

Trahey et al., "Angle independent ultrasonic blood flow detection by frame-to-frame correlation of B-mode images," *Ultrasonics*, IPC Science and Technology Press Ltd., Guildford, GB, Sep. 1, 1988; 26(5): pp. 271-276.

Tsou et al. "Role of ultrasonic shear rate estimation errors in assessing inflammatory response and vascular risk," 2008. *Ultrasound in Medicine and Biology*. 34(6):963-972.

Uchida et al., "Transrectal high-intensity focused ultrasound for the treatment of localized prostate cancer: Eightyear experience," *Int. J. Urology*, Nov. 2009; 16(11):881-886.

VanBaren et al., "A new algorithm for dynamic focusing of phased-array hyperthermia applicators through tissue inhomogeneities," *IEEE Ultrasonics Symposium Proceedings*, 1993; 2:1221-1224.

VanBaren et al., "Real-time Dynamic Focusing through Tissue Inhomogeneities during Hyperthermia Treatments with Phased Arrays," *Ultrasonics Symposium Proceedings*, 1994; 3:1815-1819.

VanBaren et al., "2D Large Aperture Ultrasound Phased Arrays for Hyperthermia Cancer Therapy: Design, Fabrication, and Experimental Results," *Ultrasonics Symposium Proceedings*, 1995.

VanBaren et al., "Multi-Point Temperature Control During Hyperthermia Treatments: Theory and Simulation," *IEEE Transactions on Biomedical Engineering*, Aug. 1995; 41(5):706-713.

Vanne et al., "MRI feedback temperature control for focused ultrasound surgery," *Physics in Medicine and Biology*, 2003; 48(1): 31.

Varghese et al. "Direct strain estimation in elastography using spectral cross-correlation". 2000. *Ultrasound in Med. Biol.* 26(9):1525-1537.

Wan et al., "Ultrasound surgery: Comparison of strategies using phased array systems," *IEEE Trans. UFFC*, Nov. 1996; 43(6):1085-1098.

Wan et al. "Imaging with Concave Large-Aperture Therapeutic Ultrasound Arrays Using Conventional Synthetic-Aperture Beamforming," *IEEE Transactions on Ultrasound, Ferroelectrics, and Frequency Control.*, Aug. 2008; 55(8):1705-1718.

Wan et al. "Imaging vascular mechanics using ultrasound: Phantom and in vivo results," *IEEE Int. Symp. on Biomed. Imag.* 2010; 980-983.

Wang et al., "Effects of phase quantization errors on field patterns generated by an ultrasound phased array hyperthermia applicator," *IEEE Trans. Ultrasonics Ferroelec. Frequency Control*, 1991; 38(5): 521-531.

Wang et al., "Adaptive 2-D Cylindrical Section Phased Array System for Ultrasonic Hyperthermia," *Ultrasonics Symposium Proceedings*, 1992; 2:1261-1264.

Wang et al., "Phase aberration correction and motion compensation for ultrasonic hyperthermia phased arrays: Experimental results," *IEEE Trans. on Ultrason., Ferroelec., and Freq. Control*, 1994; 41(1):34-43.

Weitzel et al. "High-Resolution Ultrasound Elasticity Imaging to Evaluate Dialysis Fistula Stenosis," 2009. *Seminars in Dialysis*. 22(1):84-89.

Written Opinion/International Preliminary Report on Patentability, dated Jul. 15, 2009, Patent Application No. PCT/US2008/007842, filed Jun. 24, 2008; 25 pgs.

Wu et al., "Time reversal of ultrasonic fields. II. Experimental results," *IEEE Trans. Ultrason., Ferroelectr., Freq. Control*, Sep. 1992; 39(5):567-578.

Wu et al., "Advanced hepatocellular carcinoma: Treatment with high-intensity focused ultrasound ablation combined with transcatheter arterial embolization," *Radiology*, May 2005; 235(2):659-667.

Wu et al., "Feasibility of US-guided high-intensity focused ultrasound treatment in patients with advanced pancreatic cancer: Initial experience," *Radiology*, Sep. 2005; 236(3):1034-1040.

Yao et al., "Enhanced lesion visualization in image-guided noninvasive surgery with ultrasound phased arrays," *Proc. 23rd Annu. Int. Conf IEEE Eng, Med. Biol. Soc.*, Oct. 2001; 3:2492-2495.

Yao et al., "Real-time monitoring of the transients of HIFU-induced lesions," *Proc. IEEE Ultrason. Symp.*, Oct. 2003; 1:1006-1009.

Yao et al., "Dual-mode ultrasound phased arrays for imaging and therapy," *Proc. IEEE Int. Symp. Biomed. Imag.*, Apr. 2004; 1:25-28.

Yuh et al., "Delivery of systemic chemotherapeutic agent to tumors by using focused ultrasound: Study in a murine model," *Radiology*, Feb. 2005; 234(2):431-437.

Gelet, "845 Prostate cancer control with transrectal HIFU in 242 consecutive patients: 5-year results" Jan. 2004 *European Urology Supplements* 3(2):214-214.

* cited by examiner

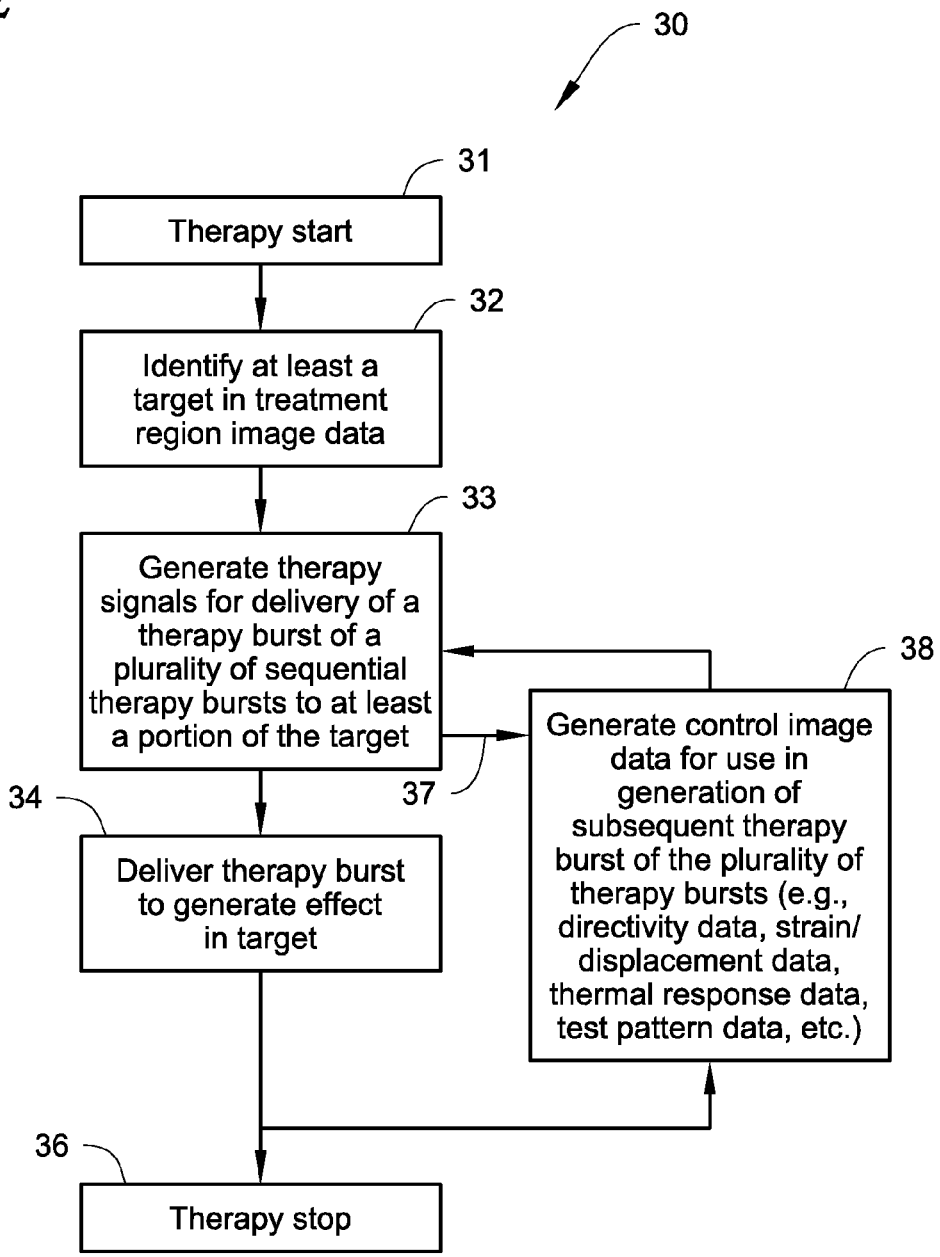

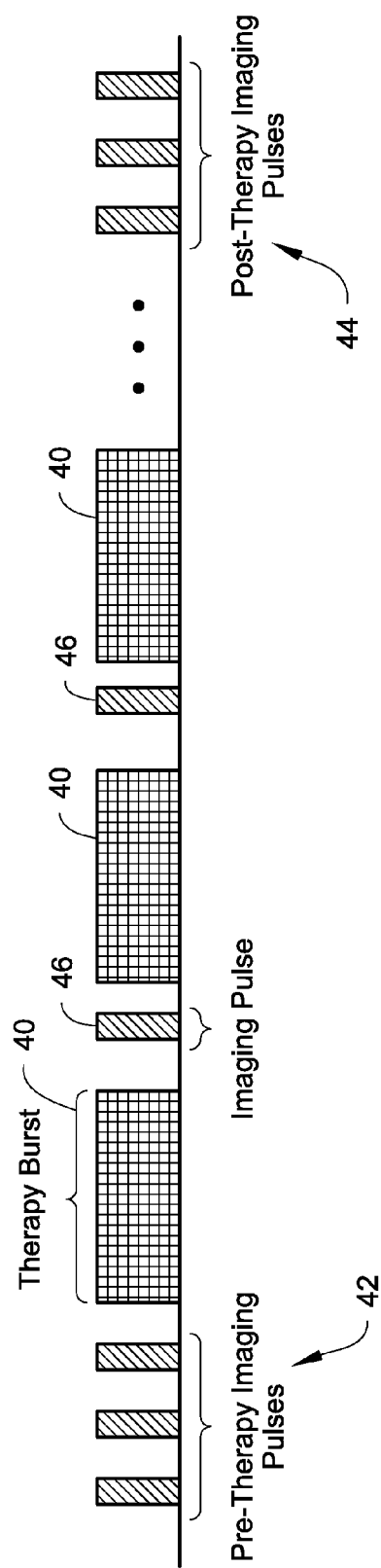

Algorithm 1 Image-based Refocusing Procedures
---
1: procedure SOLVE OPTIMIZATION PROBLEM($H_T^{(i)}, H_C^{(i)}, u_{opt}^{(i)}$)
2:    $H_T = H_T^{(i)}, H_C = H_C^{(i)}$
3:    $W_T = H_T^H H_T, W_C = (H_C^H H_C + \gamma_C I), \gamma_C > 0$ (small)
4:    Lagrange MNLS:

$$u_{opt}^{(i)} = W_C^{-1} H_T^H \left(H_T W_C^{-1} H_T^H\right)^\dagger p_T$$

Or Generalized Eigenvalue:

$$\text{Choose } u_{opt}^{(i)} \text{ such that } \lambda_{max}(W_T, W_C) = \sup_{u \neq 0} \frac{u^H W_T u}{u^H W_C u}$$

Solution through Generalized Eigenvalue Decomposition $$\lambda_{max} = \max\{\lambda | \det(\lambda W_C - W_T) = 0\}$$

Other optimization criteria can be applied, e.g. constant modulus or weighted solutions. These solutions can be generated separately or in parallel.

5: end procedure

6: procedure TEST SOLUTION($u_{opt}^{(i)}, G_T, G_C$)
7:    for all $M + L$ Control and Critical points $k = 1, 2, \cdots, M + L$ do
8:        STF Using $u_{opt}^{(i)}$ and form $X_k$. $G_k = \text{trace}\{X_k^H X_k\}$
9:    end for
10:   $G_T$ sum of $G_k$ at control points
11:   $G_C$ sum of $G_k$ at critical points
12: end procedure

Fig. 8B2

13: procedure MEASURE CONTROL POINT DIRECTIVITIES($u_{opt}^{(i-1)}$, $H_T^{(i)}$)
14:     for all $M$ Control Points, $m = 1, 2, \cdots, M$ do
15:         STF Focus using $u_{opt}^{(i-1)}$
16:         Form $X_m$ associated with $\vec{r}_m$
17:         $h_T(\vec{r}_m) \leftarrow \max_x x^H X_m^H X_m x$ (e-vec corres. to the largest e-val)
18:     end for
19:     $H_T^{(i)} = [h_T(\vec{r}_1) h_T(\vec{r}_2) \cdots h_T(\vec{r}_M)]^H$
20: end procedure

21: procedure MEASURE CRITICAL POINT DIRECTIVITIES($u_{opt}^{(i-1)}$, $H_C^{(i)}$)
22:     for all $L$ Critical Points, $l = 1, 2, \cdots, L$ do
23:         STF Focus using $u_{opt}^{(i-1)}$
24:         Form $X_l$ associated with $\vec{r}_l$
25:         $h_T(\vec{r}_l) \leftarrow \max_x x^H X_l^H X_l x$ (e-vec corres. to the largest e-val)
26:     end for
27:     $H_C^{(i)} = [h_T(\vec{r}_1) h_T(\vec{r}_2) \cdots h_T(\vec{r}_l)]^H$
28: end procedure

29: procedure DEFINING FOCUSED DATA MATRIX(DMUA Lattice and RF echo from STF, RoI $\vec{r}_m$ & $R$, $X_m$)
30:     Define RoI $\{\vec{r} : |\vec{r} - \vec{r}_m| < R\}$
31:     for all $N$ DMUA elements $n = 1, 2, \cdots, N$ do
32:         Determine $R_{m,n} = |\vec{r}_n - \vec{r}_m|$ and $R_{m,n}^{(min,max)} = R_{m,n} \mp R$ $$X_m(:,n) = \mathcal{H}\left\{RF_n\left(\left\lceil \frac{2 * R_n^{min} * F_s}{c} \right\rceil : \left\lceil \frac{2 * R_n^{max} * F_s}{c} \right\rceil\right)\right\}$$

where $\mathcal{H}\{\cdot\}$ is the Hilbert transform and $\lceil \cdot \rceil$ is the ceiling quantizer.
33:     end for
34: end procedure

Algorithm 2 Image-based Calibrated Thermal Response
---

1: procedure ESTIMATE FOCAL INTENSITY ($I_0$) IN SITU($\boldsymbol{H}_T^{(i)}, \boldsymbol{H}_C^{(i)}, \boldsymbol{u}_{opt}^{(i)}$)
2:     Run the driver to generate $\boldsymbol{u}_{opt}^{(i)}$ at low power (e.g. using $P_{dc} = 5 - 10\%$ of maximum DC supply power)
3:     Evaluate the Intensity Gain $$G_T = \frac{\boldsymbol{u}_{opt}^H \boldsymbol{W}_T \boldsymbol{u}_{opt}}{\boldsymbol{u}_{opt}^H \boldsymbol{u}_{opt}}$$

4:     Estimate average surface intensity, $I_{surface} = \eta P_{dc}/Area$, where $\eta$ is the efficiency and $Area$ is the surface area of the DMUA.
5:     Estimate Focal Intensity at Target Points using $\boldsymbol{H}_T^{(i)} \boldsymbol{u}_{opt} = \boldsymbol{p}_T$.
6:     From STF images, estimate focal intensity at each target point (accounting for attenuation and reflection in the path of the HIFU beam)
7: end procedure

8: procedure SUB-THERAPEUTIC HIFU WITH STF($\boldsymbol{u}_{opt}^{(i)}, I_{sub}$)
9:     Run sequence of therapy bursts and STF images as shown in Figure 3.
10:     Perform strain imaging using STF or M2D-mode echo data.
11:     Estimate Initial Heating Rate based on approximate tissue properties (e.g. speed of sound, absorption, etc.)
12: end procedure

Algorithm 3 Image-based Measurement of Cavitation Threshold In Situ
---
1: procedure ESTIMATE FOCAL PRESSURE $(p_T)$ IN SITU$(\boldsymbol{H}_T^{(i)}, \boldsymbol{H}_C^{(i)}, \boldsymbol{u}_{opt}^{(i)})$
2:     Run the driver to generate $\boldsymbol{u}_{opt}^{(i)}$ at low power (e.g. using $P_{dc}$ = 5 - 10% of maximum DC supply power) and short (sub-millisecond) duration
3:     Estimate average surface intensity, $I_{surface} = \eta P_{dc}/Area$, where $\eta$ is the efficiency and $Area$ is the surface area of the DMUA.
4:     Estimate the particle velocity at the surface of each DMUA element.
5:     Estimate Peak Pressure at Target Points using $\boldsymbol{H}_T^{(i)}\boldsymbol{u}_{opt} = \boldsymbol{p}_T$.
6:     From STF images, estimate focal peak pressure at each target point (accounting for attenuation and reflection in the path of the HIFU beam)
7: end procedure

8: procedure SUB-THERAPEUTIC HIFU WITH STF$(\boldsymbol{u}_{opt}^{(i)}, p_{sub})$
9:     Run sequence of therapy bursts and STF images as shown in Figure 3.
10:     Perform QB-mode using STF or M2D-mode echo data.
11:     Detect, localize, and characterize cavitation events from QB-mode data.
12:     Compute Probability of New Cavitation Events per HIFU burst.
13: end procedure

*Fig. 9C1*
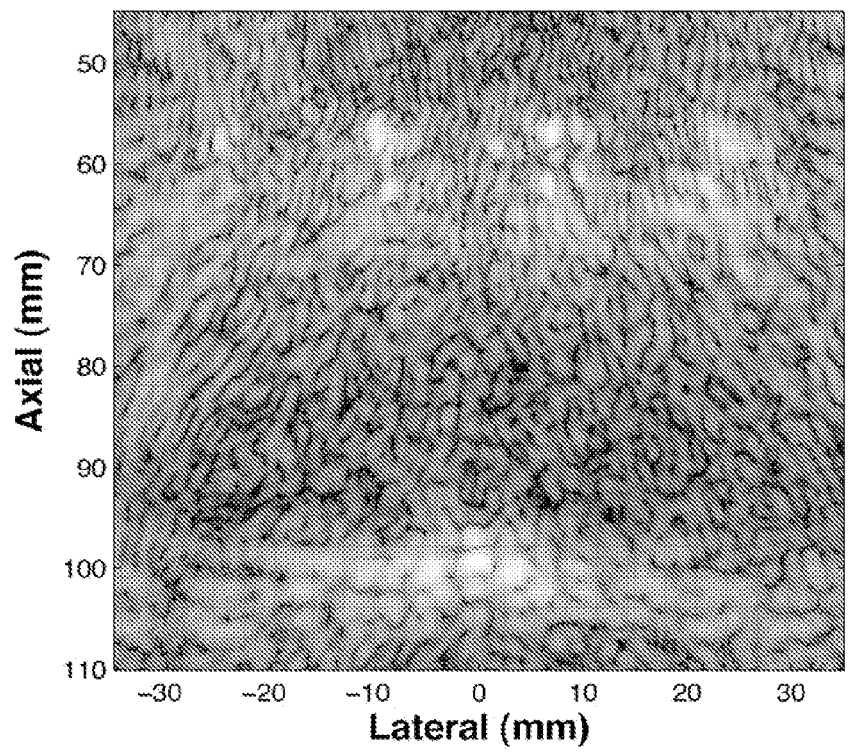
*Fig. 9C2*
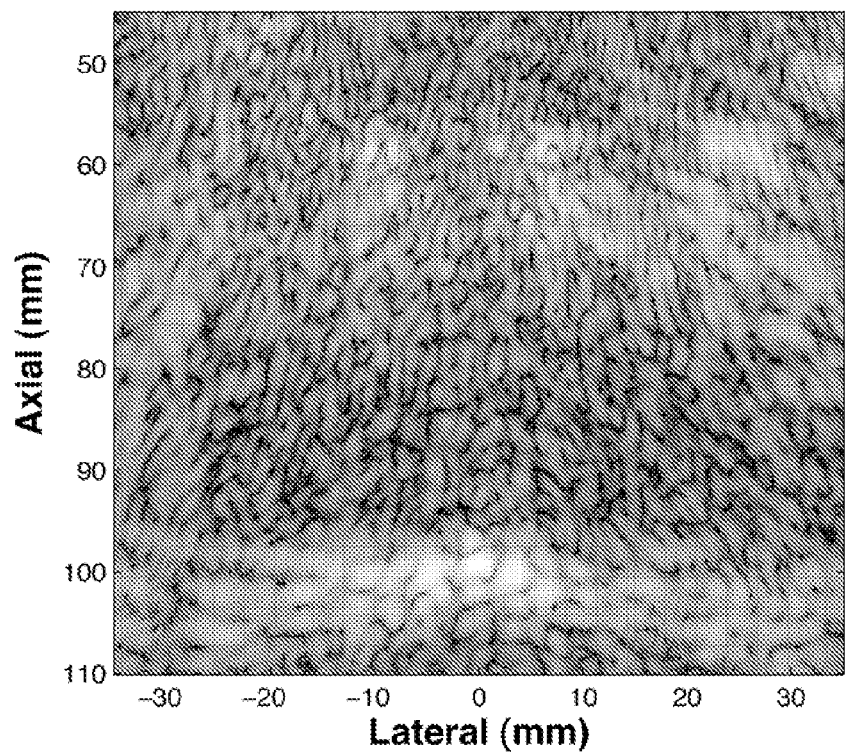

*Fig. 9F*

| Case ($x_T, z_T$) | $T_T/T_{Rib}$ | $E_T/E_{rib}$ (dB) | $\Delta E$ (dB) |
|---|---|---|---|
| Geometric Focusing (0,100) | 0.94 | 4.1, 6.2 | |
| Adaptive Refocusing (0,100) | 6.7 | 14.3, 13.1 | 10.2, 6.9 |
| Geometric Focusing (5,100) | 1.8 , 1.0 | -14.8, -7.6 | |
| Adaptive Refocusing (5,100) | 3.8, 2.7 | 0.2, 12.1 | 15.0, 19.7 |
| Geometric Focusing (10,100) | 0.4, 0.6 | -9.0, -10.9 | |
| Adaptive Refocusing (10,100) | 1.7, 2.9 | 1.6 , -2.4 | 10.6, 8.5 |

Double entries are for right and left ribs, respectively.

Fig. 9G1
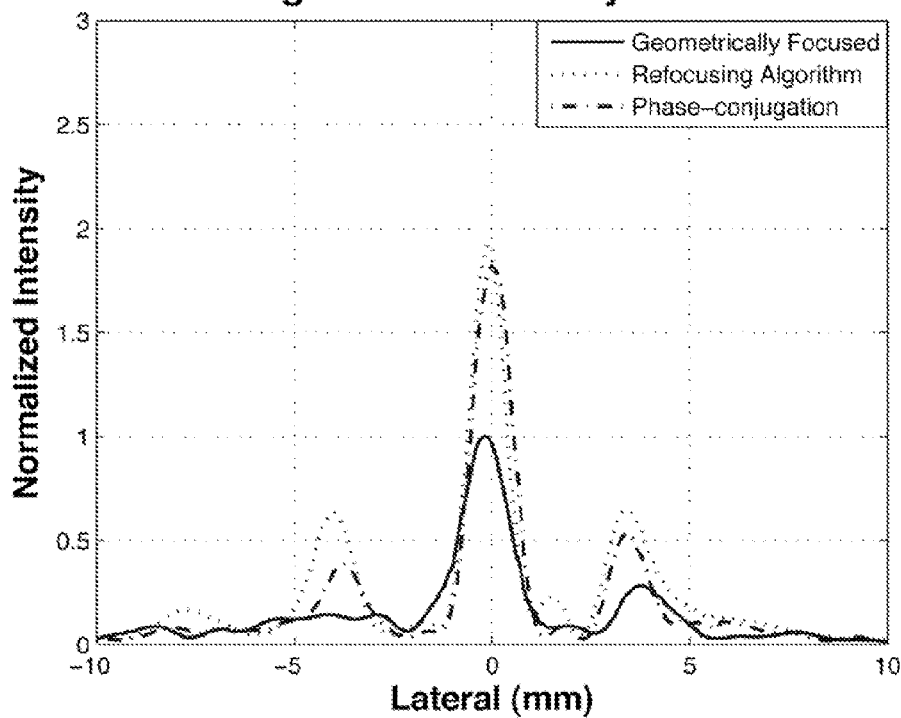
Fig. 9G2
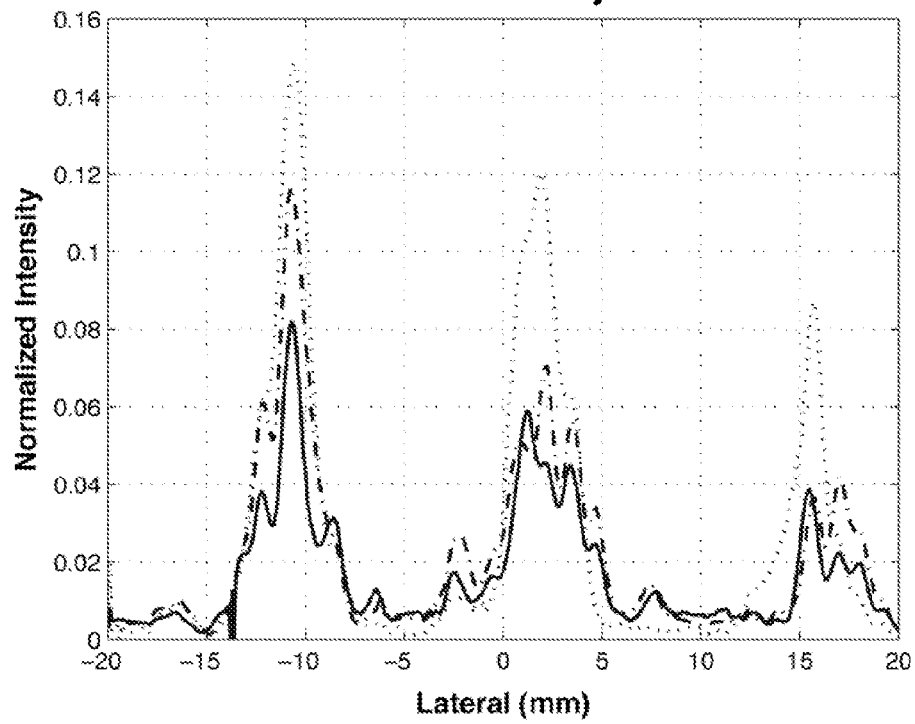

DUAL MODE ULTRASOUND TRANSDUCER (DMUT) SYSTEM AND METHOD FOR CONTROLLING DELIVERY OF ULTRASOUND THERAPY

CROSS REFERENCE TO RELATED APPLICATIONS

This application is the U.S. National Stage of International Application No. PCT/US2011/039837, filed on 9 Jun. 2011, entitled "Dual Mode Ultrasound Transducer (DMUT) System and Method For Controlling Delivery of Ultrasound Therapy", and published in the English language on 15 Dec. 2011, as International Publication No. WO 2011/156624 A2, which claims the benefit of U.S. Provisional Application Ser. No. 61/353,096 filed 9 Jun. 2010, entitled "Dual Mode Ultrasound Transducer (DMUT) System for Monitoring and Control of Lesion Formation Dynamics" and U.S. Provisional Application Ser. No. 61/475,550 filed 14 Apr. 2011, entitled "Vascular Characterization Using Ultrasound Imaging", all of which are incorporated herein by reference in their entirety.

STATEMENT REGARDING FEDERALLY SPONSORED RESEARCH OR DEVELOPMENT

This invention was made with government support under EB008191 awarded by National Institutes of Health. The government has certain rights in the invention.

BACKGROUND

The disclosure herein relates generally to ultrasound delivery apparatus (e.g., delivery systems) and ultrasound therapy provided therewith. More particularly, the disclosure herein pertains to ultrasound therapy methods, which can be used in vitro and in vivo, and ultrasound delivery apparatus for providing such ultrasound therapy. More particularly, the disclosure herein pertains to ultrasound therapy methods and systems that use ultrasound imaging therewith, e.g., ultrasound therapy applications (e.g., thermal and non-thermal therapy relating to vasculature (e.g., decrease plaque growth), nerve structure (e.g., denervation), tumor (e.g., tissue ablation or lesion formation), cardiac tissue (e.g., cardiac ablation), drug delivery (e.g., activation of drug in tissue), etc.).

Current technology for providing therapy using ultrasonic energy is inadequate. In addition, current technology for imaging based on ultrasonic signals is inadequate. High-intensity focused ultrasound (HIFU) continues to receive increased attention as a therapeutic tool in the treatment of cancer and other tissue abnormalities (see, Wu, et al., "Advanced hepatocellular carcinoma: Treatment with high-intensity focused ultrasound ablation combined with transcatheter arterial embolization," RADIOLOGY, vol. 235, no. 2, pp. 659-667, May 2005; Wu, et al., "Feasibility of US-guided high-intensity focused ultrasound treatment in patients with advanced pancreatic cancer: Initial experience," RADIOLOGY, vol. 236, no. 3, pp. 1034-1040, September 2005; Yuh, et al., "Delivery of systemic chemotherapeutic agent to tumors by using focused ultrasound: Study in a murine model," RADIOLOGY, vol. 234, no. 2, pp. 431-437, February 2005; Blana, et al., "First analysis of the long-term results with transrectal HIFU in patients with localized prostate cancer," EURO UROLOGY, vol. 53, no. 6, pp. 1194-1203, June 2008; Uchida, et al., "Transrectal high-intensity focused ultrasound for the treatment of localized prostate cancer: Eightyear experience," Int. J. UROLOGY, vol. 16, no. 11, pp. 881-886, November 2009; and Hindley, et al., "MRI guidance of focused ultrasound therapy of uterine fibroids: Early results," Am. J. ROENTGENOLOGY, vol. 183, no. 6, pp. 1713-1719, December 2004).

HIFU offers some unique advantages as a form of non-ionizing radiation suitable for the localized treatment of deep-seated tumors in a noninvasive or minimally invasive manner (see, Sanghvi, et al., "New developments in therapeutic ultrasound," IEEE Eng. Med. Biol. Mag., vol. 15, no. 6, pp. 83-92, November/December 1996). Image guidance using diagnostic MRI and ultrasound (see, Tempany, et al., "MR imaging-guided focused ultrasound surgery of uterine leiomyomas: A feasibility study," Radiology, vol. 226, pp. 897-905, November 2003; and Sanghvi, et al., "Noninvasive surgery of prostate tissue by high-intensity focused ultrasound," IEEE Trans. Ultrason., Ferroelectr., Freq. Contr., vol. 43, no. 6, pp. 1099-1110, November 1996) has led to increased acceptance of HIFU as a noninvasive therapeutic tool. Currently, HIFU is approved worldwide for use in the treatment of uterine leimyomas and prostate cancer. The HIFU beam experiences minimum distortion when focusing at the target sites by utilizing a noninvasive probe for the treatment of the uterine leimyomas and an intracavitary transducer for the prostate (see, Chan, et al., "An image-guided high intensity focused ultrasound device for uterine fibroids treatment," Med. Phys., vol. 29, pp. 2611-2620, 2002; and Poissonnier, et al., "Control of prostate cancer by transrectal HIFU in 227 patients," Eur. Urol., vol. 51, pp. 381-387, 2007).

During the treatment session, image guidance is vital to target the treatment location and to avoid the potential for collateral damage to the intervening tissue in the path of the HIFU beam. Temperature-sensitive MRI has been used in monitoring the application of HIFU in the treatment of uterine fibroids, and ultrasound has been shown to provide adequate feedback in guiding the HIFU treatment of prostate cancer.

Current clinical HIFU systems employ concave mechanically scanned transducers with relatively low $f_{number}$ (i.e., to provide high focusing gain). Both single-element and (coarsely sampled) array transducers are currently being used. Array transducers for generating HIFU beams offer additional advantages of compensating for tissue heterogeneities in the path of the HIFU beam (see, Chapelon, et al., "New piezoelectric transducers for therapeutic ultrasound," Ultrasound Med. Biol., vol. 26, pp. 153-159, 2000; Pernot, et al., "High power density prototype for high precision transcranial therapy," in Proc. 3rd Int. Symp. Ther. Ultrasound, 2003, vol. 1, pp. 405-410; Hynynen et al., "Transskull ultrasound therapy: The feasibility of using image-derived skull thickness information to correct the phase distortion," IEEE Trans. Ultrason., Ferroelectr., Freq. Control, vol. 46, no. 5, pp. 752-755, May 1999; Ishida, et al., "Development and animal experiment of variable focusing HIFU system for prostate cancer treatment," in Proc. 3rd Int. Symp. Ther. Ultrasound, 2003, vol. 1, pp. 382-387; Seip, et al., "High-intensity focused ultrasound (HIFU) phased arrays: Recent developments in transrectal transducers and driving electronics," in Proc. 3rd Int. Symp. Ther. Ultrasound, 2003, vol. 1, pp. 423-428; Curiel, et al., "1.5-D high intensity focused ultrasound array for non-invasive prostate cancer surgery," IEEE Trans. Ultrason., Ferroelectr., Freq. Control, vol. 49, no. 2, pp. 231-242, February 2002; Martin, et al., "Investigation of HEM produced emulsion for acoustic hemostasis," in Proc. 3rd Int. Symp. Ther. Ultrasound, 2003, vol. 1, pp. 351-356; and Aubry, et al., "Transcostal high-intensity-focused ultrasound: Ex vivo adaptive focusing feasibility study," *Phys. Med. Biol.*, vol. 53, pp. 2937-2951, 2008).

Depending on the size and distribution of the array elements, amplitude and/or phase compensation of the driving signals to the elements can be used to refocus the HIFU beam at the target in the presence of tissue aberrations. This, of course, assumes that information about tissue aberration is reliably measured or estimated. One way to estimate these aberrations is by using 3-D numerical modeling of the acoustic wave propagation based on tissue parameters from pretreatment X-ray computed tomography (CT) or MRI patient datasets (see, Tanter, et al., "Focusing and steering through absorbing and aberrating layers: Application to ultrasonic propagation through the skull," *J. Acoust. Soc. Amer.*, vol. 103, pp. 2403-2410, 1998; and Sun, et al., "Focusing of therapeutic ultrasound through a human skull: A numerical study," *J. Acoust. Soc. Amer.*, vol. 104, pp. 1705-1715, 1998). This approach has been suggested for focusing HIFU beams through the skull, but it is only of limited value when targeting tumors in abdominal organs where motion is significant. Alternatively, implantable hydrophones can be used to measure the array directivity at or near the target and refocus the beam based on phase-conjugation or time-reversal methods (see, Seip, et al., "Dynamic focusing in ultrasound hyperthermia treatments using implantable hydrophone arrays," *IEEE Trans. Ultrason., Ferroelectr., Freq. Control*, vol. 41, no. 5, pp. 706-713, September 1994). This approach was suggested for focusing hyperthermia arrays where the acoustic sensors can be integrated with the necessary temperature sensors.

Recently the concept of dual-mode ultrasound array (DMUA) systems for image-guided application of therapeutic HIFU have been discussed (see, Ebbini, et al., "Lesion formation and visualization using dual-mode ultrasound phased arrays," in *Proc. IEEE Ultrason. Symp.*, October 2001, vol. 2, pp. 1351-1354; Steidl, et al., "Dual-mode ultrasound phased arrays for noninvasive surgery: Post-beamforming image compounding algorithms for enhanced visualization of thermal lesions," in *Proc. IEEE Int. Symp. Biomed. Imag.*, July 2002, pp. 429-432; Yao and Ebbini, "Real-time monitoring of the transients of HIFU-induced lesions," in *Proc. IEEE Ultrason. Symp.*, October 2003, vol. 1, pp. 1006-1009; Yao and Ebbini, "Dual-mode ultrasound phased arrays for imaging and therapy," in *Proc. IEEE Int. Symp. Biomed. Imag.*, April 2004, vol. 1, pp. 25-28; and Ebbini, et al., "Dual-mode ultrasound phased arrays for image-guided surgery," *Ultrason. Imag.*, vol. 28, pp. 201-220, 2006). The advent of piezo-composite transducer technology has provided transducers capable of producing high-power levels suitable for therapy with reasonably wide bandwidth suitable for imaging (see, Fleury, et al., "New piezocomposite transducers for therapeutic ultrasound," in *Proc. 2nd Int. Symp. Ther. Ultrasound*, 2002, vol. 1, pp. 428-436). Furthermore, piezo-composite technology results in array elements with low lateral cross-coupling leading to more predictable element and beam patterns, both in imaging and therapy modes. A number of approaches for improving the image quality of a prototype DMUA that was originally optimized for therapeutic performance have been investigated (see, Ebbini, "Deep localized hyperthermia with ultrasound phased arrays using the pseudoinverse pattern synthesis method," Ph.D. dissertation, Univ. Illinois, Urbana, 1990; and Wan and Ebbini, "Imaging with concave large-aperture therapeutic ultrasound arrays using conventional synthetic-aperture beamforming," *IEEE Trans. Ultrason., Ferroelectr., Freq. Control*, vol. 55, no. 8, pp. 1705-1718, August 2008), including conventional imaging in sector scan format (see, Simon, et al., "Combined ultrasound image guidance and therapy using a therapeutic phased array," *SPIE Med. Imag.*, vol. 3341, pp. 89-98, May 1998); and Cartesian coordinates using synthetic aperture (SA) and single transmit focus (STF) imaging (see, Ebbini, et al., "Lesion formation and visualization using dual-mode ultrasound phased arrays," in *Proc. IEEE Ultrason. Symp.*, October 2001, vol. 2, pp. 1351-1354), harmonic and nonlinear quadratic imaging (see, Yao, et al., "Enhanced lesion visualization in image-guided noninvasive surgery with ultrasound phased arrays," in *Proc. 23rd Annu. Int. Conf. IEEE Eng, Med. Biol. Soc.*, October 2001, vol. 3, pp. 2492-2495, nonlinear frequency compounding (see, Steidl, et al., "Dual-mode ultrasound phased arrays for noninvasive surgery: Post-beamforming image compounding algorithms for enhanced visualization of thermal lesions," in *Proc. IEEE Int. Symp. Biomed. Imag.*, July 2002, pp. 429-432), and the use of coded excitation with pseudoinverse filtering to balance axial and lateral resolution (see, Wan and Ebbini, "Imaging with concave large-aperture therapeutic ultrasound arrays using conventional synthetic-aperture beamforming," *IEEE Trans. Ultrason., Ferroelectr., Freq. Control*, vol. 55, no. 8, pp. 1705-1718, August 2008; and Shen and Ebbini, "Filter-based coded-excitation system for high-speed ultrasonic imaging," *IEEE Trans. Med. Imag.*, vol. 17, no. 6, pp. 923-934, December 1998).

In addition to problems associated with the possible obstruction of the HIFU beam by structures resulting in inadequate therapy at the target and/or treatment-limiting pain or damage to normal tissues in the path of the beam (e.g. ribs when targeting liver tumors), HIFU suffers from other limitations that may hinder a wider acceptance of this modality. For example, one limitation is the long treatment time compared to competing minimally invasive modalities. For example, a tumor may be treated in 15 minutes using RF ablation, but may require 2-3 hours using a conventional HIFU protocol (e.g., raster scan of small ablations within the focal region of the HIFU application).

Various technologies for noninvasive application of therapeutic HIFU have been discussed. For, example, such technologies may include piezo-composite array transducer technology (see, Chapelon, et al., "New piezoelectric transducers for therapeutic ultrasound," ULTRASOUND IN MEDICINE AND BIOLOGY, vol. 26, no. 1, pp. 153-159, January 2000) and noninvasive thermometry (see, Seip and Ebbini, "Non-invasive estimation of tissue temperature response to heating fields using diagnostic ultrasound," IEEE Trans. Biomed. Eng., vol. 42, no. 8, pp. 828-839, 1995; Seip, et al., "Noninvasive real-time multipoint temperature control for ultrasound phased array treatments," IEEE TRANSACTIONS ON ULTRASONICS FERROELECTRICS AND FREQUENCY CONTROL, vol. 43, no. 6, pp. 1063-1073, November 1996; Simon, et al., "Two-dimensional temperature estimation using diagnostic ultrasound," IEEE Trans. Ultrason., Ferroelect., Freq. Contr., vol. 45, pp. 989-1000, July 1998; Salomir, et al., "Hyperthermia by MR-guided focused ultrasound: Accurate temperature control based on fast MRI and a physical model of local energy deposition and heat conduction," Magnetic Resonance in Medicine, vol. 43, pp. 342-347, 2000; Vanne and Hynynen, "MRI feedback temperature control for focused ultrasound surgery," Physics in Medicine and Biology, vol. 48, no. 1, pp. 31, 2003; and Souchon, et al., "Monitoring the formation of thermal lesions with heat-induced echo-strain imaging: A feasibility study," Ultrasound in Medicineand Biology, vol. 31, pp. 251-259, 2005).

Phased array applicators offer unparalleled level of spatial and temporal control over the heating pattern, including simultaneous heating at multiple-focus locations (see, Ebbini, Deep Localized Hyperthermia with Ultrasound Phased Arrays Using the Psudoinverse Pattern Synthesis Method, Ph.D. thesis, University of Illinois, 1990; and Ebbini and Cain, "Experimental evaluation of a prototype cylindrical section ultrasound hyperthermia phased-array applicator," IEEE TRANSACTIONS ON ULTRASONICS FERROELECTRICS AND FREQUENCY CONTROL, vol. 38, no. 5, pp. 510-520, September 1991). This has many potential advantages in thermal therapy (see, Ebbini, et al., "Dual-mode ultrasound arrays for image-guided surgery," Ultrasonic Imaging, vol. 28, pp. 65-82, April 2006).

Temperature imaging using MRI is available on clinical MR-guided HIFU systems (MRgFUS) and can be credited in the increased awareness and acceptance of this form of noninvasive surgery (see, Salomir, et al. (2000); and Vanne and Hynynen (2003)). Feedback control algorithms of HIFU fields based on noninvasive temperature imaging using MRI has been described (see, Salomir, et al. (2000); Smith, et al., "Control system for an MRI compatible intracavitary ultrasound array for thermal treatment of prostate disease," INTERNATIONAL JOURNAL OF HYPERTHERMIA, vol. 17, no. 3, pp. 271-282, May-June 2001; Mougenot, et al., "Automatic spatial and temporal temperature control for MR-guided focused ultrasound using fast 3D MR thermometry and multispiral trajectory of the focal point," MAGNETIC RESONANCE IN MEDICINE, vol. 52, no. 5, pp. 1005-1015, November 2004; Sun, et al., "Adaptive real-time closed-loop temperature control for ultrasound hyperthermia using magnetic resonance thermometry," CONCEPTS IN MAGNETIC RESONANCE PART B-MAGNETIC RESONANCE ENGINEERING, vol. 27B, no. 1, pp. 51-63, October 2005; and Mougenot, et al., "Three-dimensional spatial and temporal temperature control with MR thermometry-guided focused ultrasound (mrghifu)," Magnetic Resonance in Medicine, vol. 61, pp. 603-614, 2009).

Ultrasound temperature estimation has also been described (see, Simon, et al., "Two-dimensional temperature estimation using diagnostic ultrasound," WEE Trans. Ultrason., Ferroelect., Freq. Contr., vol. 45, pp. 989-1000, July 1998; Miller, et al., "Fundamental limitations of noninvasive temperature imaging by means of ultrasound echo strain estimation," Ultrasound in Medicine and Biology, vol. 28, pp. 1319-1333, 2002; and Pernot, et al., "Temperature estimation using ultrasonic spatial compounding," hEE Trans. Ultrason., Ferroelect., Freq. Contr., vol. 51, no. 5, pp. 606-615, 2004), as well as a photoacoustic-based approach (see, Pramanik and Wang, "Thermoacoustic and photoacoustic sensing of temperature," JOURNAL OF BIOMEDICAL OPTICS, vol. 14, no. 5, September-October 2009). A number of different ultrasound thermography methods have been proposed (see, Seip and Ebbini, "Non-invasive estimation of tissue temperature response to heating fields using diagnostic ultrasound," IEEE Trans. Biomed. Eng., vol. 42, no. 8, pp. 828-839, 1995; Maass-Moreno and Damianou, "Noninvasive temperature estimation in tissue via ultrasound echo shifts. Part I. Theoretical model," The Journal of the Acoustical Society of America, vol. 100, pp. 2514-2521, 1996; and Arthur, et al., "In vivo change in ultrasonic backscattered energy with temperature in motion-compensated images," INTERNATIONAL JOURNAL OF HYPERTHERMIA, vol. 24, no. 5, pp. 389-398, 2008).

SUMMARY

Dual-mode ultrasound systems that provide real-time imaging and therapy delivery using the same transducer elements of a transducer array are described. The system may use a multi-channel driver to drive the elements of the array. The system may use real-time monitoring and feedback image control of the therapy based on imaging data acquired using the dual-mode ultrasound array (DMUA) of transducer elements. Further, for example, multimodal coded excitation using multi-channel arbitrary waveform generators with a linear amplifier driver may be used in both imaging and therapy modes. Still further, for example, adaptive, real-time refocusing for improved imaging and therapy can be achieved using array directivity vectors obtained from DMUA pulse-echo data. System may refer to, according to one or more embodiments of the present disclosure, apparatus with a number of several elements (e.g., means, devices, etc.) specifically connected with each other by way of electrical connection and being adapted to the specific functions of each element as described herein.

In one exemplary embodiment of a dual mode ultrasound transducer system described herein, the system includes an array of ultrasound transducer elements (e.g., the ultrasound transducer elements configured to deliver a plurality of sequential therapy bursts of ultrasonic energy to at least a portion of a target region and to transmit/receive imaging ultrasonic energy to/from the target region) and a control apparatus. The control apparatus (e.g., one or more elements, such as means or devices) may be configured to control conveyance of imaging signals to/from one or more of the plurality of ultrasound transducer elements; generate treatment region image data (e.g., of a target region and the path between the transducer elements of the array and the target region) usable to identify at least one or more target points within a target region based on imaging signals conveyed to/from one or more of the plurality of ultrasound transducer elements; generate therapy signals to drive one or more of the plurality of ultrasound transducer elements to deliver a plurality of sequential therapy bursts of ultrasonic energy to at least one of the one or more target points in the target region; and generate control image data based on imaging signals from one or more of the plurality of ultrasound transducer elements during and/or following delivery of each therapy burst of a plurality of sequential therapy bursts. The control image data generated during and/or following delivery (e.g., during and following, during, following, partially during and partially following) of a therapy burst is used (e.g., as feedback) to generate therapy signals to drive one or more of the plurality of ultrasound transducer elements to deliver a subsequent therapy burst of the plurality of sequential therapy bursts.

In one or more embodiments of the system, one or more of the following features may be used in combination with other features in the system: the control apparatus may be configured to generate treatment region image data usable to identify one or more critical points representative of intervening tissue in the path between the plurality of ultrasound transducer elements and the one or more target points within the target region based on imaging signals conveyed to/from one or more of the plurality of ultrasound transducer elements; the control apparatus may be configured to generate at least one imaging signal to drive one or more of the plurality of ultrasound transducers elements to transmit at least one single transmit energy pulse focused to one or more target points and/or one or more of the critical points resulting in pulse-echo data to be captured; the control apparatus may be configured to generate imaging signals to drive one or more of the plurality of ultrasound transducers to transmit sequential single transmit energy pulses focused to each of a plurality of one or more target points within the target region and/or one or more critical points resulting in pulse-echo data to be captured; the control apparatus may be configured to use coded excitation to generate at least one imaging signal to drive one or more of the plurality of ultrasound transducers to transmit at least one single transmit energy pulse focused to one or more target points within the target region and/or one or more critical points resulting in pulse-echo data to be captured; prior to delivery of a subsequent therapy burst of the plurality of sequential therapy bursts at therapeutic levels based on therapy signals generated using control image data generated during and/or following delivery of a previous therapy burst, the control apparatus may be configured to control a test of the subsequent therapy burst at sub-therapeutic levels; and the control apparatus may be configured to modify the therapy signals generated to deliver the subsequent therapy burst based on imaging data resulting from the test.

Still further, one or more of such embodiments of the system may include one or more of the following features: the control apparatus may be configured to generate at least one imaging signal to drive one or more of the plurality of ultrasound transducers to transmit at least one ultrasound energy pulse to the target region resulting in pulse-echo data to be captured by one or more of the plurality of ultrasound transducer elements between the generation of therapy signals that result in each sequential therapy burst of ultrasonic energy to be delivered to the target region via the plurality of ultrasound transducer elements; the control apparatus may be configured to generate control image data comprising ultrasound transducer element directivity data (e.g., wherein at least the ultrasound transducer element directivity data is used to generate therapy signals to drive one or more of the plurality of ultrasound transducer elements to deliver a subsequent therapy burst of the plurality of sequential therapy bursts); the control apparatus may be configured to generate control image data comprising thermal response data (e.g., wherein at least the thermal response data is used to generate therapy signals to drive one or more of the plurality of ultrasound transducer elements to deliver a subsequent therapy burst of the plurality of sequential therapy bursts); the control apparatus may be configured to generate control image data comprising displacement and/or strain data associated with at least the target region (e.g., wherein at least the displacement and/or strain data is used to generate therapy signals to drive one or more of the plurality of ultrasound transducer elements to deliver a subsequent therapy burst of the plurality of sequential therapy bursts); and the control apparatus may be configured to generate control image data comprising data indicative of cavitation (e.g., wherein at least the data indicative of cavitation is used to generate therapy signals to drive one or more of the plurality of ultrasound transducer elements to deliver a subsequent therapy burst of the plurality of sequential therapy bursts).

Still further, one or more of such embodiments of the system may include one or more of the following features: a control channel associated with each of a plurality of ultrasound transducer elements of the array; the control apparatus may be configured to generate multiple channel therapy signals for driving the plurality of ultrasound transducer elements via the respective control channels to deliver energy to at least one target point in the target region (e.g., wherein each of the plurality of ultrasound transducer elements is driven at one or more drive parameters to focus the ultrasound energy for delivery of each sequential therapy burst); the control apparatus may be configured to adjust one or more of the drive parameters drive of one or more of the plurality of ultrasound transducer elements based on the control image data; a display apparatus to display image data and a user interface to allow a user to input one or more commands for real-time control of the delivery of the plurality of sequential therapy bursts (e.g., the user interface may be configured to allow a user to select at least one or more target points and/or one or more critical points for use in controlling delivery of the plurality of sequential therapy bursts); a control channel associated with each of the plurality of ultrasound transducer elements of the array, wherein each control channel associated with each of the plurality of ultrasound transducer elements includes a configurable diplexer (e.g., the configurable diplexer may include an amplifier having its output set to a high impedance state when a therapy signal is not being transmitted and/or a selectable voltage divider to attenuate a pulse echo signal received by the transducer element); a control apparatus including at least one processor coupled to a multimodal imaging apparatus (e.g., wherein the multimodal imaging apparatus may be configured to fuse image data resulting from a plurality of different imaging modes and/or the control apparatus may be configured to provide the fused image data for display and/or for use to generate control image data); the control apparatus may be configured to generate the control image data substantially in real-time relative to generation of the therapy signals; at least one other ultrasound diagnostic apparatus configured to capture ultrasound pulse-echo data of at least a portion of the target region in response to the delivery of one or more of the plurality of sequential therapy bursts; the control apparatus may be configured to generate therapy signals usable for thermal treatments; the control apparatus may be configured to generate therapy signals usable for non-thermal treatments; and the control apparatus may be configured to generate therapy signals to drive one or more of the plurality of ultrasound transducer elements to deliver a plurality of sequential therapy bursts of ultrasonic energy to at least one of the one or more target points in the target region using coded excitation.

In another exemplary embodiment of a dual mode ultrasound transducer system, the system may include an array of ultrasound transducer elements (e.g., the ultrasound transducer elements may be configured to deliver a plurality of sequential therapy bursts of ultrasonic energy to at least a portion of a target region and to transmit/receive imaging ultrasonic energy to/from the target region); apparatus for controlling conveyance of imaging signals to/from one or more of the plurality of ultrasound transducer elements; apparatus for generating treatment region image data usable to identify at least one or more target points within a target region based on imaging signals conveyed to/from one or more of the plurality of ultrasound elements; apparatus for generating therapy signals to drive one or more of the plurality of ultrasound transducer elements to deliver a plurality of sequential therapy bursts of ultrasonic energy to at least one of the one or more target points in the target region, wherein each of the sequential therapy bursts is defined to produce a response at one or more target points within the target region; and apparatus for generating control image data based on imaging signals from one or more of the plurality of ultrasound transducer elements during and/or following delivery of each therapy burst of a plurality of sequential therapy bursts (i.e., wherein the control image data generated during and/or following delivery of a therapy burst is used (e.g., as feedback) to generate therapy signals to drive one or more of the plurality of ultrasound transducer elements to deliver a subsequent therapy burst of the plurality of sequential therapy bursts).

One or more embodiments of such a system may include one or more of the following features: apparatus for generating treatment region image data usable to identify one or more critical points representative of intervening tissue in the path between the plurality of ultrasound elements and the one or more target points within the target region based on imaging signals conveyed to/from one or more of the plurality of ultrasound elements; apparatus to generate at least one imaging signal to drive one or more of the plurality of ultrasound transducers to transmit at least one single transmit energy pulse focused to one or more of the target points and/or critical points resulting in pulse-echo data to be captured; prior to delivery of a subsequent therapy burst of the plurality of sequential therapy bursts at therapeutic levels based on therapy signals generated using control image data following delivery of a previous therapy burst, apparatus to control a test of the subsequent therapy burst at sub-therapeutic levels; apparatus for modifying therapy signals generated to deliver the subsequent therapy burst based on imaging results from the test; and apparatus to generate control image data including at least one of displacement and/or strain data, directivity data, thermal response data, and data indicative of cavitation for use in generating therapy signals to drive one or more of the plurality of ultrasound transducer elements to deliver a subsequent therapy burst of the plurality of sequential therapy bursts.

A dual mode ultrasound transducer therapy method is also provided. The method may include providing an array of ultrasound transducer elements (e.g., the ultrasound transducer elements may be configured to deliver a plurality of sequential therapy bursts of ultrasonic energy to at least a portion of a target region and to transmit/receive imaging ultrasonic energy to/from the target region); generating treatment region image data and identifying at least one or more target points within a target region thereof based on pulse echo data received by one or more of the plurality of ultrasound transducer elements; generating therapy signals to drive one or more of the plurality of ultrasound transducer elements to deliver a plurality of sequential therapy bursts of ultrasonic energy to at least one of the one or more target points in the target region to produce a response at the one or more target points within the target region; and generating control image data based on pulse echo data received by one or more of the plurality of ultrasound transducer elements following delivery of each therapy burst of a plurality of sequential therapy bursts (e.g., wherein the control image data generated during and/or following delivery of a therapy burst is used to generate therapy signals to drive one or more of the plurality of ultrasound transducer elements to deliver a subsequent therapy burst of the plurality of sequential therapy bursts).

In one or more embodiments of the method, one or more of the following features may be used in combination with other features in the method: generating at least one imaging signal to drive one or more of the plurality of ultrasound transducers to transmit at least one single transmit energy pulse focused to at least one or more target points within the target region resulting in pulse-echo data to be captured; identifying one or more critical points within the treatment region representative of intervening tissue in the path between the plurality of ultrasound transducer elements and the one or more target points within the target region; generating at least one imaging signal to drive one or more of the plurality of ultrasound transducers to transmit at least one single transmit energy pulse focused to one or more of the critical points resulting in pulse-echo data to be captured; generating imaging signals to drive one or more of the plurality of ultrasound transducers to transmit sequential single transmit energy pulses focused to each of a plurality of one or more target points within the target region or one or more critical points resulting in pulse-echo data to be captured; using coded excitation to generate at least one imaging signal to drive one or more of the plurality of ultrasound transducers to transmit at least one single transmit energy pulse focused to one or more target points within the target region and/or one or more critical points resulting in pulse-echo data to be captured; prior to delivery of a subsequent therapy burst of the plurality of sequential therapy bursts based on therapy signals generated using control image data generated during and/or following delivery of a previous therapy burst, testing the subsequent therapy burst at sub-therapeutic levels lower than therapeutic levels associated with the subsequent therapy burst; modifying the therapy signals generated to deliver the subsequent therapy burst based on imaging results from the test; generating control image data between the generation of therapy signals that result in each sequential therapy burst of ultrasonic energy to be delivered to the target region via the plurality of ultrasound transducer elements; generating control image data including at least one of directivity data, thermal response data, displacement and/or strain data associated with at least the target region (or any other mechanical response data), and data indicative of cavitation; generating multiple channel therapy signals for driving the plurality of ultrasound transducer elements via respective control channels to deliver energy to at least one target point in the target region, wherein each of the plurality of ultrasound transducer elements is driven at one or more drive parameters to focus the ultrasound energy for delivery of each sequential therapy burst; adjusting one or more drive parameters to drive each of the plurality of ultrasound transducer elements based on the control image data; displaying image data and providing a user interface to allow a user to input one or more commands for real-time control of the delivery of the plurality of sequential therapy bursts; selecting, by a user using the user interface, at least one or more target points and/or one or more critical points for use in controlling delivery of the plurality of sequential therapy bursts; fusing image data resulting from a plurality of different imaging modes and providing the fused image data for display and/or for use to generate control image data; generating the control image data substantially in real-time relative to the therapy signals; using at least one other ultrasound diagnostic apparatus to capture ultrasound pulse-echo data of at least a portion of the target region in response to the delivery one or more of the plurality of sequential therapy bursts; and generating of therapy signals to drive one or more of the plurality of ultrasound transducer elements to deliver a plurality of sequential therapy bursts of ultrasonic energy to at least one of the one or more target points in the target region using coded excitation.

Still further, one or more of such embodiments of the method and/or system may include generation of therapy signals at amplitudes for use in non-thermal treatments and generation of therapy signals for use in one or more thermal treatments (e.g., delivery of therapy to a target region in which a blood vessel is located, delivery of therapy to a target region in which a tumor is located, delivery of therapy to a target region in which a nerve is located; activation of a drug in a target region, delivery of therapy to a target region in a vessel of the patient is located, etc.). Still further, in one or more embodiments of the method and/or systems, image control data may be obtained during delivery of one or more therapy bursts using coded excitation (e.g., with coded excitation, imaging can be performed even during the delivery of therapy; control image data (for example, which may be generated and/or provided during and/or following delivery of one or more therapy bursts for control of one or more subsequent therapy bursts) may be obtained based on imaging performed (e.g., at least in part) during the delivery of the therapy bursts, such as with use of coded excitation).

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2 is a flow chart depicting an exemplary ultrasound therapy method.

FIG. 3 is an illustration of real-time control of a therapeutic beam.

FIGS. 8A-8B show a flow diagram of an exemplary therapy method (e.g., taking into consideration directivities) and an exemplary algorithm for carrying out the method of the flow diagram, respectively.

FIGS. 8C-8D show a flow diagram of an exemplary therapy method (e.g., taking into consideration thermal response) and an exemplary algorithm for carrying out the method of the flow diagram, respectively.

FIGS. 8E-8F show a flow diagram of an exemplary therapy method (e.g., taking into consideration cavitation data) and an exemplary algorithm for carrying out the method of the flow diagram, respectively.

FIGS. 9A-9G are illustrations, graphs, etc. for use in relating to examples carried out and described at least in part herein with respect to driving pattern re-synthesis based on the same directivity used in image formation.

DETAILED DESCRIPTION OF EXEMPLARY EMBODIMENTS

Figure 1:
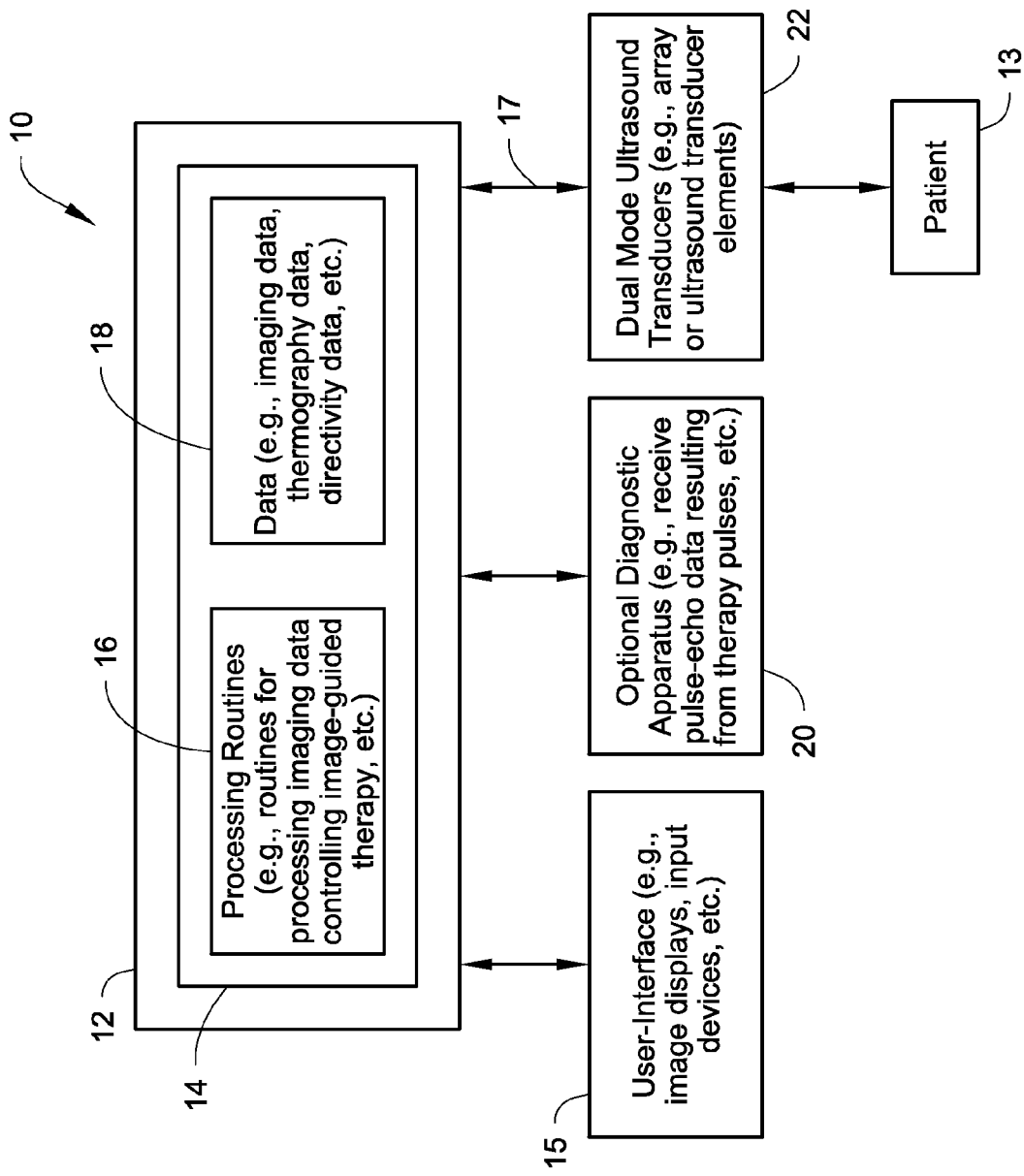
FIG. 1 is a block diagram depicting an exemplary ultrasound therapy system.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, apparatus, and systems shall be described with reference to FIGS. 1-12. It will be apparent to one skilled in the art that elements or processes (e.g., including steps thereof) from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 shows an exemplary dual mode ultrasound transducer therapy system 10 including control apparatus 12 (e.g., one or more processing apparatus) and one or more dual mode ultrasound transducers 22 (e.g., an array of configurable ultrasound transducer elements, such as a transducer array that is configurable for transmission of pulses and reception of echoes for imaging and configurable for delivering therapy pulses). The control apparatus 12 may be operably coupled to the array of transducer elements 22 (e.g., via a control channel for each of the transducer elements; a multi-channel configuration) to facilitate providing therapy pulses (e.g., a plurality of sequential therapy bursts; configured for operation with respect to phase/delay, amplitude, and/or spectral content to produce thermal, mechanical, and/or mixed therapeutic response) such as to a target region of a patient 13, as well as to provide for imaging of the target region or locations proximate thereto (e.g., capture of pulse-echo data) using the array of transducer elements (e.g., to monitor the response of tissue of the patient to a therapy burst and to provide control image data for use in generating a subsequent therapy burst).

For example, the array of ultrasound transducer elements 22 may include any suitable configuration for allowing imaging and therapy delivery to be accomplished using the same array (e.g., ultrasound transducer elements configured to deliver a plurality of sequential therapy bursts of ultrasonic energy to at least a portion of a target region and to transmit/receive imaging ultrasonic energy to/from the target region). Further, for example, the control apparatus 12 may be configured to control conveyance of imaging signals (see, for example, imaging pulses 42 in FIG. 3) to/from one or more of the plurality of ultrasound transducer elements (e.g., in one or more imaging modes, such as synthetic aperture (SA) imaging or B-mode imaging, M2D-mode strain imaging, quadratic B-mode (QB-mode) imaging, inverse scattering reconstruction, single transmit focus (STF) imaging, thermal imaging, etc.). At least in one embodiment, the control apparatus 12 is configured to generate treatment region image data (e.g., including a target region and other regions associated therewith, such as regions in the path of the imaging or therapeutic beams to the target region) based on imaging signals conveyed to/from one or more of the plurality of ultrasound transducer elements (e.g., carrying out SA imaging) usable to identify at least one or more target points within the target region (e.g., the one or more target points being selectable by a user via a user interface).

Still further, the control apparatus 12 may be configured to generate therapy signals to drive one or more of the plurality of ultrasound transducer elements of the array 22 (see, for example, therapy bursts 40 in FIG. 3) to deliver a plurality of sequential therapy bursts of ultrasonic energy to at least one of the one or more target points in the target region (e.g., each of the sequential therapy bursts being defined to produce a response at the one or more target points within the target region). Yet further, the control apparatus 12 may be configured to generate control image data (e.g., directivity data, high resolution image data, mechanical response data such as displacement and/or strain data, test pattern data, thermal response data, cavitation and boiling activity data, etc.) based on imaging signals (see, for example, imaging bursts or pulses 46 in FIG. 3) from one or more of the plurality of ultrasound transducer elements (e.g., using STF imaging, M2D-mode flow and strain imaging, QB-mode imaging, etc.) following delivery of each therapy burst of a plurality of sequential therapy bursts (e.g., control image data may be generated after each therapy burst is delivered; to monitor the response of the therapy burst). The control image data generated following delivery of a therapy burst is used to generate therapy signals to drive one or more of the plurality of ultrasound transducer elements to deliver a subsequent therapy burst of the plurality of sequential therapy bursts (e.g., the definition of the subsequent therapy burst takes into consideration the control image data, or in other words, takes into consideration image data that reflects the response of the tissue to a previous therapy burst). For example, in one or more embodiments, control image data may be generated after the delivery of each therapy burst such that the following therapy burst in the sequence of therapy bursts to be delivered is defined based at least in part on the response caused by the prior therapy burst (e.g., the plurality of therapy bursts or focused therapy beam of ultrasound energy can be guided based on the control image data generated between therapy bursts).

As shown in FIG. 3, the plurality of therapy bursts 40 (e.g., pulses) when delivered as therapy provide a focused therapy beam. Each of the therapy bursts 40 (e.g., pulses) may be defined differently (e.g., with different characteristics, including but not limited to, phase/delay, amplitude, and spectral content). Such therapy bursts 40 are delivered by driving the transducer elements of the array 22 based on one or more therapy signals defining the nature of such bursts. As such, during delivery of such therapy bursts 40, the beam formed thereby may be resynthesized (e.g., refocused) to change the beam over time and space (e.g. for motion tracking). As described herein, the imaging pulses 46 (e.g., which may include one pulse or more than one pulse between each therapy burst 40) are used to provide image control data for use in redefining the therapy beam over time (e.g., guide the beam). In other words, the focused beam is imaged and guided based on the imaging performed in real-time with the delivery of the therapy (e.g., control image data may be generated after each therapy burst 40 to control the next burst 40 of the beam).

For example, in one or more embodiments, such therapy bursts may be pulses having a duration less than 10 microsecond, less than 1 millisecond, or less than 10 millisecond. Further, the time between therapy pulses may be less than 200 microsecond, less than 1 millisecond, or less than 10 millisecond. Still further, the time between therapy pulses may be greater than 200 microsecond, greater than 1 millisecond, or greater than 10 millisecond.

In one or more embodiments, imaging and therapy pulses are produced by a multi-channel arbitrary waveform generator with deep memory to allow variable delay control for the different DMUA elements. The imaging pulses may be generally short in duration (approximately 1 microsecond for typical pulse-echo SA and STF imaging). Longer durations may be used in coded excitation mode (approximately 4-12 microseconds to maximize the time bandwidth product, which optimizes signal-to-noise ratio, and minimizes clutter). The therapy bursts may be sinusoidal, mixed-frequency, or synthesized to achieve beneficial spectral contents (e.g. to generate stable cavitation and/or enhance the heating rate in cavitation-enhanced thermal therapy). Further, therapy burst amplitudes may be chosen based on the desired heating rate in thermal therapies and the cavitation threshold in cavitation therapy. Further, for example, the duration of therapy bursts may be in the microsecond range for cavitation therapy and millisecond range for thermal or cavitation-enhanced thermal therapies.

As mentioned above, the amplitude, duration, and spectral content of therapy bursts can be adjusted in real-time based on imaging feedback between bursts, i.e. therapy bursts are dynamically changed during treatment. For example, a high-intensity cavitation inducing burst of 10 microsecond duration may be elongated to 15 microseconds to increase the probability of generating cavitation bubbles at a given intensity or peak pressure. Alternatively, for example, the amplitude of the burst may be increased if the driver and the transducer can produce the desired focal intensity/peak pressure. Still further, for example, alternatively, the synthesis of a mixed frequency burst where the resulting pressure waveform at the focus produces beneficial sequence of peaks and troughs that increase the probability of forming cavitation bubbles may be used. The mixed frequency approach may be employed in cavitation-enhanced thermal therapy where the low-frequency component may be chosen to produce and sustain cavitation bubbles while the higher frequency component may be chosen based on heating considerations. In general, the therapy burst can be synthesized as an arbitrary waveform to maximize the therapeutic gain (e.g., thermal, cavitational, or mixed) at the desired target point(s).

With further reference to FIG. 1, the control apparatus 12 includes data storage 14. Data storage 14 allows for access to processing programs or routines 16 and one or more other types of data 18 that may be employed to carry out the exemplary therapy and imaging processes (e.g., one which is shown generally in the block diagram of FIG. 2).

For example, processing programs or routines 16 may include programs or routines for performing computational mathematics, matrix mathematics, compression algorithms (e.g., data compression algorithms), calibration algorithms, image construction algorithms, inversion algorithms, signal processing algorithms, standardization algorithms, comparison algorithms, vector mathematics, or any other processing required to implement one or more embodiments as described herein (e.g., provide multiple modes of imaging, provide therapy, perform pattern test processes, perform fusion of data resulting from multiple modes of imaging, generate a graphical user interface to allow a user to input commands, carry out motion tracking or speckle tracking, identify critical points, specify virtual thermometry probes (e.g., based on ultrasound thermometry), modulate therapy bursts (e.g., amplitude and/or duration), etc.). Exemplary mathematical formulations/equations that may be used in the systems and methods described herein are more specifically described herein with reference to FIGS. 3-12.

Data 18 may include, for example, sampled pulse-echo information (e.g., sampled or collected using the one or more transducers elements 22, control image data (e.g., directivity data, imaging data, thermal response data, mechanical response data including displacement/strain data associated with the target region, such as measurements or vascular characteristics), results from one or more processing programs or routines employed according to the disclosure herein (e.g., image data from STF imaging, SA imaging, etc.), or any other data that may be necessary for carrying out the one or more processes or methods described herein.

In one or more embodiments, the system 10 may be implemented using one or more computer programs executed on programmable computers, such as computers that include, for example, processing capabilities (e.g., computer processing units (CPUs), graphical processing units (GPUs)), data storage (e.g., volatile or non-volatile memory and/or storage elements), input devices, and output devices. Program code and/or logic described herein may be applied to input data to perform functionality described herein and generate desired output information (e.g., images for use in guiding a focused beam, control image data for use in defining subsequent therapy pulses, etc.). The output information may be applied, or otherwise used, as input to, or by, one or more other devices and/or processes as described herein (e.g., the control image data may be used to refocus the therapeutic beam, the image data may be used for other diagnostic purposes, etc.).

The program(s) or routine(s) used to implement the processes described herein may be provided using any programmable language, e.g., a high level procedural and/or object orientated programming language that is suitable for communicating with a computer system. Any such programs may, for example, be stored on any suitable device, e.g., a storage media, readable by a general or special purpose program, computer or a processor apparatus for configuring and operating the computer (e.g., processor(s)) when the suitable device is read for performing the procedures described herein. In other words, at least in one embodiment, the system 10 may be implemented using a computer readable storage medium, configured with one or more computer programs, where the storage medium so configured causes the computer to operate in a specific and predefined manner to perform functions described herein.

Likewise, the system 10 may be configured at a remote site (e.g., an application server) that allows access by one or more users via a remote computer apparatus (e.g., via a web browser), and allows a user to employ certain functionality according to the present disclosure (e.g., user accesses a graphical user interface associated with one or more programs to process data).

The control apparatus 12, may be, for example, any fixed or mobile computer system (e.g., a personal computer or mini computer, for example, with CPUs, GPUs, etc.). The exact configuration of the computing apparatus is not limiting and essentially any device capable of providing suitable computing capabilities and control capabilities (e.g., control the imaging, such as acquiring data, such as pulse-echo data; control therapy, such as with use of control image data) may be used. Further, various peripheral devices, such as a computer display, mouse, keyboard, memory, printer, scanner, etc. are contemplated to be used in combination with the control apparatus 12, such as for visualization of imaging results (e.g., display of multimodal images, display of therapy delivery in real time such as with use of high intensity focused ultrasound, etc.).

Further, in one or more embodiments, any output (e.g., an image, image data, an image data file, a digital file, a file in user-readable format, etc.) may be analyzed by a user, used by another machine that provides output based thereon, etc.

As described herein, a digital file may be any medium (e.g., volatile or non-volatile memory, any tangible memory medium, etc.) containing digital bits (e.g., encoded in binary, trinary, etc.) that may be readable and/or writeable by control apparatus 12 described herein.

Also, as described herein, a file in user-readable format may be any representation of data (e.g., ASCII text, binary numbers, hexadecimal numbers, decimal numbers, audio, graphical) presentable on any medium (e.g., paper, a display, sound waves, etc.) readable and/or understandable by a user.

Generally, the methods and systems as described herein may utilize algorithms implementing computational mathematics (e.g., matrix inversions, substitutions, Fourier transform techniques, etc.) to reconstruct the images described herein (e.g., from pulse-echo data).

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

One will recognize that a graphical user interface may be used in conjunction with the embodiments described herein. The user interface may provide various features allowing for user input thereto, change of input, importation or exportation of files, or any other features that may be generally suitable for use with the processes described herein. For example, the user interface may allow default values to be used or may require entry of certain values, limits, threshold values, or other pertinent information. Any input devices (e.g., as part of a graphical user interface) to the system may be used that allow a user of the therapy system 10 to input commands, or input any other information (e.g., to select critical points, to abandon therapy, to initiate therapy, to modify therapy, etc.). For example, a key pad, a mouse, a touch screen, or any other input device may be used.

The methods described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, image processing devices, or other devices. The term "control apparatus", "controller", "processor", or "processing circuitry" may generally refer to any of the foregoing circuitry, including processing circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

The therapy system 10 may further be used to perform one or more therapeutic operations or produce one or more therapeutic responses (e.g., with respect to a patient 13). In other words, for example, in one or more embodiments, the therapy system 10 may be a non-invasive therapy (e.g., thermal therapy and/or non-thermal therapy, such as mechanical therapy) that produces responses in one or more target regions of a patient 13. For example, thermal and non-thermal therapy may be applied to vasculature (e.g., to decrease plaque growth by thermally treating the base of plaque on a vessel wall). Further, for example, therapy may be applied to one or more nerves of a patient's nervous system (e.g., denervation of at least portions of one or more nerves, such as in the renal region). Still further, for example, treatment of tumor or cancerous tissue may be carried out (e.g., ablation of tissue or lesion formation using a high intensity focused ultrasound beam). In addition, therapy may be applied to cardiac tissue (e.g., cardiac ablation), may be used in drug delivery (e.g., activation of drug provided in tissue), may be used to treat uterine fibroids, may be applied to target nerves (e.g. renal denervation), or in other vascular applications (e.g. thrombolysis, varicose vein), etc.

In one or more embodiments, the therapy system 10 may be used, for example, to carry out one or more treatments as described in PCT International Publication No. WO2009/002492 entitled "Image Guided Plaque Ablation," published 31 Dec. 2008, and incorporated herein by reference. For example, the ultrasound therapy described herein may be used for reducing vascular plaque non-invasively. For example, the ultrasound therapy described herein may be delivered to non-invasively perform ablation of plaque as described in PCT International Publication No. WO2009/002492.

For example, the therapy system 10 may produce a high intensity focused beam (e.g., a plurality of sequential therapy bursts) for non-invasively elevating the temperature of tissue by ultrasound waves, with the focused beam being guided using control image data generated during and/or following the delivery of a therapy burst (e.g., for use in defining a subsequent burst to be applied). For example, the system may include at least one ultrasound delivery device adapted to deliver ultrasound waves to a focal point of targeted tissue (e.g., the array of dual mode ultrasound transducer elements 22); temperature monitoring capabilities for monitoring the temperature of targeted tissue at the focal point (e.g., control image data that includes thermal image data generated following the delivery of therapy bursts for use in defining the next therapy burst); and a controller for steering and controlling the ultrasound delivery device to deliver ultrasound energy waves at a focal point to elevate the temperature of targeted tissue to a desired temperature (e.g., controlling or refocusing the energy waves using the control image data; to guide the focused beam).

Further, for example, the therapy system may use one or more imaging modes as described herein to produce image data of at least a portion of a mammalian body, e.g., such that the location of at least one vascular plaque in said image can be determined and to ascertain the location of the base of said vascular plaque (e.g., an M2D imaging mode as described in U.S. Provisional Application Ser. No. 61/475,550 filed 14 Apr. 2011, entitled "Vascular Characterization Using Ultrasound Imaging" which is incorporated herein by reference in their entirety).

For example, ultrasound therapy system 10 may image to provide treatment region image data such that one or more target locations at the base of the plaque may be ascertained or identified (e.g., selected target points by a user of the therapy system 10). Still further, one or more embodiments of the therapy system 10 provided herein may be used in a method for elevating the temperature at a target location by an energy wave using an ultrasound therapy system (e.g., which is the same ultrasound system used to image for controlling the therapeutic beam of energy). For example, the method may include delivering a beam of ultrasound energy waves from a source to the target location; monitoring the temperature of the target location; and stopping the delivering of the beam of ultrasound energy waves if a desired temperature at the target location has been reached.

Further, a method of preparing a plan for non-invasively elevating the temperature of tissue in a vessel wall leading to regression of vascular plaque may include imaging at least a portion of a body to produce an image (e.g., using ultrasound imaging as described herein to image a vascular region); determining the location of at least one vascular plaque in said image (e.g., identifying target plaque region); ascertaining the location of the base of said vascular plaque and one or more target points or locations at the base of the plaque (e.g., identifying target points within the target plaque region to which the focused beam is to be delivered); determining the parameters for delivering ultrasound energy waves from a source to a focal point for elevating the temperature of targeted tissue in the vessel wall to a desired temperature, sufficient for reducing or destroying vaso vasorum; and controlling the delivery of ultrasound energy using control image data as described herein (e.g., resynthesis of the beam using directivity image data, thermal image data, displacement/strain image data, etc.).

In other words, the therapy system 10 may be described as using the same or similar transducer arrays described therein which can be used for both imaging (e.g., to monitor a therapy procedure), as well as for delivering therapy (e.g., to deliver high intensity focused ultrasound energy). For example, therapy may be delivered using the ultrasound transducer array 22 while the imaging modes using the same transducer array 22 may be used to guide the therapeutic beam, assess thermal and mechanical tissue response to estimate doses of therapy (e.g., initial dose of therapy), monitor and characterize tissue response during therapy, and assess the state of the treated tissue at the completion of each exposure to the therapeutic ultrasound energy (e.g., real time monitoring between periods of therapy delivery).

Figure 4A:
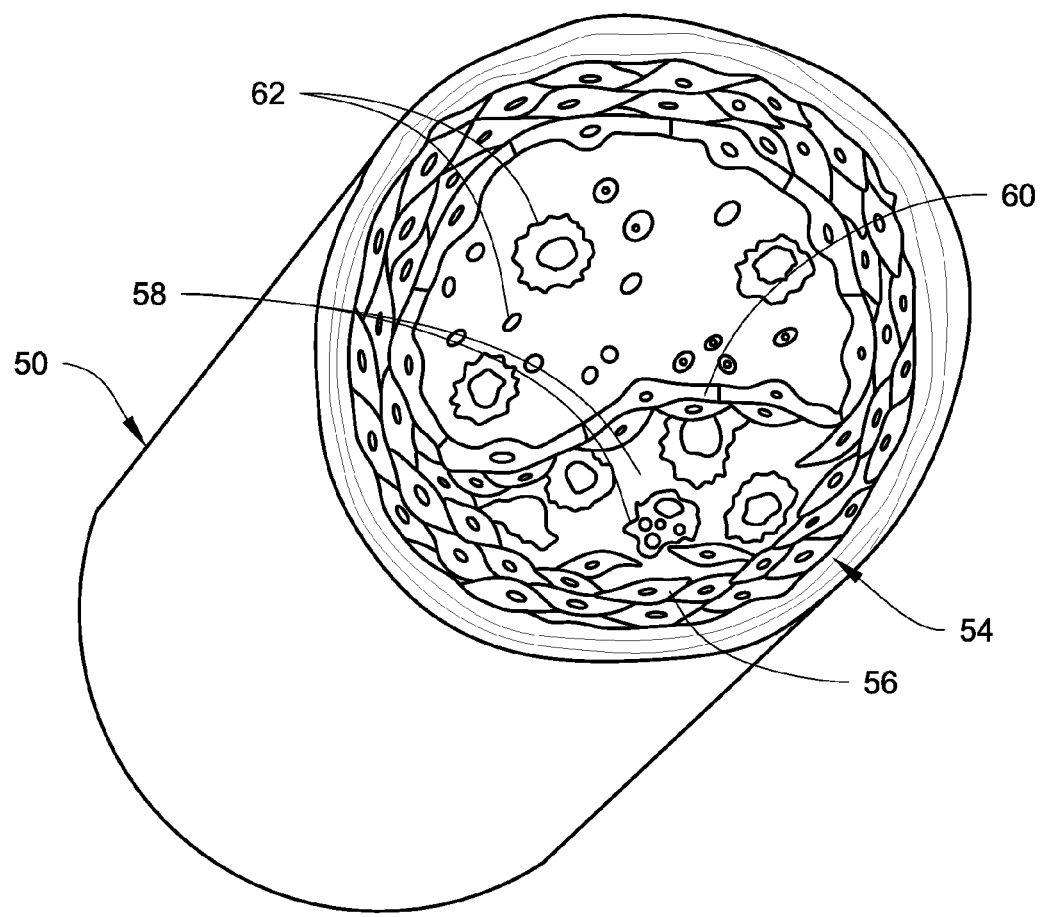
FIG. 4A is an illustration of a vessel for which the therapy system of FIG. 1 may be used.

For example, ultrasound therapy as described herein may be used to treat one or more regions of the vasculature. An exemplary diagram of a blood vessel 50 is shown in FIG. 4A to facilitate discussion of the use of therapy described herein. The blood vessel 50 shown in FIG. 4A includes a vessel wall 52 having a plaque structure 54 formed on the interior of the vessel wall 52. The plaque architecture of the structure 54 may include, for example, a plaque base 56, a lipid core 58, and a fibrous or calcified cap 60. Blood 62 flows through the blood vessel 50 defined by the vessel wall 52.

One or more embodiments of methods and/or systems described herein may use imaging to identify one or more locations of the vascular structure, e.g., structural characteristics associated with the blood vessel 50, such as boundaries of the vessel wall (e.g., outer and inner boundaries, such as in a coordinate system), thickness of the vessel wall, measurement of tissue properties within the vessel wall (e.g., stiffness of tissue, such as, for example, it relates to a diseased state), differentiation of plaque from vessel wall, differentiation of the various components of plaque (e.g., differentiation of base from lipid core, differentiation of base from fibrous cap, differentiation of lipid core from fibrous cap, etc.), etc. For example, in one or more embodiments, upon differentiation of the base from the fibrous cap of the plaque architecture, the therapy system 10 may deliver controlled therapy as described herein to ablate the base to reduce further plaque buildup or growth or provide treatment according to PCT International Publication No. WO2009/002492.

Similar processes as described with reference to vascular structure may be used for other conditions described herein to be treated (e.g., cardiac conditions, nerve therapy, ablation therapy, etc.).

In one or more embodiments, the therapy system 10 is configured for both imaging and therapy. Imaging can be used to continuously monitor the tissue response to sub-therapeutic and therapeutic high intensity focused ultra-sound (HIFU) beams with very high spatial and temporal resolutions. Imaging and therapy are fully integrated allowing for continuous adjustment of the therapeutic beam to achieve the treatment objectives (e.g., continual adjustment of therapy signals to the array of transducer elements 22 to adjust the therapy beam). Multiple real-time imaging modes (e.g., SA imaging or B-mode imaging, SFT imaging, M2D-mode strain imaging, QB-mode imaging, etc.) can be used to: 1) guide the therapeutic beam, 2) assess, for example, thermal and mechanical tissue response to estimate the initial dose, 3) monitor and characterize tissue response during therapy, and 4) assess the state of the treated tissue at the completion of each exposure (e.g., for use in defining subsequent therapy exposures).

Real-time intensity modulation (or generally beam resynthesis; including adjustment of phase/dealy, amplitude, and/or spectral content of the therapeutic beam) can be performed based on imaging feedback with millisecond time resolution. One example of the therapy system 10, having a dual mode ultrasound transducer (DMUT) array 22, can be used to produce controlled lesion formation at the intended target location and minimize or eliminate irreversible (collateral) damage to the surrounding and intervening tissue in the path of the HIFU beam.

Other therapy that may be provided by the exemplary therapy system 10 (e.g., using delivery of a plurality of sequential therapy bursts) may include use for cancer treatment (including prostate, hepatic cellular carcinoma, kidney, breast, brain, etc.), cardiac ablation (including catheter-based or transthoracic), vascular treatment (including thrombolysis or vascular occlusion), and controlled drug activation/delivery.

Different damage zones within HIFU-induced lesions can be identified and attributed to a mixture of thermal and mechanical effects of the tissue response to therapeutic HIFU exposures. Cavitation may cause different types of tissue damage (e.g. enhancing thermal damage, mechanical tissue erosion). However, the dynamics of the lesion formation process in tissue media can be reliably captured by noninvasive imaging techniques, including diagnostic ultrasound. The DMUA concept, together with, for example, real-time data collection, beamforming, and pre- and post-beamforming signal processing allow for the interrogation of the tissue response exactly at the location of assumed lesion formation. DMUA can be used for imaging to allow for assessing changes in tissue after lesion formation. The therapy system 10, in one or more embodiments, allows for characterizing the dynamics in tissue response at regular intervals during lesion formation (e.g., down to sub-millisecond) and allows for resynthesis of the therapeutic HIFU beam(s) based on this feedback. The therapy system 10 provides a closed loop, or feedback, controlled therapy process, e.g., such as for lesion formation (e.g., different from open-loop types (such as single-shot level, typical exposure duration 2-5 seconds)). The therapy system 10 allows for real-time control of the exposure in both space and time based on tissue response at the target locations with high resolution.

The DMUA approach is advantageous, in part, because of the inherent registration between the imaging and therapeutic coordinate systems. This permits: 1) motion tracking to maintain the therapeutic application at the target point; 2) in situ estimation of the dose based on target tissue response to sub-therapeutic HIFU beams; 3) monitoring tissue response to HIFU beams with sub-millisecond resolution and adjust the exposure parameters to promote the desired damage mechanism (e.g., based on such monitoring); and 4) assess irreversible tissue damage by imaging tissue response to sub-therapeutic HIFU beams after lesion formation.

As used herein, therapeutic beams (e.g., such beams being formed of or including bursts, pulses, etc.) are beams used to provide therapy to a patient (e.g., having characteristics and defined by therapy parameters for providing such therapy). On the other hand, sub-therapeutic beams (e.g., having diagnostic like characteristics; for use in diagnostic imaging) have characteristics relative to the therapy being provided by the therapeutic beams that are not at the therapeutic level. For example, therapeutic beams may have characteristics sufficient for ablation, wherein sub-therapeutic beams may have characteristics below those used for ablation but sufficient for performing a different function such as imaging.

For example, assuming a 1-second therapy beam can generate a thermal lesion at intensity $I_0$, then a beam with the same duration and spatial pattern, but with focal intensity $I_0/20$ is likely to cause temperature change at the focus by a few degrees C. This is a reversible change and is unlikely to cause any permanent lesion. Consequently, this beam is considered sub-therapeutic. This sub-therapeutic beam can serve as a test beam for measuring local thermal response for purposes of calibrating the therapy exposure in situ. Likewise, a beam (e.g., for use in cavitation therapy) with the same focal intensity, but with a duration in the 10 microseconds to less than milliseconds (e.g., sub-milliseconds) will not form thermal lesions, but can serve as a test sub-therapeutic beam for cavitation activity.

Figure 5:
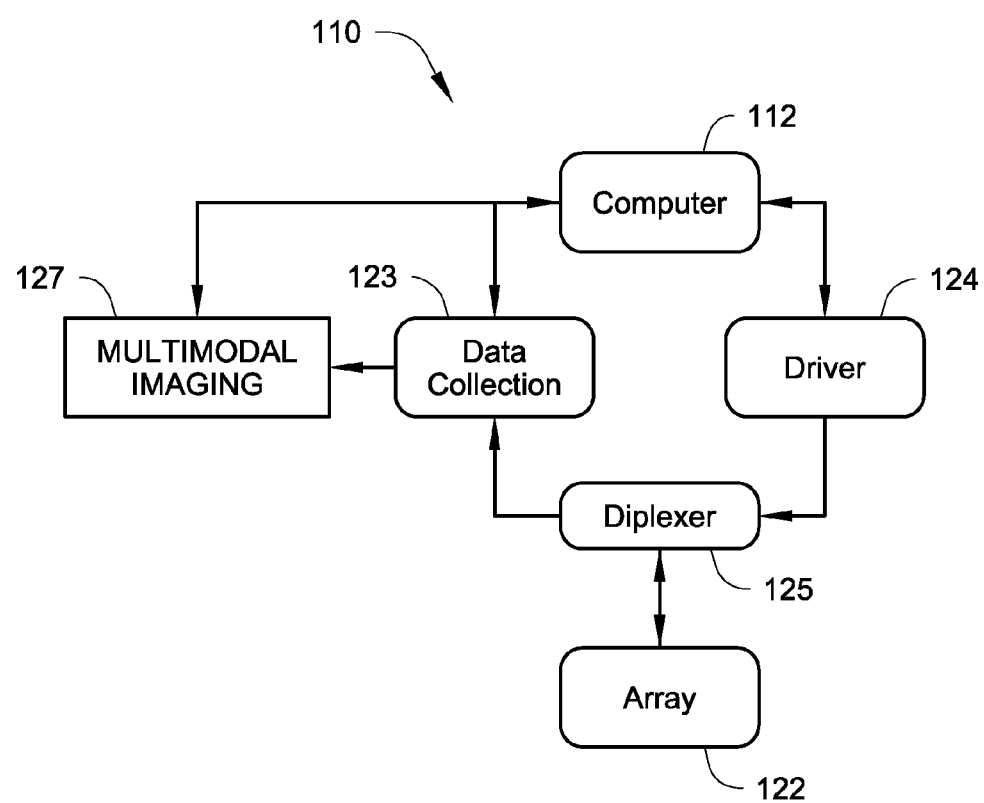
FIG. 5 is a block diagram of one exemplary embodiment of a therapy system shown generally in FIG. 1.

FIG. 5 illustrates a block diagram of one exemplary implementation of therapy system 10 which uses a dual mode ultrasound array (DMUA) for providing therapy; as well as for use in control of such therapy using imaging by way thereof. The therapy system 110, as shown in FIG. 5, includes dual mode ultrasound array (DMUA) 122, computer 112 (e.g., control apparatus such as that generally shown and described with reference to FIG. 1), multi-modal imaging 127, data collection 123 (e.g., signal acquisition), driver 124 (e.g., DMUA driver), and diplexer apparatus 125 (e.g., a configurable diplexer; such as a diplexer for each control channel associated with each transducer element of the array 122).

In one or more embodiments, the dual mode ultrasound array (DMUA) 122 is a therapeutic device capable of both delivering high intensity focused ultrasound (HIFU) and imaging with the same plurality of transducer elements. This configuration provides inherent registration between the ultrasound imaging coordinates and the therapeutic coordinates, allowing the user to deliver HIFU energy to a target by simply pointing and clicking on an ultrasound image formed from pulse-echo data obtained using the DMUA elements. The ultrasound transducer array 122 may be any apparatus (e.g., transmitting, receiving components, etc.) capable of delivering therapeutic and sub-therapeutic ultrasound pulses and sampling/collecting ultrasound echo energy contemplated to be used in ultrasound imaging systems and/or therapy systems. As used herein, such transducers may include a transmitting portion, e.g., to deliver pulse energy, and a receiving portion, e.g., to sample/collect echo or reflected energy, which may or may not be the same portion. During the ultrasound imaging of a target (e.g., a tumor, a vessel, etc.), the transducer array 122 may be positioned relative to the target so as to be capable of delivering energy to the target resulting in reflected energy (also known as the resultant pulse-echo or echo energy) and also sampling the echo energy. Further, the transducer elements of array 122 must be able to deliver therapeutic bursts (e.g., forming and delivering a therapeutic beam of ultrasonic energy over time).

In one of more embodiments, the dual mode ultrasound array 122 is an array with as low as 32 transducer elements (e.g., each drivable through a separate control channel in one or more therapeutic modes and in one or more imaging modes). The number of elements, the DMUA geometry (e.g., typically concave, but which may be of any other suitable geometry) and the element distribution is determined by the nature of the target (e.g. depth and size) and the presence of obstacles in the path of the therapeutic beam (e.g., the rib cage). Once a DMUA is designed, it is characterized by the DMUA's therapeutic operating field (ThxOF) and DMUA's imaging field of view (IxFOV). For example, a 32-element DMUA operating at 3.5 MHz designed for the treatment of peripheral vascular disease may have an elliptically shaped ThxOF around its geometric center extending by 1.6 cm axially and 0.8 cm laterally. The DMUA's IxFOV may be nearly twice the size of the DMUA's ThxOF. Further, for example, in Ebbini et al (Ultrasonic Imaging, 2006), another DMUA prototype operating at 1 MHz is described with potential use for the treatment of breast cancer (e.g., also well suited for thrombolysis). This 64-element, concave array has an elliptically shaped ThxOF with dimensions 5 cm axially and 3 laterally with an IxFOV roughly twice that size.

In one or more embodiments, various arrays may have one or more benefits over others. For example, in one or more embodiments, the transducer array may be a segmented concave transducer with multiple sub-apertures to insonify the target region from multiple angles. At least one sub-aperture may be used in linear array or phased array mode for initial B-mode or SA imaging of the target (e.g. vessel). The driver of the transducer may be designed to drive the multiple sub-apertures with independent codes. Each sub-aperture may be a one-dimensional or two-dimensional array.

For example, various arrays and operation thereof, are described in Ebbini, et al., "Dual-Mode Ultrasound Phased Arrays for Image-Guided Surgery," *Ultrasound Imaging*, vol. 28, pp. 65-82 (2006); and Wan et al., "Imaging with Concave Large-Aperture Therapeutic Ultrasound Arrays Using Conventional Synthetic-Aperture Beamforming," *IEEE Transactions on Ultrasound, Ferroelectrics, and Frequency Control*, vol. 55, no. 8, pp. 1705-1718 (August 2008), which are all hereby incorporated by reference herein.

Therapeutic arrays (e.g., dual mode ultrasound array 122) are typically concave with low $f_{number}$ to provide geometric focusing gain on the order of 1000 or more. A properly designed therapeutic phased array is defined by its therapeutic operating field (ThxOF) (see, Ebbini et al. (2006)). The ThxOF is the volume around the geometric center where the focusing gain of the array (e.g., for an electronically steered focus) does not fall by more than 3 dB. At least in one embodiment, an effective array design balances the need for efficiency (which typically calls for larger elements) with the need for sufficiently large ThxOF (which typically calls for smaller elements). This is also governed by other factors like the aperture size, operating frequency, cross coupling characteristics of the transducer, etc. Power efficiency considerations almost surely dictate element dimensions in the $1.5\lambda$-$3\lambda$ range, where $\lambda$ is the wavelength. This coarse sampling of the array aperture is the cause of the grating lobe phenomenon. Grating lobes could potentially create hot spots away from the intended target location.

Using piezo-composite or other transducer technology, concave apertures with $f_{number}$ values <1 may be formed. Furthermore, the array elements may be defined by electrode patterning and can be defined on a regular lattice or randomly. Surface intensity levels in the range 5-10 W/cm$^2$ or more may be achieved allowing for focal intensity levels in the range of 5-25 kW/cm$^2$ or more. With such intensity levels, one can design treatment protocols to produce irreversible damage within small volumes around the focal spot while sparing the intervening tissue in the path of the therapeutic HIFU beam. The damage could be thermal or mechanical or a mixture of the two, depending on the involvement of cavitation and/or tissue boiling within the treatment volume.

When performing therapy using such an array of transducer elements, various factors can affect the threshold for the initiation of the cavitation events, especially in vivo. These include tissue attenuation which determines the in situ intensity, cellular architecture, vascularization, etc. Even if it is possible to determine the intensity level suitable for the initiation of a cavitation event, it may be hard to maintain the cavitation activity at a level where it is enhancing. Further, undesirable formation of cavitation clouds at locations other than the intended target could lead to collateral damage to these tissues.

HIFU (e.g., delivered using the system 110) is intended to be used in noninvasive mode, or at least in a minimally invasive mode. Feedback, therefore, must be noninvasive or minimally invasive to match the nature of the therapeutic applicator.

MRI and US diagnostic imaging systems have been used in combination with HIFU, and in view of the advent of MRI and US thermography (MRT and UST), treatment feedback control based on noninvasive thermography may be used. With respect to both MRT and UST, however, certain challenges need to be overcome to produce robust images of temperature change in moving organs. Tissue motion and deformation is especially problematic for MRT due to the relatively low frame rates. UST has important limitations due to tissue heterogeneity and the possible lack of tracking at temperatures greater than 55° C.

Spatial and temporal registration between the HIFU source and the image-guidance system is necessary for robust feedback control based on UST or MRT. This can be accomplished by careful mounting of the HIFU transducer so that the therapeutic coordinates are related by a known transformation. In addition, triggering of the HIFU source based image frame (or line) allows for capture of important events resulting from the application of the HIFU source. In this regard, MRI and US have particular limitations that may result in one or more sources of failure (e.g., the small HIFU focus is not fully captured by the imaging system). For example, often times the HIFU focus is a sub-voxel of the MRI guidance system. The imaging slice of a 2D ultrasound image guidance system, on the other hand, may not be aligned with the therapeutic volume due to different distortions experienced by the therapeutic and diagnostic beams, even when they are spatially registered. In such a case, the image guidance system may fail to provide the necessary feedback to guarantee that the therapeutic end point of a HIFU shot is reached.

Further, an undesired event (e.g. excessive heating or cavitation) may occur outside the target region. Even if the image guidance system captures such an event, a transformation between the imaging and therapeutic coordinate systems is necessary to allow for beam resynthesis. In the case of MRI guidance, the frame time may be too slow to capture these events before they are fully developed, especially when short HIFU shots are being used (e.g., which may result in abandoning the particular HIFU shot or treatment). In this case, the image guidance system fails to assure the safety of the procedure and/or minimization or elimination of collateral damage.

The therapy system 110 using the DMUA 122 addresses both sources of failure in providing a way to continuously monitor the tissue response to the application of the HIFU beam throughout the volume of interaction with tissue. In one or more embodiments, this continuous monitoring, together with the availability of real-time signal processing and beam resynthesis with millisecond resolution allows for treatment protocols as may be characterized herein. For example, exquisite control of lesion formation at the single-shot level may be performed so that the therapeutic end point of every HIFU shot is achieved without excessive damage, e.g. achieve thermal coagulation without tissue boiling or violent cavitation events. For example, for cavitation based treatments (e.g., thermal treatments, such as ablation), the DMUA can be used to localize the individual cavitation events within and around the HIFU focus and can be used to make immediate corrections to maintain the cavitation activity at the desired level and only within the target volume.

Further, for example, any undesired event anywhere within the HIFU beam (e.g., cavitation or excessive heating) may be detected and localized. This may allow for safety enhancement (e.g., less harm or damage) throughout the treatment volume. Furthermore, the detection and localization of these events may lead to automatic correction by beam resynthesis to allow the treatment to continue. For example, early detection and localization of a hot spot outside the target may lead to a refocused beam that minimizes the HIFU energy at the hot spot while maintaining the proper exposure to the target. The inherent registration between the therapeutic and imaging coordinate systems allows for the resynthesis of the HIFU beam without latency so that the desired exposure at the target is achieved without interruption while the collateral damage to the intervening and surrounding tissue is being avoided.

Figure 4B:
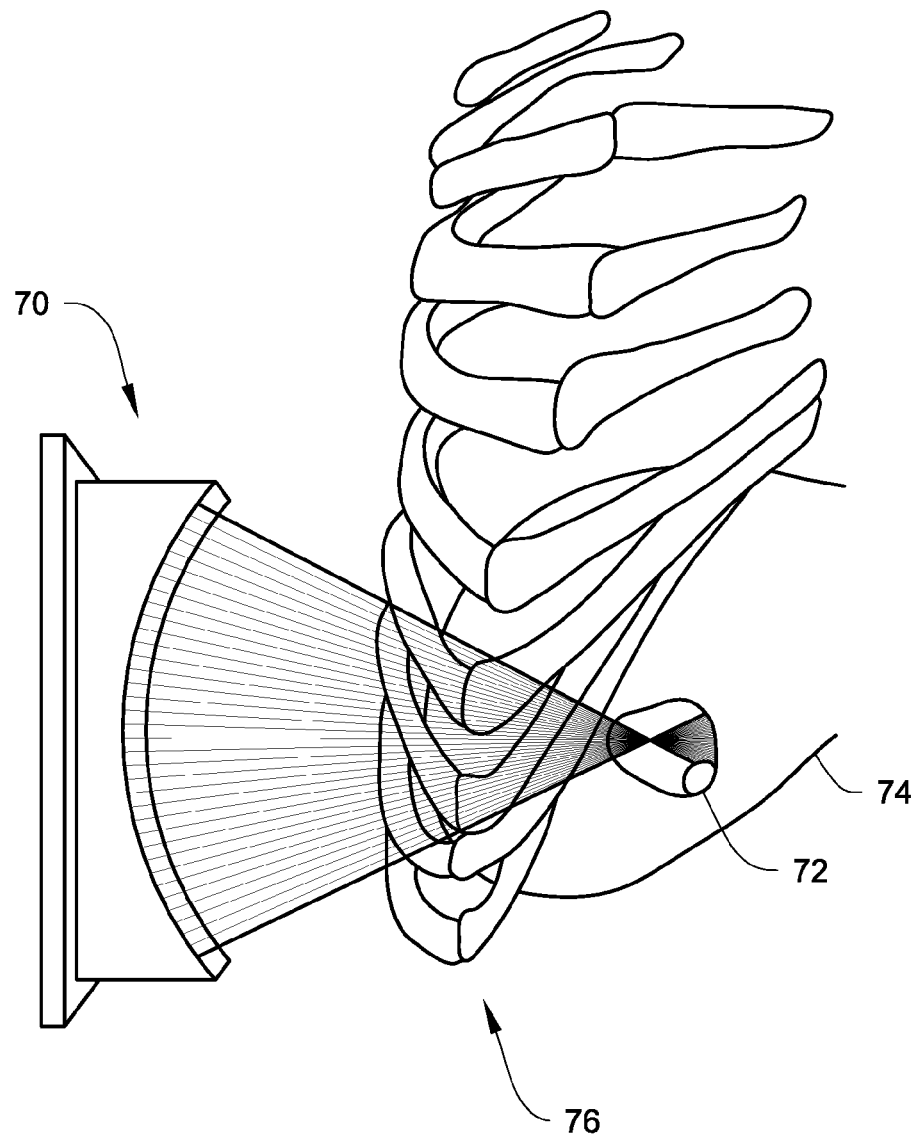
FIG. 4B is an illustration of a tumor for which the therapy system of FIG. 1 may be used.
Figure 6D:
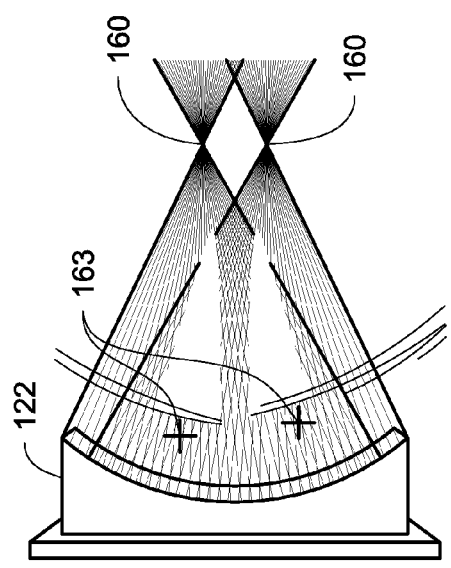
FIG. 6A-6D provides exemplary images illustrating delivery of therapy.
Figure 6B:
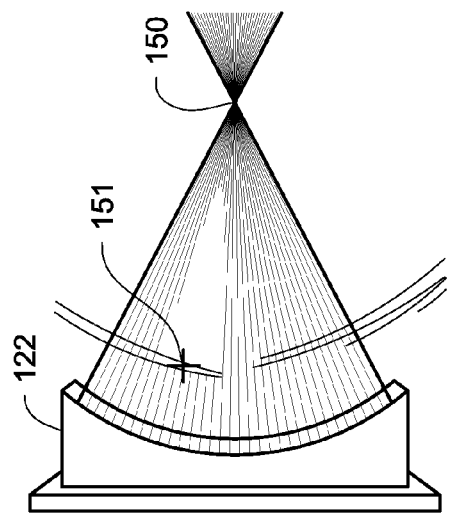
Figure 6C:
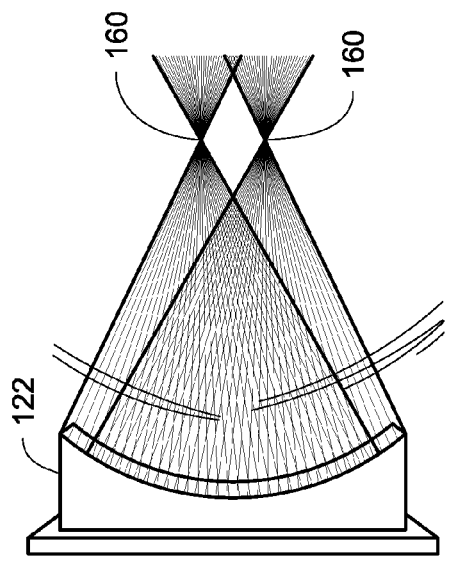
Figure 6A:
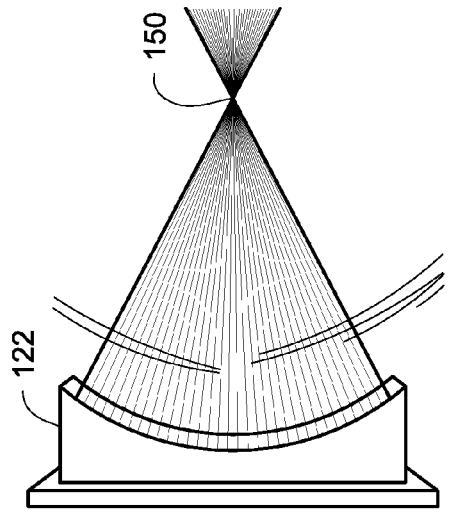

For example, FIGS. 6A-6D show the ability to refocus a therapeutic beam about critical points identified on intervening tissue (e.g., a rib in the path of the therapeutic beam delivered to a target location as shown in FIG. 4B). For example, FIG. 4B shows an illustration of a focused beam from an array 70 targeting a tumor 72 in the liver 74. The focused beam is distorted due to the heterogeneities of the rib cage 76 (e.g., which may cause undesirable heating across the ribs). FIG. 6A shows a simulated single focus pattern at a target point (e.g., a portion of a liver tumor) from a DMUA 122. In the image of FIG. 6B, a critical point 151 may be identified (e.g., portion of a rib) that represents intervening tissue in the treatment region between the DMUA and the target 150. As shown in FIG. 6B, the same focal target point 150 is achieved with a beam that is refocused around the critical point 151 (e.g., a point which is not to be heat). FIG. 6C shows multiple focal fields providing a therapeutic beam at two focal target points 160, and FIG. 6D shows two critical points 163 which may be identified (e.g., portions of a rib) that represent intervening tissue between the DMUA and the target 160. As shown in FIG. 6D, the same focal target points 160 are achieved with a beam that is refocused around the critical points 163.

In one or more embodiments, the therapy system 110, as described herein, allows for high-specificity imaging of tissue response to sub-therapeutic and therapeutic HIFU exposure throughout the treatment volume. One or more of the following features may enable the therapy system 110. For example, optimal and robust beam synthesis processes or methods allowing for exquisite control over the HIFU beams in space and time may be used. Not only may this provide for control of the therapeutic beams spatially using phased array concepts, but it may also be able to achieve temporal control at the pulse level as well as intensity modulation. Further, for example, imaging and signal processing algorithms using DMUAs providing imaging feedback for refocusing or resynthesis of the therapeutic HIFU beam may be used to achieve the treatment objective while minimizing or eliminating collateral damage.

Still further, hardware and software platforms that allow for real-time image formation and signal processing of DMUA echo data for characterization of the tissue response to HIFU exposure may be used. For example, real-time refocusing/resynthesis based on user-defined control points using real-time imaging feedback with millisecond latency may be implemented. This may be enhanced by the use of multi-channel drivers with real-time arbitrary waveform generation on different DMUA channels.

Further, for example, various imaging modes may be used to further improve the specificity of the DMUA imaging to HIFU-tissue interactions, both at the therapeutic and subtherapeutic levels. For example, such imaging modes may be designed to capture the thermal, viscoelastic, and non-linear response to HIFU beams, especially in the sub-therapeutic range. In addition, imaging modes for estimation of cavitation threshold and tissue absorption in situ may be used (see, FIG. 11).

Conventional imaging with DMUAs has been addressed and, despite limitations, DMUAs form pulse-echo ultrasound images with speckle patterns consistent with their fractional bandwidths and $f_{number}$ values (see, Wan and Ebbini (2008)). Furthermore, for a given DMUA configuration (e.g., radius of curvature and $f_{number}$, element size and spacing, operating frequency and fractional bandwidth, etc.), the DMUA has an imaging field of view ($I_xFOV$) that covers and extends beyond its ThxOF. The IxFOV can be extended further by accounting for the array focusing gain. Furthermore, the speckle characteristics of DMUAs can be improved by applying inverse filtering techniques. DMUA pulse-echo data has the characteristics of pulse-echo data from any other imaging array, but reflects the typically lower frequency and lower fractional bandwidth, the low $f_{number}$ of the array, the relatively large element dimensions, etc. Therefore, the quality of DMUA images can be improved by the use of signal processing and reconstructive imaging. Furthermore, despite the limited fractional bandwidth, coded excitation may be used to improve the signal to noise and spatial resolution of a DMUA.

Further, multi-modal coded excitation imaging algorithms for DMUAs may be used to enhance their resolution and signal to noise in a region of interest together with improving the frame rates. Multi-modal coded excitation will also improve the rejection of interference from the intermittent HIFU pulses and reduce reverberation artifacts from the concave transducer and the water bolus. Multi-modal coded excitation, therefore, may be one of the features used for optimal imaging with DMUAs. Such coded excitation may provide capabilities for mitigating the limitations imposed by the geometric design considerations of therapeutic arrays and typical patient setup; and also may improve the frame rate and allow for 2D (or 3D) motion tracking capabilities (e.g., which may enhance image guidance).

Further, multi-modal coded excitation may be beneficial for improving the focusing efficiency at the desired target location (or locations when multiple-focusing is used). A broadband waveform can be synthesized at the target location where its frequency components add up coherently within a pillbox (e.g., target) with dimensions determined by the coherence length (inverse of the bandwidth) and shaped by the focusing aperture. Outside this volume, wavelets from individual elements may add up almost incoherently when the elements are sufficiently separated in space. This results in array focusing gains much larger than their single-frequency counterparts.

For example, one or more illustrative examples of coded excitation ultrasound which may be used in combination with the imaging method and/or systems described herein are provided in Shen et al., "A New Coded-Excitation Ultrasound Imaging System—Part I: Basic Principles," *IEEE Transactions on Ultrasonics, Ferroelectrics, and Frequency Control*, vol. 43, no. 1, pp. 131-140, January 1996); Shen et al., "A New Coded-Excitation Ultrasound Imaging System—Part II: Operator Design," *IEEE Transactions on Ultrasonics, Ferroelectrics, and Frequency Control*, vol. 43, no. 1, pp. 141-148, January 1996); and Shen et al., "Filter-Based Coded-Excitation System for High-Speed Ultrasound Imaging," *IEEE Transactions on Medical Imaging*, vol. 17, no. 6, pp. 923-934, December 1998), which are all incorporated herein by reference.

Figure 7A:
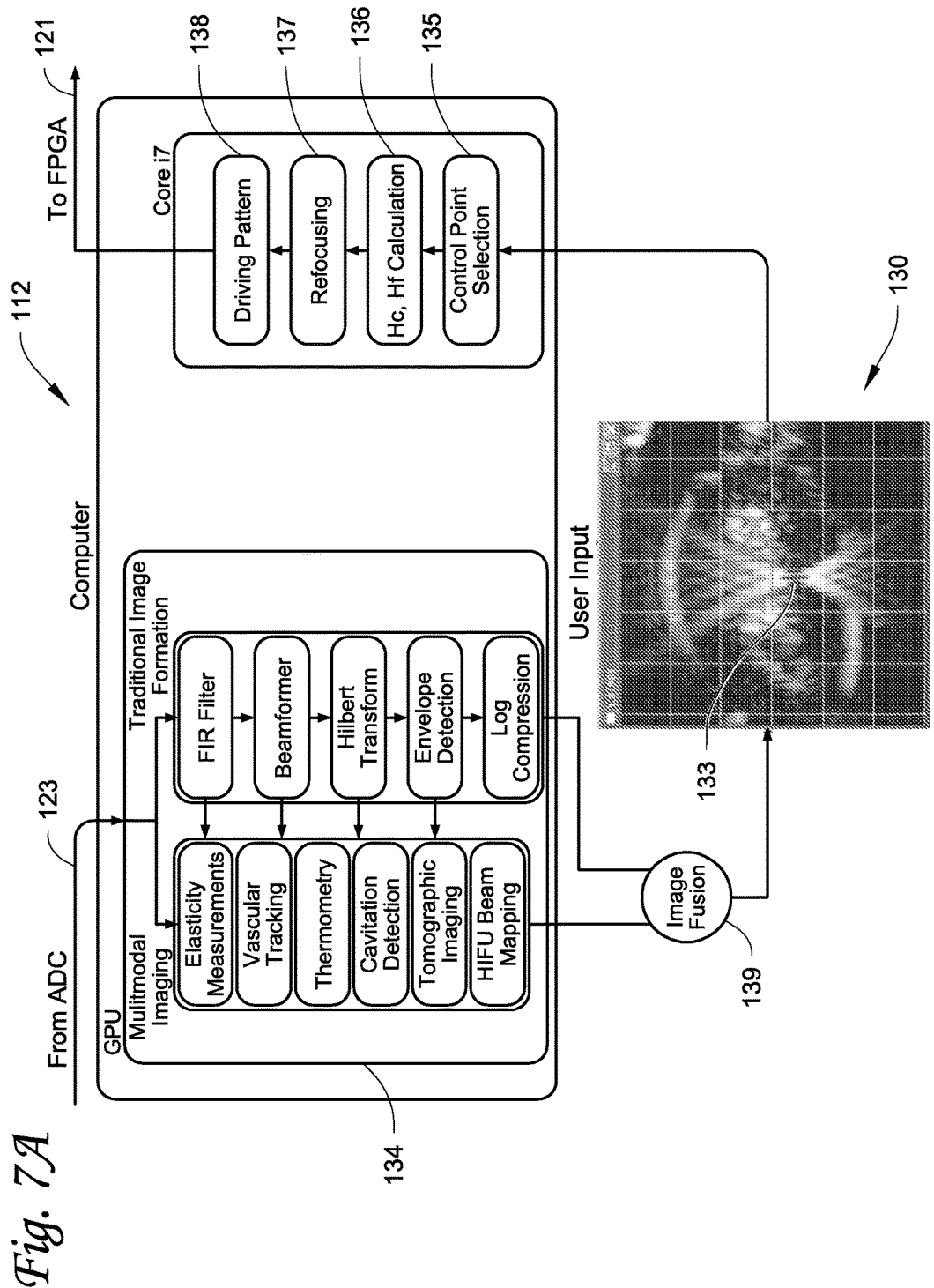
FIGS. 7A-7J are block diagrams of exemplary embodiments of components usable in the therapy system shown in FIG. 5.
Figure 12A:
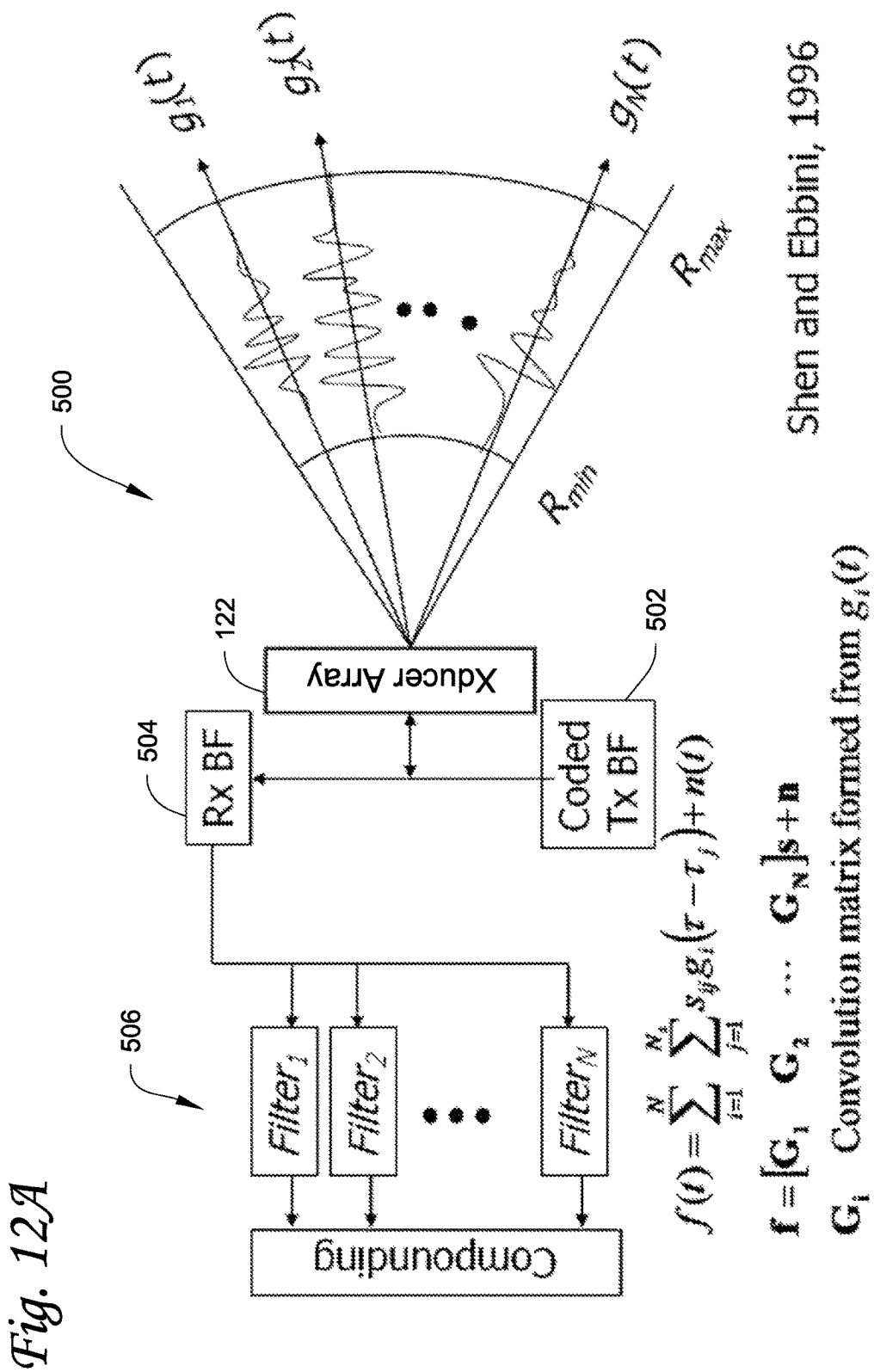
FIGS. 12A-12B show a block diagram and a signal image for use in illustrating the use of coded excitation in providing imaging and delivery of therapy.

For example, FIG. 7A, which may include a driver 170, shows a configuration of at least a portion of an ultrasound system with arbitrary waveform generation suitable for multi-modal coded excitation (e.g., the operation 500 of such multi-modal coded excitation shown generally by components 500 is illustrated in FIG. 12A). The term multi-modal coded excitation system refers to one capable of producing transmit patterns where different points/directions in the target region see different waveforms (e.g. $g_1(t)$, $g_2(t)$, ... $g_N(t)$ in the FIG. 12A). These waveforms may be designed to be largely orthogonal to each other. In general, for example, depending on the geometry of the transmitting array 122, the number of elements, and the depth of the waveform memory, coded transmit beamforming 502 (e.g., Coded Tx BF in the FIG. 12A) can be used to generate multiple focal points where the spatial-peak, temporal-average intensity ($I_{SPTA}$) is sufficient to produce thermal effects. For example, this may be implemented by the selection of the driving waveforms in memory and conventional multiple-focus synthesis as described in Ebbini and Cain, "Multiple-focus ultrasound phased array pattern synthesis—Optimal driving signal distributions for hyperthermia," IEEE TRANSACTIONS ON ULTRASONICS FERROELECTRICS AND FREQUENCY CONTROL, vol. 36, no. 5, pp. 540-548, (September 1989). Further, as described therein, receive beamforming 504 (e.g., Rx BF in FIG. 12A), along with filtering and compounding operations 506, can be used to analyze the return pulse-echo data as is known by one skilled in the art.

The focusing and the pulse repetition frequency (PRF) of the transmit pattern allow for control of the $I_{SPTA}$ at the desired target points to produce thermal effects. Similarly, the $I_{SPTA}$ can be designed to be minimized at the critical points (e.g., in a manner like described with reference to FIGS. 8A and 8B). Non-thermal therapeutic effects can be achieved by synthesizing transmit patterns with spatial-peak, temporal-peak intensity ($I_{SPTP}$) levels at the target points to maximize cavitational or shearwave generation with minimal heating. In one or more embodiments, one advantage of using arbitrary waveform generation and coded excitation in synthesizing therapeutic array patterns is that interference patterns outside the target points have $I_{SPTA}$ and $I_{SPTP}$ levels that can be much lower than their conventional counterparts (e.g., interference patterns resulting from continuous wave or conventional pulse wave excitation).

The therapy system 110 may allow for the use of coded excitation in therapeutic mode as well as in imaging mode. For example, two implementations of coded-excitation drivers may be used, one supporting binary waveforms (codes) suitable for driving push-pull amplifiers as was described in Ebbini and Cain, "Experimental evaluation of a prototype cylindrical section ultrasound hyperthermia phased-array applicator," IEEE TRANSACTIONS ON ULTRASONICS FERROELECTRICS AND FREQUENCY CONTROL, vol. 38, no. 5, pp. 510-520, September 1991. FIG. 7D shows another implementation of the digital driver that may be used for coded excitation. Another implementation may employ multi-level memory and digital-to-analog (D/A) conversion suitable for driving linear amplifiers as shown, for example, in FIG. 7E. This driver system 170 of FIG. 7E also supports CW excitation through the use of direct digital synthesis (DDS) available on most FPGAs.

Figure 12B:
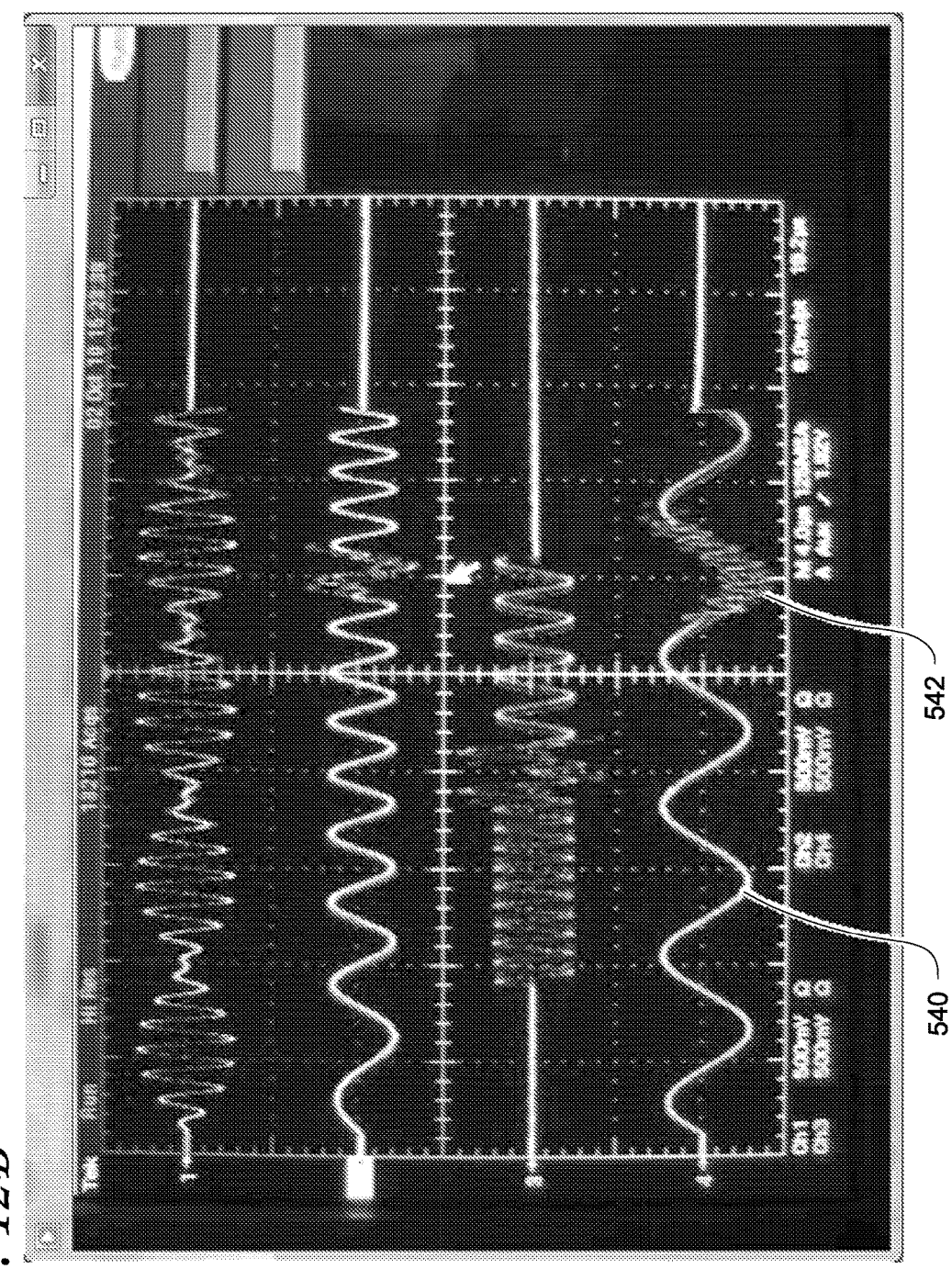

With use and implementation of multi-modal coded excitation, frame rates in the range of 10,000 frames per second (fps) may be obtained. Furthermore, therapy and imaging pulses can be brought together to the point of overlap, maximizing treatment efficiency by maximizing the therapeutic signal levels at the target point(s) while minimizing the interference elsewhere. With the use of arbitrary waveform generation, it is possible to completely overlap the imaging and therapeutic operation by designing therapy/imaging waveforms where the imaging pulse is riding on the therapy waveform as illustrated in FIG. 12B. FIG. 12B (i.e., a screen capture of actual waveforms generated by an implemented driver) illustrates how small-signal waveforms (e.g. imaging) can ride on longer duration, large-signal therapy waveforms. For example, an imaging waveform 542 may ride on the therapy waveform 540 to cause resulting pulse-echo data. This waveform generation capability, together with configurable receive circuitry as illustrated by the circuit shown in FIG. 7I, allow for nearly continuous image acquisition, even while the therapy pulse is being applied. Parallel processing of the received echoes (as illustrated in FIG. 12A) using filter banks 506 and post receive beamforming 504 (e.g., Rx BF in FIG. 12A) allows for truly multi-modal imaging using ultrasound. For example, grayscale images, strain images, flow images, and QB-mode images can be processed simultaneously and fused (or compounded) to provide the physician with a full view of what happens during the treatment.

High frame rate DMUA imaging may allow for the reliable estimation of tissue motion and deformation through speckle tracking and similar methods. This may also allow for the measurement of 2D or 3D flow. As such, this may provide a reliable approach to estimate the localized tissue response to the HIFU beam, even when delivered sub-therapeutically. Similarly, being able to acquire more frames during silence intervals will allow for more robust detection of abnormal events during lesion formation. Coupled with the ability to resynthesize the beam, a closed loop control may be provided (e.g., to perform lesion formation).

With further reference to FIG. 5, the computer 112 (e.g., control apparatus) may serve as a platform for a wide array of real-time signal processing operations; the computer 112 may control multimodal analysis of image data to expand on conventional imaging to expose tissue dynamics as they happen; and the computer may be configured to present results to a user in real-time, allowing for instant feedback and control.

For example, FIG. 7A shows one embodiment of a computer 112 (e.g., control apparatus) including a user interface 130 (simplified as only a display but which may include any input apparatus for allowing user input). The user interface 130 shows an image of a treatment region (e.g., a region in which a user may select one or more target points or critical points as described herein), however, other input mechanisms may be used to, for example, abandon therapy, modify therapy, etc. As shown in FIG. 7A, the computer 112 is provided with data from data collection 123 (e.g., image data from an analog to digital converter) and provides an output to driver 121 (e.g., configured as a FPGA for receiving therapy signals and imaging signals to drive the array 122).

The computer 112 may include multiple CPUs and GPUs for processing data to control therapy using feedback generated using image data (e.g., SA image data, STF image data, multi-modal image data, etc.). GPU and Core i7 represent specific processors configured to execute the instructions for carrying out functionality as described herein. For example, multi-modal imaging 127 is illustrated as part of the computer 112 and can include a variety of data and signals drawn from traditional image formation, such as shown in FIG. 7A. This can include a bandpass filter, a module to provide SA Beamforming (e.g., serial excitation of sensor elements and detection by non-excited elements), a module to provide STF Beamforming, a Hilbert Transform module, an envelope detection and log compression modules. Each of these modules can provide data for use by the multi-modal imaging module for use in analyzing the image data and providing therapy. For example, the multi-modal imaging module can be configured to perform one or more different imaging analysis such as shown in FIG. 7A, including, but not limited to elasticity measurements (e.g., track movement and evaluate tissue stiffness or other tissue parameter, for example, thermal data due to tissue subjected to heat from an ultrasonic source exhibiting a stiffness that differs from that of un-treated tissue), vascular tracking (e.g., tracking motion for use in identifying structure to be treated), thermometry (e.g., generate thermal response data for controlling therapy), cavitation detection (e.g., to generate data indicative of cavitation, such as bubbles, for use in controlling therapy), tomographic imaging (e.g., to image using reconstruction techniques for identifying targets or use in controlling therapy), HIFU beam mapping (e.g., to control beam refocusing), etc. User input through user interface 130 can include decision making by the user and user control. The image in FIG. 7A may depict a body part (e.g., a kidney) and ultrasonic energy delivered at a target site 133 located slightly below and to the left of the geometric center of the image.

On the CPU side, data can be come from a network stack (e.g., experimental mode, where data is streamlined from SonixRP scanner) or data file (e.g., review mode). The processed result can be visualized with a designed UT system (OpenGL based) or exposed to other commercial software for further analysis (e.g., Matlab). The CPU result can be used to provide feedback control of the therapeutic beam. For example, upon selection of control points 135, calculations may be carried out to generate therapy signals for communication to driver 121. For example, calculations 136 may be carried out to define a therapy burst to be delivered, the calculated result may be used to generate refocusing of the therapy beam 137, and a driving pattern 138 (e.g., therapy signals) may be generated for communication to driver 121.

Still further different modes of imaging may be fused 139 to provide the user with desirable imaging of the therapy being carried out. For example, SA image data may be fused with STF image data and be displayed. Further, for example, more detail information (e.g., using M2D imaging) regarding structures (e.g., vasculature, including plaque structures) may be provided to be fused with other data, such as STF or SA image data.

Figure 7B:
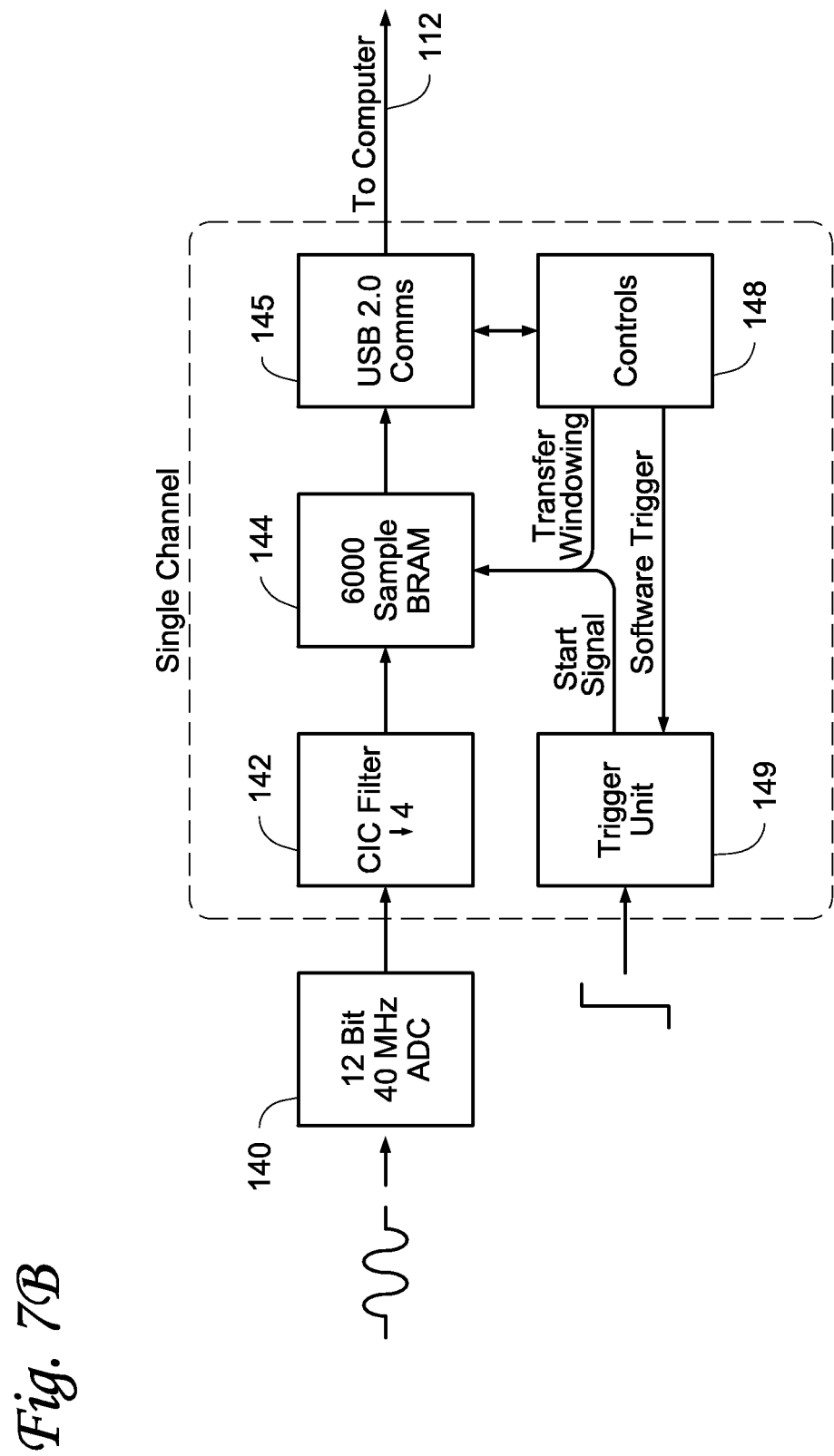
Figure 7C:
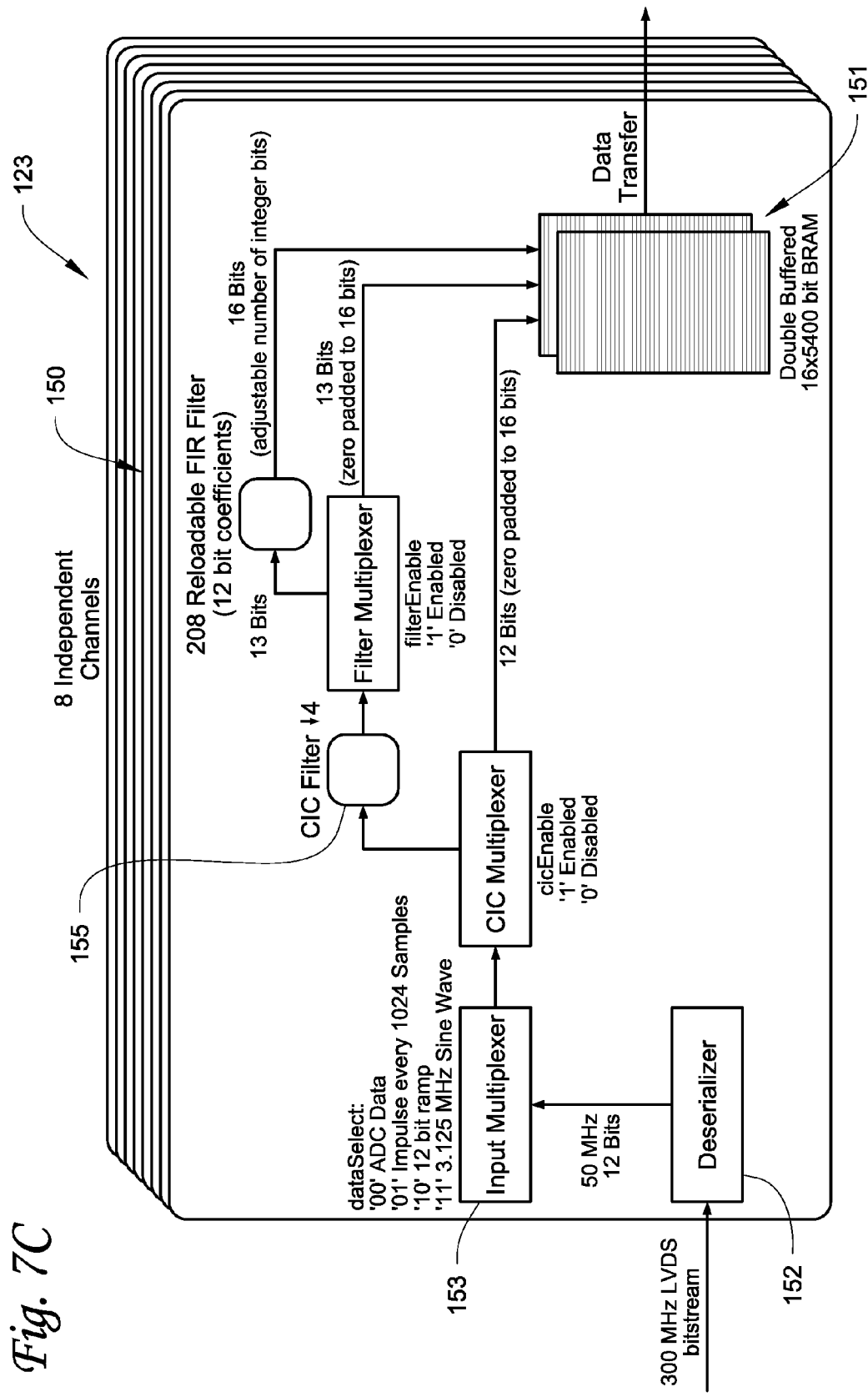
Figure 7D:
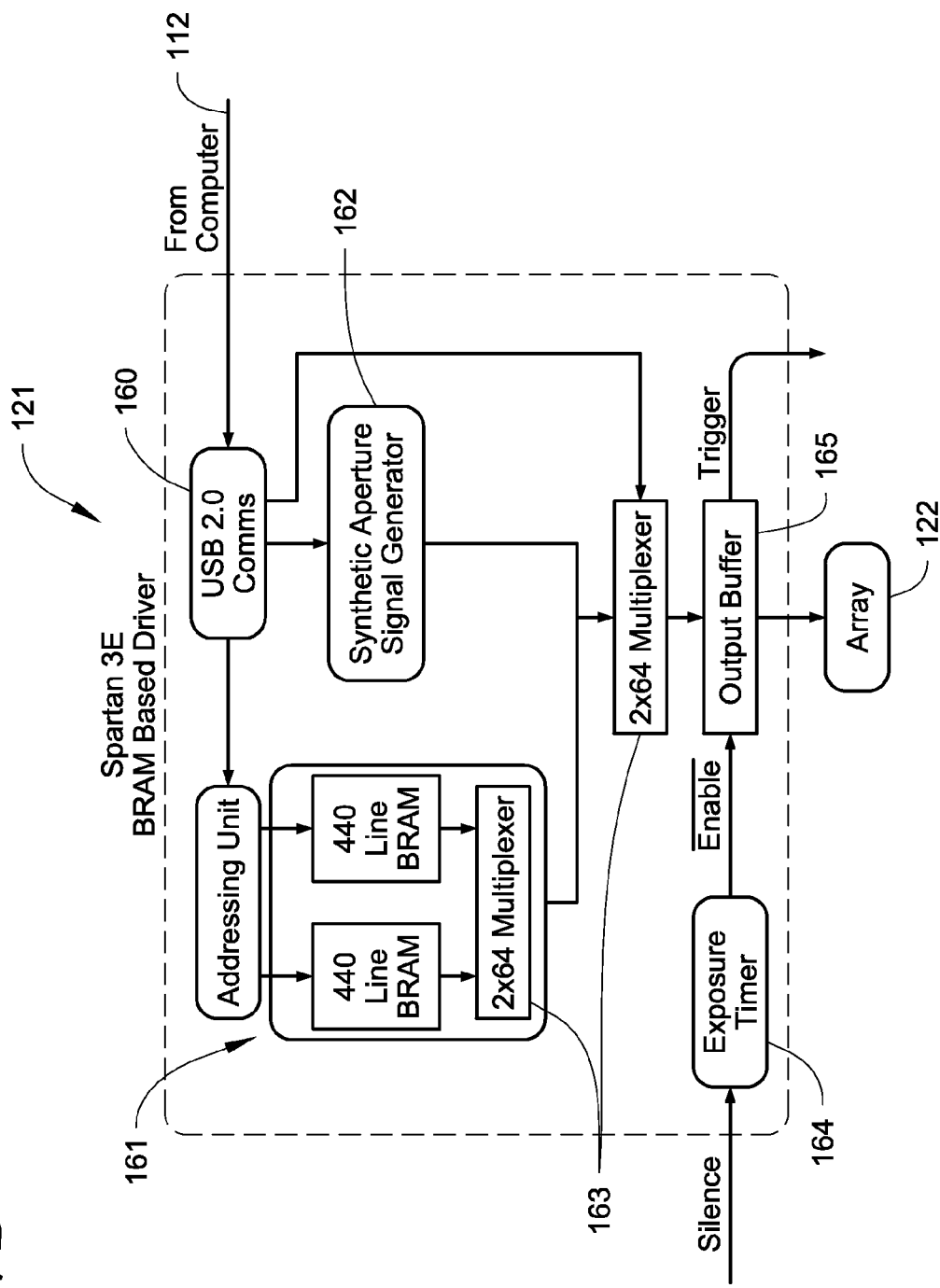
Figure 7E:
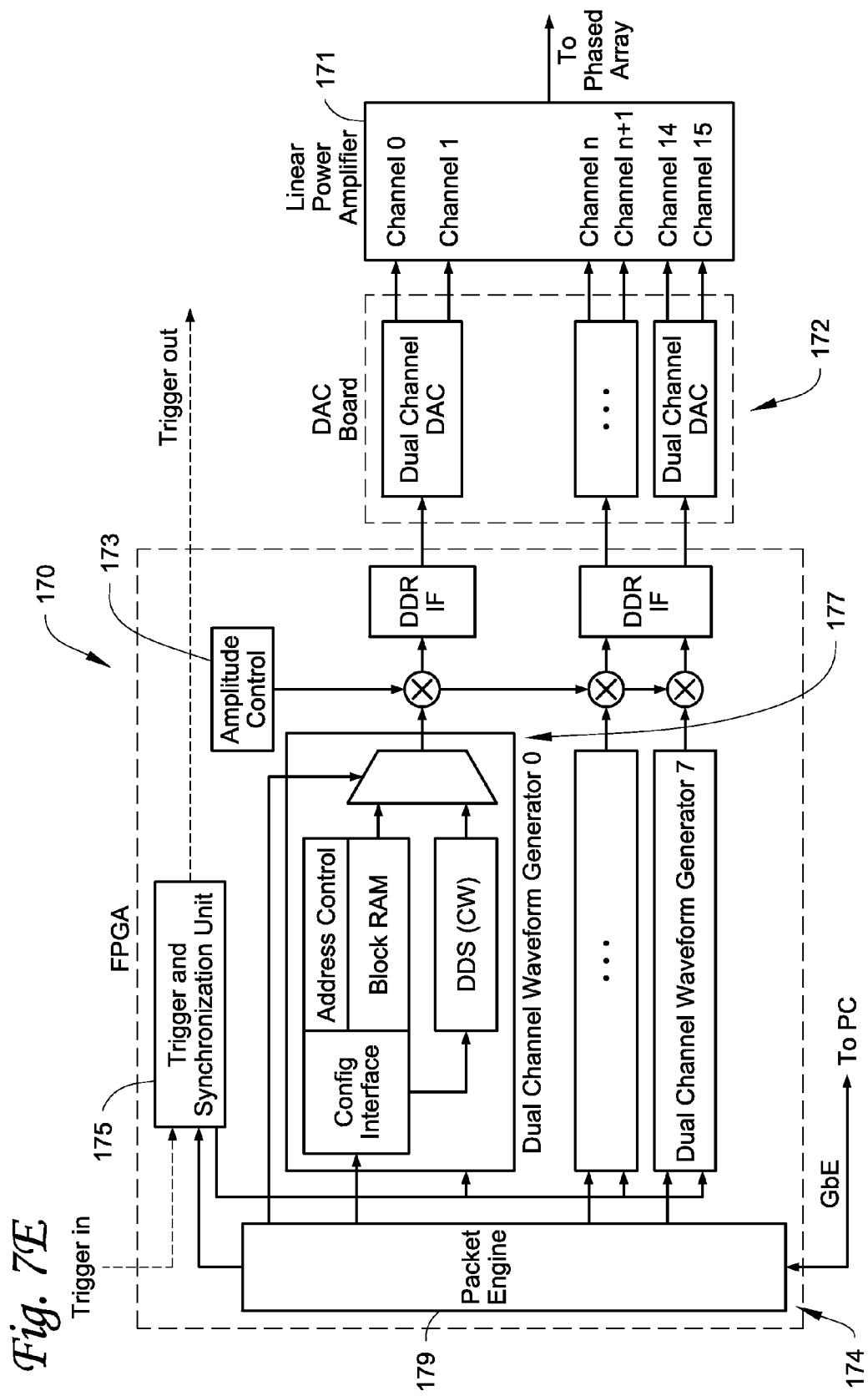
Figure 7F:
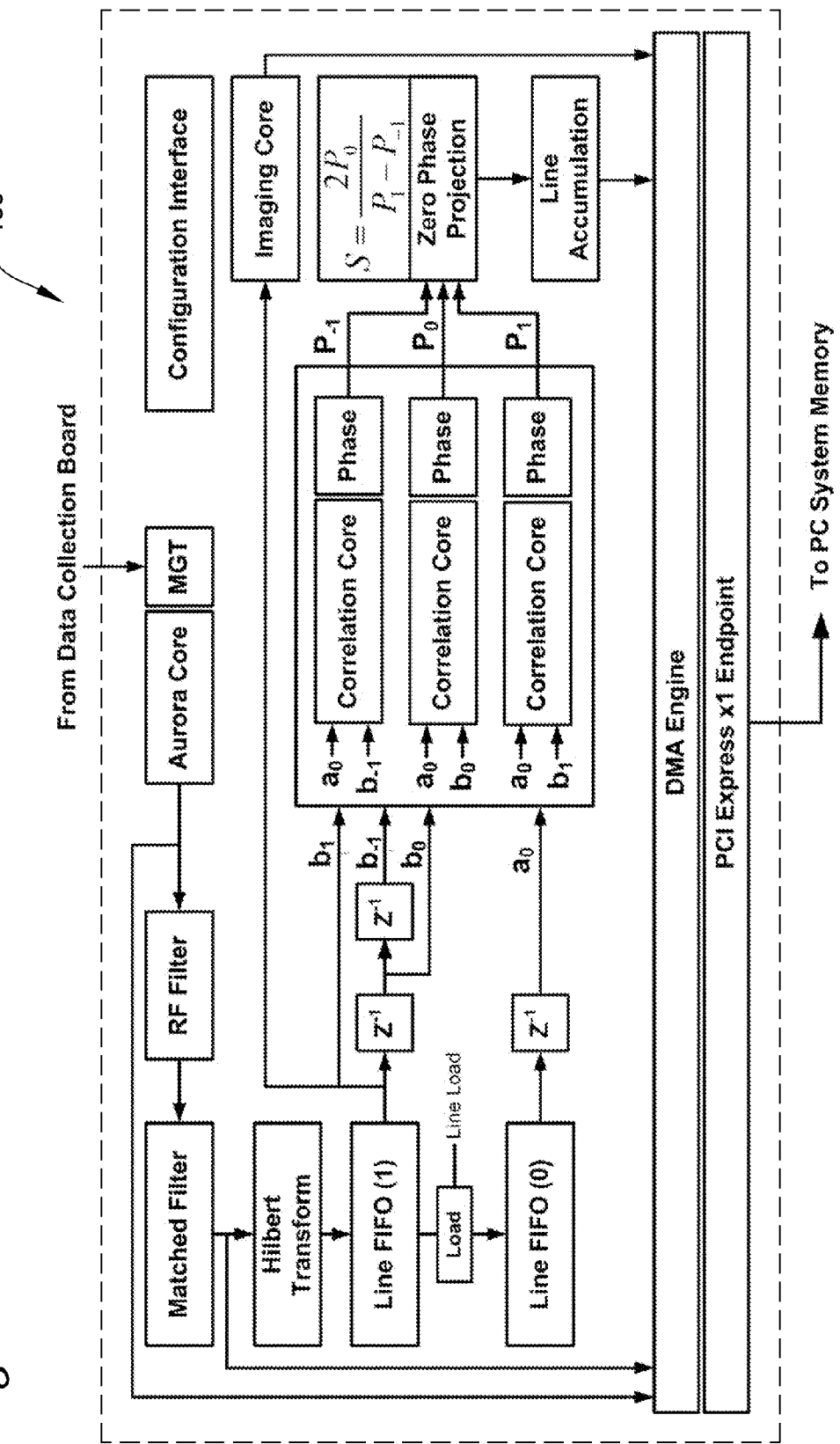
Figure 7G:
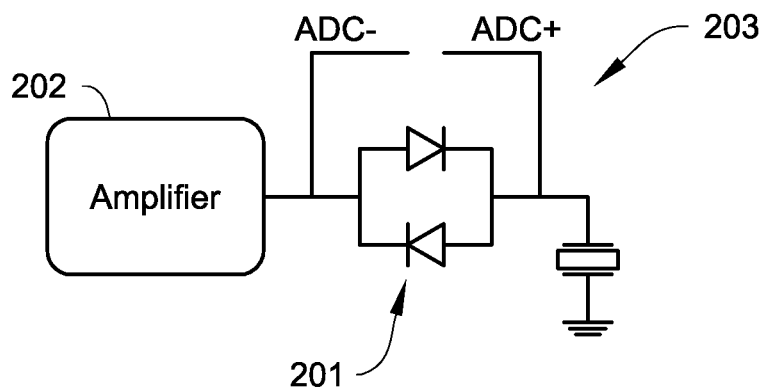
Figure 7H:
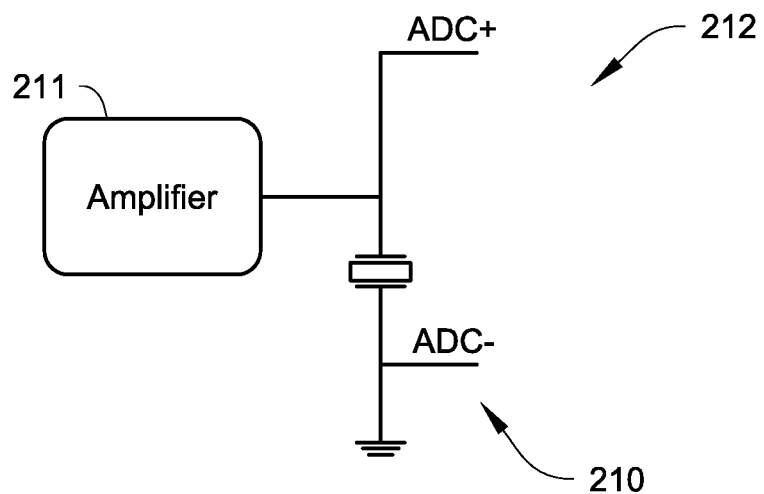
Figure 7I:
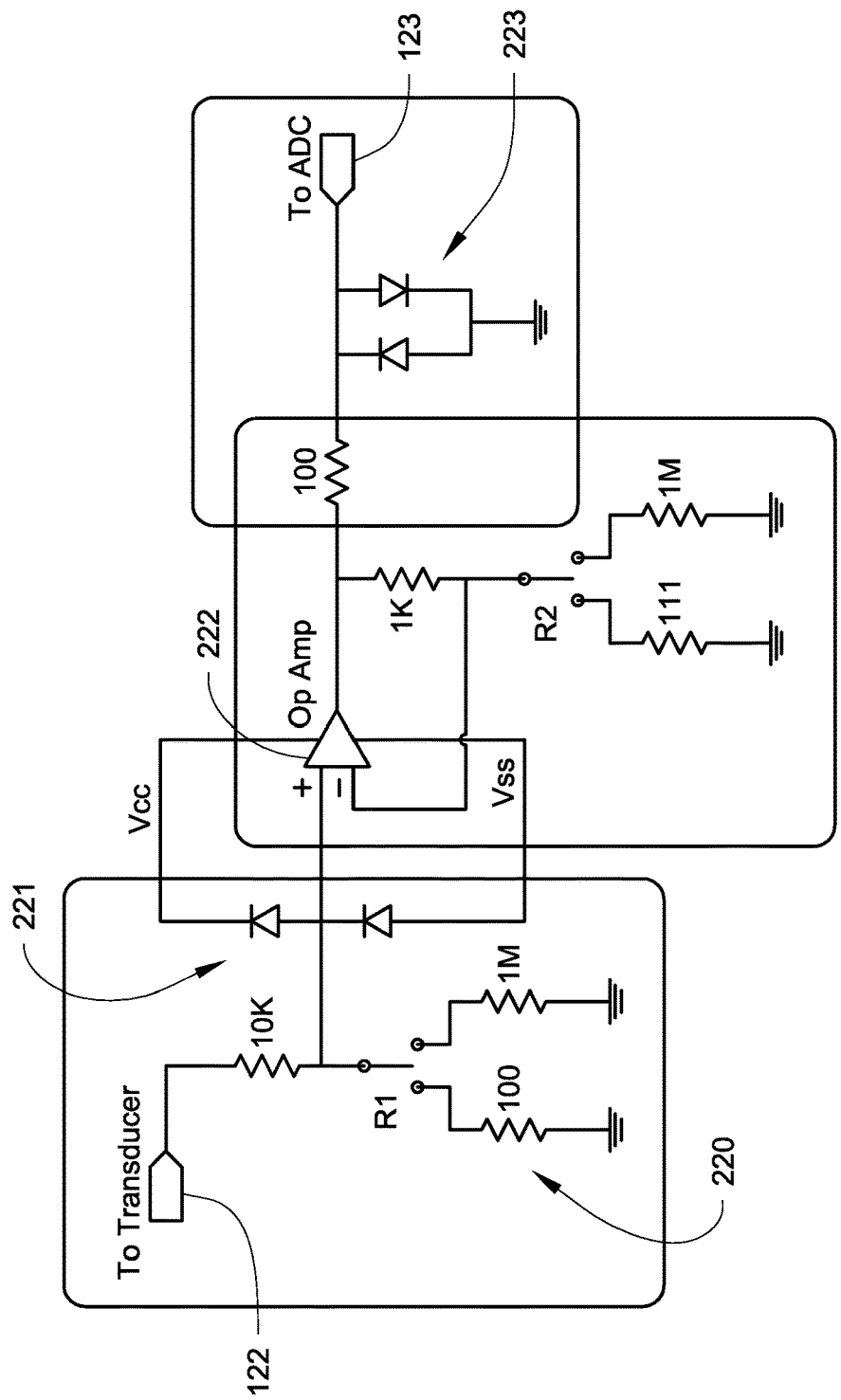
Figure 7J:
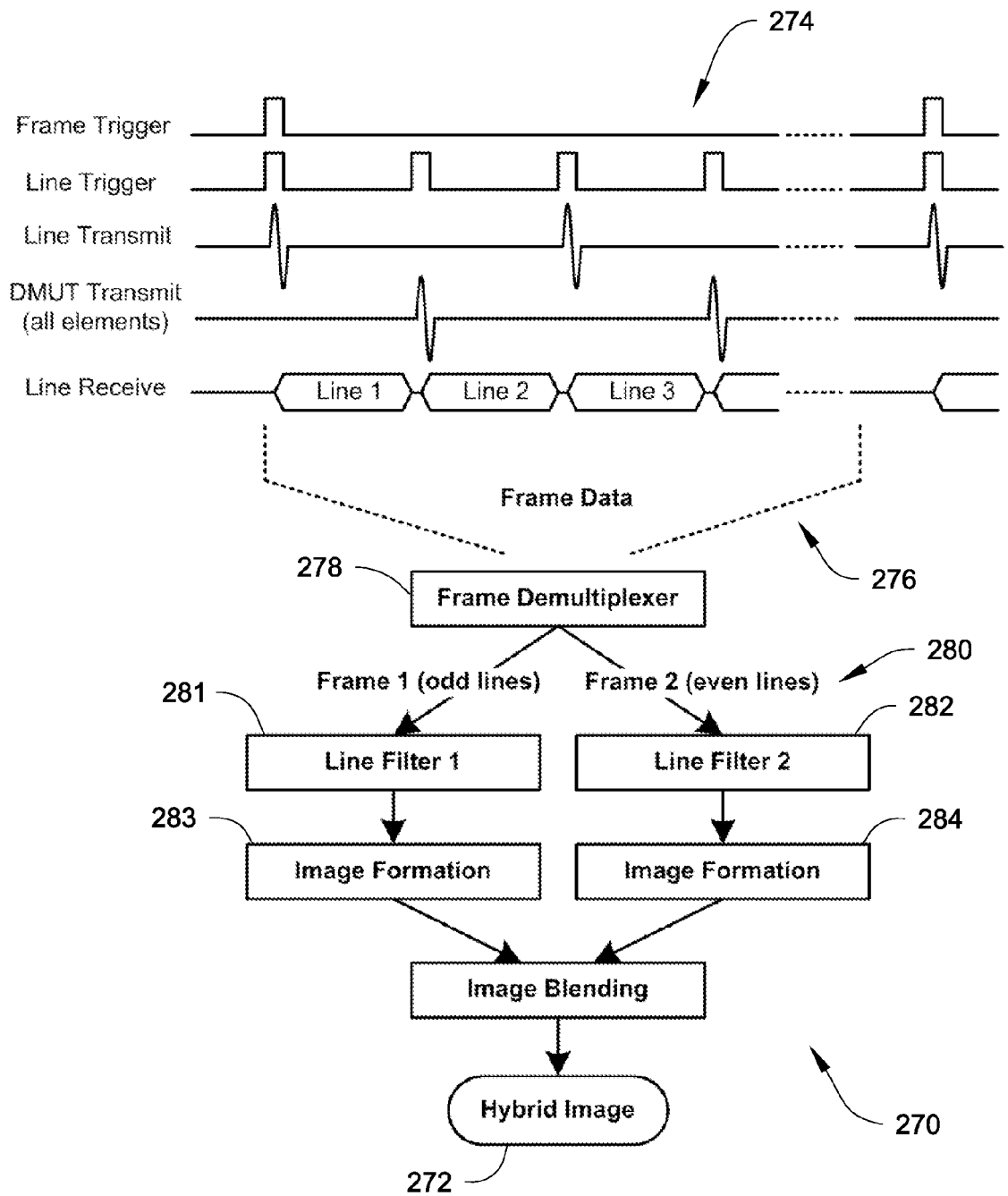

FIG. 7J illustrates one exemplary process 270 of one embodiment of fusing images, or in other words, illustrating the concept of hybrid imaging from hardware (e.g., beam sequencing) and software (e.g., image formation) levels. To form a hybrid image 272, first the hybrid imaging beam sequence 274 is designed. For example, for a given frame of N Alines, there will be total of 2N line triggers. For an individual frame, Aline n (1<=n<=N), the first line trigger (2n−1) triggers the SonixRP pulser to transmit a pulse just like the regular B-mode imaging. For the second line trigger (2n), the SonixRP pulser will remain silent and the DMUT transmits a pulse using a pre-loaded focus pattern. The SonixRP receiver collects echo data from both line triggers. To form a hybrid image 272, first the composite frame data 276 is de-interleaved using a frame demultiplexer 278, forming two RF frames 280 that contain odd lines (frame 1) and even lines (frame 2). Frame 1 is filtered with a broadband BPF (Line filter 1) 281 to form a regular B-mode image 283, frame 2 is filtered with a narrowband BPF (Line filter 2) 282, centered at f0 or 2f0 (where f0 is the transmit frequency) to form the beam overlay image 284. The two formed images 283, 284 are blended (e.g., alpha blending) to form the hybrid image.

Figure 10A:
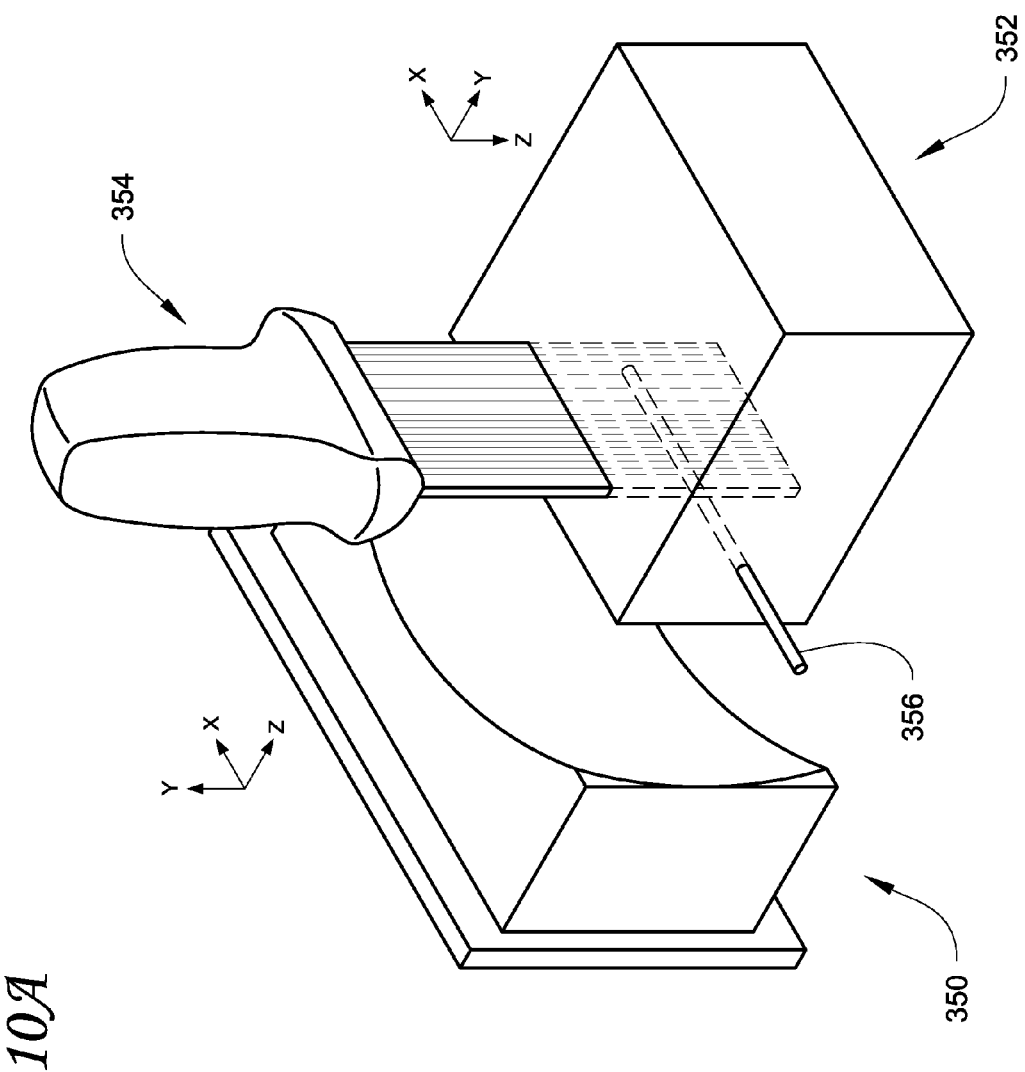
FIGS. 10A-10J are illustrations, graphs, etc. for use in relating to examples carried out and described at least in part herein with respect to multiple focus temperature control with noninvasive ultrasound thermometry.

As shown in FIG. 1, additional diagnostic apparatus 20 may be used to perform imaging to provide one or more different functions. For example, the additional diagnostic apparatus 20 may include apparatus for receiving pulse-echo data resulting from the delivery of therapy pulses. For example, although imaging described herein is generally performed using the DMUT array 22 (e.g., generating imaging pulses and receiving echoes as a result thereof), a diagnostic apparatus may be used to receive pulse-echo data that results from the application of the therapy pulses. For example, a separate apparatus (e.g., separate from the DMUT array 22) used for receiving pulse-echo data is shown in FIG. 10A, wherein imaging pulses are delivered using the DMUT array 350 and pulse-echo data resulting therefrom is captured by linear array imaging probe 354. It will be recognized that any such additional diagnostic apparatus may be used to capture such data.

In the case of capturing pulse-echo data resulting from the delivery of therapy pulses, such captured data may be used to characterize the therapy beam's focusing quality at the target location. This may be used to form and provide visual feedback to the physician to assist her/him in deciding the next shot of therapy to be delivered. A more quantitative image of the therapy beam may be obtained from applying high-speed strain imaging with a modified version of the sequence shown in FIG. 7J. For example, the sequence 274 can be modified such that three triggers: 2 triggers to the imaging device acquiring echo data on the same line before and after a trigger to the DMUT. The two acquisitions on the imaging scanner can be separated by, for example, 400 microseconds. The two echoes can be correlated near the therapy pulse (e.g., using circuitry like shown in FIG. 7F) to produce tissue displacements at the focus, which is characteristic of the local mechanical tissue response to the therapy beam at diagnostic level (e.g. thermal expansion pulse). Alternatively, QB-mode imaging can be applied to characterize cavitation activity resulting from short-duration bursts from the therapy beam. In general, hybrid imaging can be used to characterize the quality of focusing for the therapy beam and local tissue response to short sub-therapeutic bursts, which can be used in controlling the next application of the HIFU beam.

Further, each of the ultrasound transducer elements of the array 122 may be coupled to the rest of the system 110 by a control channel including a diplexer 125 for each element (e.g., a diplexer or switch to manage the coupling of signals between the driver 124 and the array 122 (e.g., therapeutic and sub-therapeutic signals) and between data collection 123 and the array 122. In other words, a multi-channel control to/from the array 122 may be implemented. For example, an array of A/D convertors may be coupled to the transducer elements of the array 122 (e.g., in a one to one relationship, or multiple transducer elements per converter, etc.). Signal levels at the array during therapeutic operation may be in the range of 100's of volts, whereas signal levels at the array during imaging operations may be in the range of millivolts. As such, one or more configurations of the diplexer may be more beneficial over others.

For example, one exemplary diplexer 125 (e.g., suitable for each control channel between the transducer element of the array 122 and the rest of the system) is shown and described with reference to FIGS. 7G-7I. The primary goal of the ultrasound diplexer is to isolate the A/D converter from the high voltage applied to the transducer (e.g., therapeutic signals) but still allow the low level signals from the pulse-echos to pass through. The DMUT diplexer faces several challenges beyond what a normal diagnostic level diplexer encounters. For example, because the same transducer element of the array 122 is used for both imaging and therapy, the DMUT diplexer must be able to handle sustained high voltage signals (i.e., therapeutic signals). A conventional diagnostic transducer will only transmit a few cycles of a high voltage pulse (lasting only a few microseconds) so any components in the diplexer will deal with minimal energy deposition. The DMUT may transmit very long bursts (for instance 500 microseconds therapy burst, repeated every 1000 microseconds, i.e. 50% duty cycle 1 k PRF), so the diplexer must handle such signals. Second, the large element size of the DMUT compared to a conventional diagnostic transducer means the echos received during imaging may result in a relatively large voltage. An echo from a conventional diagnostic transducer may create a voltage waveform that is only a few millivolts peak to peak, but the DMUT when imaging the same medium may have echos that are 10's of volts peak to peak.

At first glance, this sounds like a good thing since one is getting more SNR. However, it requires that the echos be dealt with in a different way than a conventional diagnostic device. For example, if you have voltages that are only a few millivolts, you can use diodes 201 to act as a basic diplexer as shown in FIG. 7G. When the amplifier is outputting a high voltage signal, the voltage between ADC− and ADC+ is limited to about 0.7 volts due to forward conducting diodes. After transmitting the high voltage pulse, the output of the amplifier 202 is pulled to ground, any voltage from the transducer less than 0.7 volts effectively sees an open circuit between ADC− and ADC+, so the ADC 203 can appropriately receive and convert the signal. Any signal larger than 0.7 volts is clipped rendering it unusable.

The diplexer 210 shown in FIG. 7H provides improved functionality. It differs from the diplexer of FIG. 7G in that the output of the amplifier is set to a high impedance state when not transmitting a signal. Further, the diodes 201 (e.g., such as in FIG. 7G) are eliminated which allow the receipt of large signals undistorted; however, it also exposes the A/D system 212 to the high voltage transmit pulses. A schematic of the diplexer 210 is shown in FIG. 7I. The signal from the transducer of the array 122 goes through a software selectable voltage divider 220 that will either attenuate the signal, for example, by 100 times or leave the signal at its current level. This is controlled by the relay R1 and is typically set dependent on the type of operation being carried out. The output of the voltage divider 220 is connected to the two diodes 221 as well as the input of a high speed op-amp 222 (e.g., AD8041). The two diodes 221 prevent the voltage at the output of the voltage divider 220 from rising above the supply voltages to the op amp 222. This protects the circuit from damage when a therapeutic level signal is applied to the transducer element of the array 122.

The gain of the op-amp 222 is also software selectable between, for example, x10 and 0, via relay R2. This allows some additional control of the signal. The final two diodes 223 before the output to the A/D converter of data collection 123 just provide some additional protection to the A/D converter.

In summary, the diplexer provides high voltage isolation/ attenuation that protects sensitive receive electronics from high voltage therapy and imaging pulses. This stage also selectively attenuates the echos received from the DMUT. The large elements on the DMUT convert even small echos to relatively large voltages (~30 Volts); and this stage allows enough dynamic range to handle these signals. Further, buffering/programmable gain of the diplexer provides a buffering stage to drive the A/D converter, and also provides optional +20 dB or 0 dB gain. Still further, the over-voltage protection ensures that the signal to the A/D converter is not much larger than 1 volt peak-peak.

Signal acquisition for data collection 123 (e.g., pulse echo image data) may be performed in any suitable manner. For example, a transducer element signal may be sampled at 40 MHz, 12 bits, full scale range 1V (e.g., the element samples a approximately 1 MHz and the 40 MHz sampling rate is far in excess of that required by the Nyquist principal); each channel may have an independent digital filter and reconfigurable down-sampler; the data may be filtered in real-time and stored in memory; and the data may be communicated to the computer for further processing.

FIGS. 7B-7C provide diagrammatic illustrations showing the translation from an analog signal on the DMUA element, into a digital signal read in by the computer though some standard interface (USB, Ethernet, etc.). For example, FIG. 7B depicts a single channel according to one example of data collection 123 between a transducer element of an array 122 and the computer 112 including an analog to digital convertor (ADC) 140 for sampling the signal from the transducer element of the array 122. In other words, FIG. 7B shows a diagram of a single channel of a multi-channel data acquisition system implemented, for example, using an FPGA. The ADC 140 is continuously converting the analog signal at its input into a digitized 12 bit word at 40 Mega samples per second. The triggering unit 149 controls when this data is read into the FPGA including A-line storage 144. Once triggered, the FPGA latches the data into the device, and routes it through DSP processes (e.g. the decimator 142 and any filtering). It then stores 5000 contiguous samples (e.g., A-line storage 144). Once stored in the FPGA, the computer 112 can then download the data and commence further processing. In this case, the communication protocol 145 was USB 2.0.

FIG. 7C depicts an 8-channel analog to digital convertor data collection apparatus including down-sampling according to another example of data collection 123 between a transducer element of an array 122 and the computer 112. For example, FIG. 7C shows a single channel but from an alternative embodiment of a multi-channel data acquisition system. For example, in one embodiment, such a multi-channel system (e.g., with may be implemented using a FPGA) may use a different ADC integrated circuit that includes 8 A/D converters on a single chip. FIG. 7C shows only one channel in detail, but this is repeated for all 8 channels 150 on the single integrated circuit. The data signal path is very similar to 7B, except that now the path can be configured on the fly. The data can be passed directly into the FPGA buffer upon data select 153, or it can first be passed through a decimator or a matched filter 155, e.g., a matched filter reconfigurable in software may be used with coded excitation). In addition, the FPGA can create debugging data for testing the integrity of the signal path; this is controlled by the variable dataSelect 153. A sine wave, an impulse, and a ramp can all be simulated to ensure proper operation of the whole system. The communications with this system all take place through a Gigabit Ethernet connection (1 connection per 16 channels).

The DUMA driver 121 includes a multichannel driver configured to drive the ultrasound transducer array elements with independent waveforms in both therapeutic and image modes. Further, the DMUA driver 121 may be configured to store and control the signals (e.g., therapy and image signals) played on the DMUA elements; the driver 121 may be capable of double buffering therapy beams so focus may be updated without interruption to therapy; the driver 121 may be suitable for both STF Imaging and Synthetic Aperture imaging during therapy (or any other imaging to be carried out); and the driver 121 may allow for direct user control over therapy while accumulated exposure occurs. For example, in one or more examples, a plurality of buffers may be used to deliver therapy. For example, a first buffer may provide storage for the therapy protocol currently being delivered and a second buffer may provide storage for therapy to be delivered in the next period of time. The buffers may be selected based on a pointer or other technique. In one example, the buffers are managed in a manner to provide a reconfigurable silencing period with a granularity of less than 1 microsecond (e.g., well below the mechanical and thermal response time of the tissue).

For example, FIG. 7D illustrates an exemplary field programmable gate array (FPGA) configured to function as driver 121. Communication component 160 represents a communication module and may include a USB port. The driver may be implemented using a discrete block random access memory (B-RAM), and can be viewed as a state machine based memory unit. In other words, FIG. 7D shows an exemplary diagram of a therapeutic driver including addressable BRAM 161 for use in generated drive signals. The drive signals provided to the array 122 by output buffer 165 under control (at least in part) of exposure timer 164. Each channel is controlled by an arbitrary square wave (e.g., unique phase, and amplitude). In the diagram of FIG. 7D, the lacks spectral content control. In other words, only the duration and power in the fundamental frequency can be controlled. For example, one could not play out a signal with both 1 MHz and 2 MHz components. This driver of FIG. 7D does allow both imaging (e.g., SA imaging, STF imaging, and coded excitation to at least a limited extent) and allows delivery of therapy pulses. The multiplexers 163 allow for double buffering. In single buffering, one would have to stop playing a pattern if you wanted to update the therapy beam. With double buffering, you can play one pattern while you update the other without ever needing to pause. The driver of FIG. 7D has a specific unit for SA imaging 162 to minimize resource utilization.

Further, for example, FIG. 7E illustrates another exemplary field programmable gate array (FPGA) configured to function as a linear driver 170 for the ultrasound phased array 122 (e.g., including an 8-channel arbitrary waveform generator). This driver system 170 may be use with a 3.5 MHz DMUT array. The driver system 170 may be divided into three major functional blocks including an FPGA waveform synthesizer (block 174). The waveform synthesizer 174 allows generation of waveform (digital stream) from either internal BRAM (pre-loaded arbitrary waveform) or a direct digital synthesizer (DDS) (see, generators 177). The generated waveform can also be optionally amplitude modulated (AM) with an amplitude control unit 173 (e.g., a function for a tissue mechanical property test). In addition, the waveform synthesizer 174 features a synchronization and trigger unit 175 for cascading multiple boards to support more channels and to coordinate beam sequence for various imaging mode (M2D-mode imaging, hybrid imaging, etc.). Both the configuration registers and the arbitrary waveform generator can be loaded with the packet engine 179 (Gigabit Ethernet+UDP/IP). DAC board (block 172) is configured to convert a digital stream into low voltage analog waveform (1Vp-p max into 50 ohm load). Further, the driver system 170 includes a linear power amplifier (block 171) to amplify a small signal (1Vp-p max) to a high voltage signal (50Vp-p max into 50 ohm load) to drive the phased array 122.

Still further, FIG. 7F shows an exemplary implementation of 1D speckle tracking (e.g., the core algorithm in ultrasound elastography and thermography) in a Virtex5 FPGA. For example, such an FPGA may be a component of the multimodal imaging 134 of FIG. 7A. The mathematical form of the 1D speckle tracking can be found in Simon, et al., *IEEE Trans. Ultrason., Ferroelect., Freq. Contr.* 45, 989-1000 (1998) and therefore, detail with respect to the implementation of FIG. 7F is deemed unnecessary as one skilled in the art would understand such an implementation. The illustrated implementation of FIG. 7F primarily serves two purposes. The first is to demonstrate the feasibility of fitting the algorithm into a FPGA, which is useful for implementing an integrated system with all FPGA design to achieve minimum latency (e.g., without the intervention of a non-real-time computer system). Further, the implementation demonstrates the design philosophy for implementing the algorithm to a specialized system (e.g., FPGA/GPU, etc.) which can be performance enhancing and/or be accomplished with limited resources.

In addition, multimodal imaging 127 is coupled to the data collection 123 and computer 112. Multimodal imaging 127 represents circuitry and programming suitable for performing one or more modes of imaging, such as for use in control of the therapeutic bean (e.g., for use in analyzing movement of the subject and other tissue dynamics or response).

A flow chart of an exemplary ultrasound therapy method 30 for delivery of image guided ultrasound therapy is depicted in FIG. 2. One will recognize that one or more of the blocks of functionality described herein may be carried out using one or more programs or routines, and/or any other components of a therapy system (e.g., the therapy system 10 of FIG. 1).

Generally, the method 30 includes an initiation of the therapy process 30 via a therapy start procedure (block 31) (e.g., a user initiated a therapy session via the user interface 15 as shown in FIG. 1). As shown in FIG. 3, such a start procedure may provide for implementation of one or more imaging processes (e.g., one or more imaging modes) as shown by pre-therapy imaging pulses 42. For example, an array of ultrasound transducer elements (e.g., array 22 configured to deliver a plurality of sequential therapy bursts of ultrasonic energy to at least a portion of a target region and to transmit/receive imaging ultrasonic energy to/from the target region) may deliver image pulses 42 to obtain pulse echo data representative of a treatment region in which a target for therapy is located. In other words, the method may include generating treatment region image data that includes the target region.

As shown in FIG. 2, at least one or more target points within the treatment region may be identified (e.g., target points on a liver tumor to be treated) in treatment region image data generated based on pulse echo data received by one or more of the plurality of ultrasound transducer elements of the array 22 (block 32) (e.g., SA imaging may be used to produce treatment region image data for use in identifying one or more target points). As is further defined herein, other control points may be identified, such as critical points on intervening tissue between the target points and the array 22. For example, as shown in FIG. 7A, an image may be presented on a user interface allowing a user to select one or more control points (e.g., target points, critical points, etc.).

Further, the therapy method 30 includes generating therapy signals to drive one or more of the plurality of ultrasound transducer elements to deliver a therapy burst of a plurality of sequential therapy bursts (see, e.g., therapy bursts 40 in FIG. 3) of ultrasonic energy (e.g., forming a focused beam) to at least one of the one or more target points in the target region) (block 33). Each of the sequential therapy bursts 40 may be defined to produce a response at the one or more target points within the target region (e.g., each may be defined differently to guide the beam throughout therapy based on control image data). Thereafter, the therapy burst is delivered (block 34) to produce an effect in the target (e.g., liver tumor).

Following delivery of the therapy burst (block 34), control image data is generated (block 38). Such control image data may be generated (block 38) based on pulse echo data received by one or more of the plurality of ultrasound transducer elements following delivery of the therapy burst (block 34). The control image data generated following delivery of a therapy burst may be used to generate therapy signals to drive one or more of the plurality of ultrasound transducer elements to deliver a subsequent therapy burst of the plurality of sequential therapy bursts (block 38 and 33). The continuous process of delivering therapy bursts (block 34) and thereafter generating control image data for use in defining a subsequent therapy burst (block 38) is continued until the therapy is stopped (block 36).

Still further, in one or more embodiments, the control image data may be generated using imaging that is performed during delivery of one or more therapy bursts. For example, such imaging may be implemented with use of coded excitation (e.g., with coded excitation, imaging data can be obtained even during the delivery of therapy). For example, image control data (e.g., generated and/or provided during and/or following delivery of one or more therapy bursts for control of one or more subsequent therapy bursts) may be obtained based on imaging performed (e.g., at least in part) during the delivery of the therapy bursts (e.g., such was with use of coded excitation).

As shown in FIG. 3, such a stop procedure (block 36) may provide for implementation of one or more imaging processes (e.g., one or more imaging modes) as shown by post-therapy imaging pulses 44. For example, an array of ultrasound transducer elements (e.g., array 22 configured to deliver a plurality of sequential therapy bursts of ultrasonic energy to at least a portion of a target region and to transmit/receive imaging ultrasonic energy to/from the target region) may deliver image pulses 44 to obtain pulse echo data representative of the treatment region in which the target is located for various purposes, to determine if more treatment is necessary, to view the results of treatment, etc.

One will recognize that the process shown generally in FIG. 2 may be continuously repeated for any number of control points to provide any desirable therapy. In other words, such processes may be used to continue to move the therapy beam and treat various portions of a target region.

The generation of control image data for use as feedback in defining subsequent bursts to be delivered (block 38)

(e.g., to refocus the beam or provide image guiding of the beam) may take one of various faults. For example, generating control image data during and/or following delivery, of the therapy burst may include generating at least one imaging signal to drive one or more of the plurality of ultrasound transducers to transmit at least one single transmit energy pulse focused to at least one or more target points within the target region resulting in pulse-echo data to be captured (e.g., STF imaging of one or more control points, such as target or critical points).

For example, in the case where both target and critical points in intervening tissue are identified (e.g., control points), STF imaging may be used at each control point to obtain image data pertinent thereto. For example, such control image data may include ultrasound transducer element directivity data (e.g., array directivity vectors that may be used to define the therapy signals such that the therapy burst based thereon may minimize power at the critical points, such as intervening ribs, and maximize power at the target points). In other words, the therapy beam is refocused to maximize power at the target points (e.g., in addition to preventing damage to adjacent structure).

Further, for example, such control image data may include thermal response data. Such thermal response data may be used to control the focused beam in any number of ways. For example, such thermal response data may be used to determine when a set point for thermal therapy has been reached, may be used to define the therapy signals such that the therapy burst based thereon redistributes the intensity of the ultrasound energy amongst different target points, etc. For example, as described herein by redistributing the delivered energy amongst different points, therapy time may be decreased.

In one or more embodiments, thermal response data may be generated for feedback after each therapy pulse is delivered (e.g., such as in the use of power reallocation amongst the elements of the array). However, in one or more embodiments, image control data (e.g., such as thermal response data) may be generated after the delivery of multiple therapy bursts of a thermal therapy shot (e.g., a plurality of bursts with intermittent imaging pulses such as shown in FIG. 3). For example, an exemplary process for use of such control image data is shown generally in FIGS. 8C-8D.

Further, for example, such control image data may include data indicative of cavitation. Such data indicative of cavitation may be used to control the focused beam in any number of ways. For example, such data may be used to define the therapy signals such that the therapy burst based thereon reduce heat at regions where cavitation is appearing but is undesirable, to increase at target points where cavitation is desired but not occurring, etc.

Figure 11:
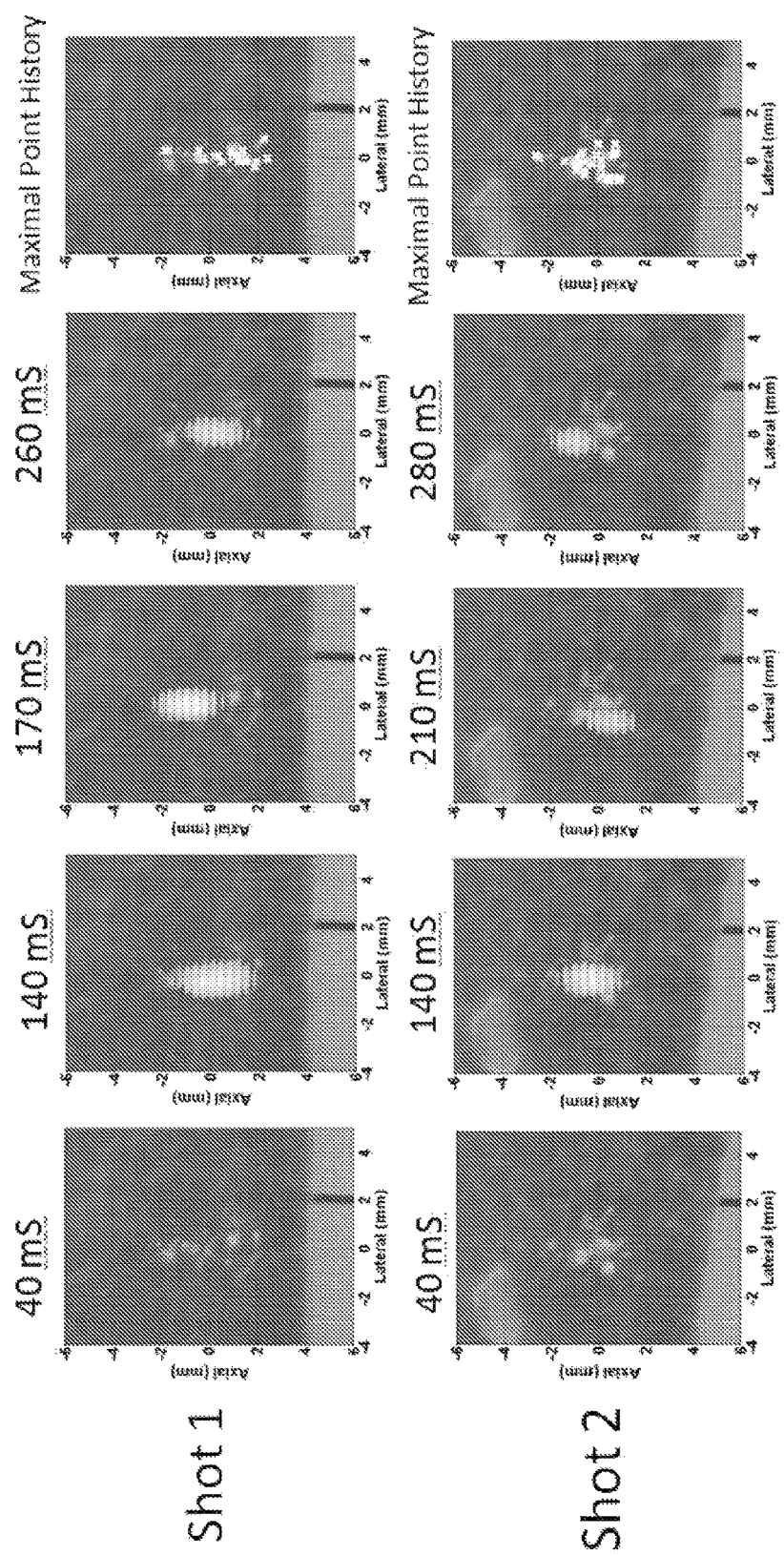
FIG. 11 shows images for use in describing data indicative of cavitation use to control therapy.

For example, such data indicative of cavitation may include the detection of bubble activity on tissue. For example, such bubble activity may be detection using image data and algorithms described in U.S. Pat. No. 6,951,540 to Ebbini et al., entitled "Ultrasound imaging system and method using non-linear post-beamforming filter" and H. Yao, et al., "Enhanced lesion visualization in image-guided noninvasive surgery with ultrasound phased arrays," in Proc. 23rd Annu. Int. Conf. IEEE Eng, Med Biol. Soc., October 2001, vol. 3, pp. 2492-2495. Such visualization is shown in FIG. 11. For example, FIG. 11 shows the results from a 300 milliseconds exposure of HIFU at approximately 8000 W/cm2 (e.g., images taken over time at the noted time periods). At these intensity levels, cavitation bubbles were formed very quickly and continued to grow throughout the exposure. The tissue damage (i.e., lighter shade regions in the image) is indicative of where the cavitation bubbles were formed and sustained leading to increased heating. Overlaid on these images is the output of SVF (second-order Volterra filter) with the dynamic range consistent throughout each shot.

It is clear from FIG. 11 that the quadratic signal component grows as the therapy progresses and is also well contained within the focus location. The final image on the right of each shot shows the maximum signal location from each of the 30 frames. The photographs of Shot 1 and 2 show that the tissue damage in each case took on a slightly different shape. Shot 1 shows a more oblong appearance, while Shot 2 is more circular. This visual appraisal may be corroborated by the mapping of the maximum points. In each case, the maximum points map to the true shape of the tissue damage. One aspect of this mapping is its ability to locate events within the focal point of the transducer. This transducer (F#0.8) has a focal length of around 12 mm which is an order of magnitude larger than typical cavitation events at this frequency. This allows for multiple events to be initiated within the focal region of the transducer. Utilizing the quadratic signature of the bubbles, one is able locate these events within the focal region, a task not possible with simple pulse-echo beamforming.

Still further, for example, such control image data may include displacement/strain data (or any other mechanical response data associated with the target region, such as temperature change data, cavitation activity data, etc.). Such displacement/strain data may be used to control the focused beam in any number of ways. For example, such data may be used to identify oscillations indicative of cavitation at the target points, as well as other points in the path of the beam. Further, for example, such data may be used guide the beam with respect to the target points as the target points are displaced. In other words, for example, in one or more embodiments, pulse-echo data suitable to provide displacement fields in flow and/or tissue may be used to generate control image data. For example, in the case of thermal therapy being used to treat the base of a plaque structure on a vessel wall, such displacement/strain data may be used to refocus the beam to the target points based on the displacement/strain data.

For example, such control image data may be realized from M2D mode imaging designed to maximize the lateral extent of the imaged region at sufficiently high frame rates to capture the full dynamics of the vessel wall and the flow within the vessel. M2D mode may produce 2D beamformed RF echo data from a selected region of the field of view (FoV) of a given probe. The region may be contiguous or comprised of more than one disjoint subsegment. As an example, on the SonixRP scanner (Ultrasonix, BC, Canada), an arbitrary set of A-lines within the FoV can be used to form the M2D mode image with frame mode approximately $M_B/M_{M2D}$ higher than B-mode imaging, where $M_B$ and $M_{M2D}$ indicate the number of A-lines used to form B-mode and M2D-mode images, respectively. Such M2D mode imaging may be enabled by creating a powerful pipelined execution/flow program architecture capable of employing a variety of computational resources for real-time implementation. In addition, the program architecture may allow the user to invoke additional computational resources available on the computer (or generally on the Internet) to achieve other computational tasks. The results from these computations can be integrated seamlessly with the program. For example, the beamformed RF echo data may be transferred in real time through a Gigabit interface to allow real-time 2D axial strain computations using GPU (or FPGA) using 1D speckle tracking. However, the beamformed RF data is available for additional processing using, for example, a pre-installed MATLAB engine. The MATLAB results can be imported back seamlessly to the M2D mode imaging program with minimum latency (e.g., after the completion of the MATLAB calculations). This capability may allow us to perform real-time speckle tracking to enable strain and shear strain in the vicinity of a vessel wall (e.g., vasculature, nerves, etc.), e.g., heavy-duty MATLAB-based calculations are performed on a small RoI allowing for their incorporation in real time. In at least one embodiment, true 2D speckle tracking approaches may be implemented in real time as is currently the case with 1D speckle tracking. In this way, a pipelined program execution architecture may be implemented to support M2D imaging which allows us to reap the benefits of powerful computational tools for the analysis of the vessel walls in quasi real-time.

Still further, the high quality 2D (+time; i.e., over time) strain and shear strain will allow for tissue property measurements within the vessel wall, e.g. stiffness. Such tissue property measurements will allow for the characterization of the disease state and, given the high resolution, the plaque architecture (e.g., base, lipid core, and fibrous or calcified cap). Therapy or treatments may be delivered based on such information or such information may be used during the delivery of such therapy (e.g., high intensity focused ultrasound treatments that target the base of the plaque without damage to the cap or even the lipid core, continual determination of the response of tissue to therapy, such as between doses or pulses of high intensity focused ultrasound as described herein, etc.).

In other words, in one or more embodiments, the therapy system is configured for vascular imaging. For example, the control apparatus (e.g., GPU, CPU, etc.) may be configured (e.g., operate under control of one or more programs) to, for example, control the capture of pulse-echo data at a frame rate such that measured displacement of a vessel wall defining at least one portion of a blood vessel in the vascular region and/or measured average blood flow through the at least one portion of the blood vessel have a quasi-periodic profile over time to allow motion tracking of both the vessel wall and the blood flow simultaneously; generate strain and shear strain image data for the region in which the at least one portion of the vessel is located using speckle tracking; and identify at least one vascular characteristic of the vascular region in which at least one portion of a blood vessel is located based on the strain and shear strain image data (e.g., wherein the at least one vascular characteristic comprises at least one of a flow characteristic associated with flow through the blood vessel, a structural characteristic associated with the blood vessel, and a hemodynamic characteristic associated with the blood vessel). Such image data may be used for control or refocusing a beam as described herein.

It will be recognized that multiple types of control image data may be used to resynthesize the beam. For example, thermal response data may be used with directivity data, displacement data may be used with thermal response data, or any other combination of control image data may be used.

Yet further, control image data as shown in FIG. 2, may also be generated based on one or more test patterns (represented generally by line 37 in FIG. 2) representative of calculated therapy signals generated for delivery of a subsequent burst. In other words, prior to delivery of a subsequent therapy burst (block 34) of the plurality of sequential therapy bursts based on therapy signals generated using control image data generated during and/or following delivery of a previous therapy burst, the method 30 may include testing the subsequent therapy burst at sub-therapeutic levels. Control image data generated based on such test patterns may be used to modifying the therapy signals generated to deliver the subsequent therapy burst. For example, imaging may be performed using such test patterns 37 to generate control image data for use in generating the subsequent therapy burst to be delivered. In one or more embodiments, such imaging may use STF imaging at to test various characteristics (e.g., gain as compared to set gain levels, response levels as compared to set safety levels, temperature levels as compared to set temperature levels, etc.)

Figure 8A:
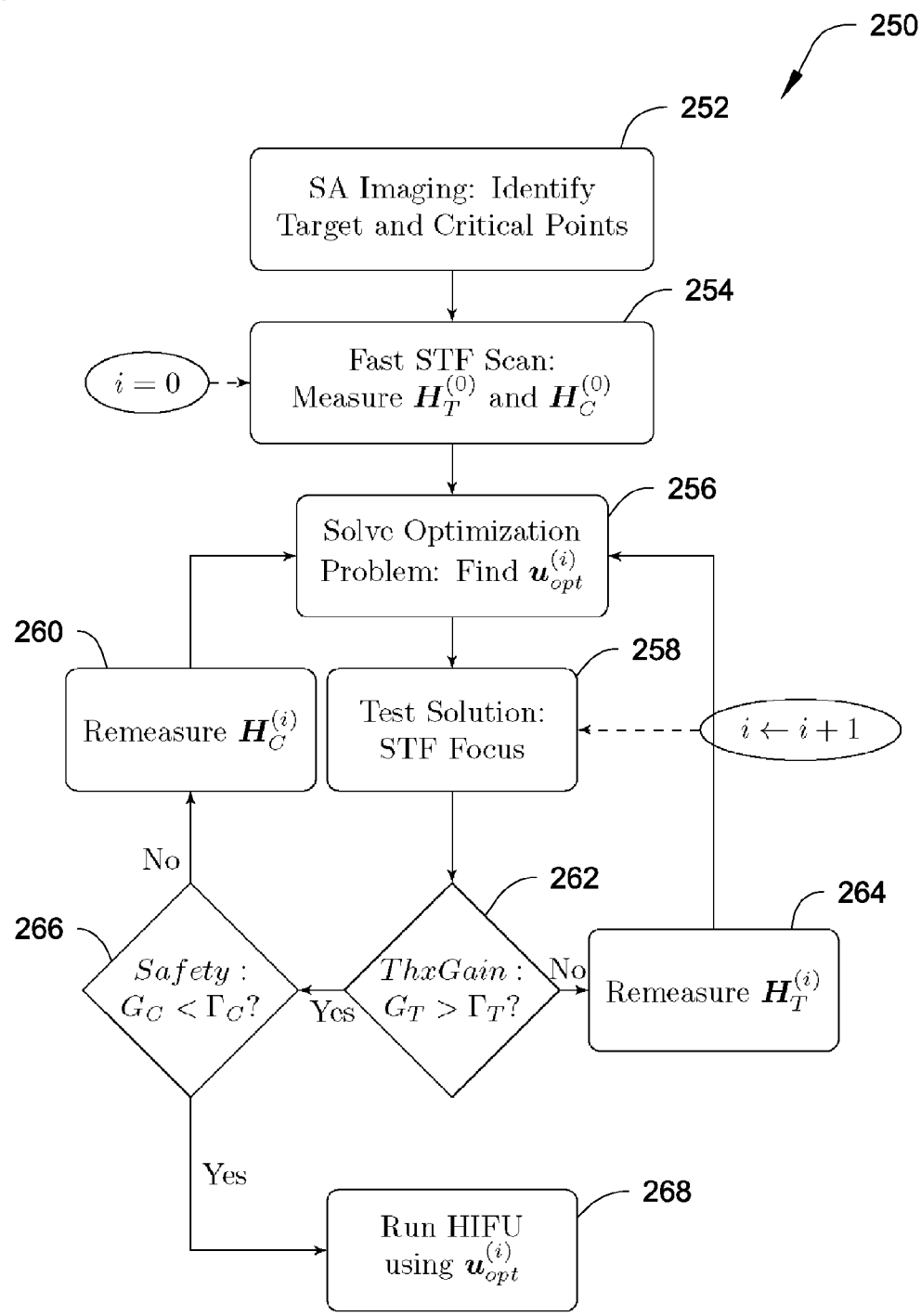

One or more exemplary therapy methods are shown in the flow diagrams and algorithms of FIG. 8. For example, therapy method 250 shown in FIG. 8A may generate at least directivity data for use in refocusing the therapy beam implemented in accordance with the following algorithm shown in FIG. 8B.

For example, the therapy method 250 may include performing imaging (e.g., SA imaging) to generate treatment region image data (e.g., image data that may be used to display the target and surrounding areas, including the intervening path between the array of transducer elements used to perform the imaging and the target). For example, with such generated treatment region image data, a display of images representative thereof (e.g., multiple frames of data displayed over time) may be provided such that a user (e.g., via a user interface such as represented generally in FIG. 7A; selection of the points using a point/select tool) may identify control points (block 252), such as one or more target points (e.g., points on a tumor to be ablated, points on the base of plaque to be treated, points on vessels such as vasculature, nerves, or other tissue to be treated, etc.) and/or one or more critical points (e.g., obstruction points in the path of beam, such as points on ribs, intervening fatty tissue, vessels, or other structures to be avoided, etc.).

For example, SA imaging or any other real-time DMUA imaging (e.g. coded excitation) may be used to provide display images of the treatment region and/or target region for use in identifying the control points. SA imaging is known in the art and will not be described in further detail herein. For example, such imaging is generally described in Ebbini, et al., "Dual-mode ultrasound phased arrays for image-guided surgery," *Ultrason. Imag.*, vol. 28, pp. 201-220, 2006.

With the control points, such as target points, identified (block 252), imaging (e.g., STF imaging) using one or more focused beams may be performed to measure target point directivities (e.g., as set forth in FIG. 8B, lines 13-20) and/or be performed to measure critical point directivities (e.g., as set forth in FIG. 8B, lines 21-28) (e.g., generate control image data including such directivities). A utility function for generating an "X" matrix for use in performing such routines is shown, for example, in FIG. 8B, lines 29-34.

For example, STF imaging or any other fast imaging (e.g. using multi-modal coded excitation) may be used to provide display images of the target for use in measuring, for example, target point or critical point directivities. STF imaging is known in the art and will not be described in further detail herein. For example, such imaging is generally described in Ebbini, et al., "Dual-mode ultrasound phased arrays for image-guided surgery," *Ultrason. Imag.*, vol. 28, pp. 201-220, 2006.

Generally, an SA imaging algorithm can be used to produce high quality conventional images from a given array of transducer elements. The images are useful for imaging the target region around the ThxOF (e.g., such as before and after treatment, for use in identifying target points, etc.). STF imaging on the other hand is a method usable for higher speed imaging and may employ a transmit focus, for example, with element delays identical to the HIFU therapeutic beam, but at drive levels and pulse durations at the diagnostic or sub-therapeutic level. For example, when a sub-therapeutic BIM pulse is used as the transmit pulse in STF imaging (e.g., such as between each of the therapy burst or pulses), the resulting image may show the scattering structures within the path of the pulse (e.g., allowing visualization of critical structures that may present obstacles and are to be avoided, such as rib bones when targeting the liver.

After measuring of directivities using a fast imaging scan (block 254), an optimization problem is solved (block 256) (e.g., as set forth in FIG. 8B, lines 1-5, using one or more optimization criteria) using the directivity vectors measured using the imaging process (e.g., STF imaging) to find a solution representative of, for example, the therapy signals required to generate the next therapy burst (e.g., a potential refocused burst, such as one providing different directivity for each of the plurality of transducer elements of the array).

The solution to the optimization problem (block 256) may be tested (block 258), or in other words, a test solution or pattern may be generated (e.g., as set forth in FIG. 8B, lines 6-12) to test the solution (e.g., to test the potential next therapy burst). For example, imaging (e.g., STF imaging) may be employed to generate transmit focus, for example, at one or more of the target points and/or critical points, with characteristics (e.g., such as element delays) like that of the HIFU therapeutic beam (e.g., identical to), but at diagnostic or sub-therapeutic levels (e.g., at drive levels and pulse durations at the diagnostic or sub-therapeutic levels).

Such test pattern imaging (e.g., STF imaging) ((block 258) may be used for various purposes. For example, the imaging data may be used to determine if the array focusing gain $G_T$ at one or more target points is greater than a set point gain $\Gamma_T$ (block 262). If the gain $G_T$ is greater than one or more other processes may be carried out, such as determining whether the array focusing gain $G_C$ at one or more critical points (e.g., on a rib or other intervening tissue) is less than a safety set point gain $\Gamma_C$ (block 266). If the gain $G_C$ is less than the safety set point gain $\Gamma_C$ (block 266), then the therapy burst may be delivered using the optimized solution generated (block 256).

However, if the array focusing gain $G_T$ at one or more target points is not greater than a set point gain $\Gamma_T$ (block 262), then more imaging may be performed to remeasure directivities relative to the one or more target points (block 264) (e.g., on a tumor or plaque), optimization solutions may need to be solved again (block 256) using the new measurements to determine a solution that provides the appropriate gain. Likewise, if the array focusing gain $G_C$ at one or more critical points (e.g., on a rib or other intervening tissue) is greater than a safety set point gain $\Gamma_C$ (block 266), then more imaging may be performed to remeasure directivities relative to the one or more critical points (block 260) (e.g., on a rib or other intervening tissue), and optimization solutions may need to be solved again (block 256) using the new measurements to determine a solution that provides a safe gain at the one or more critical points.

Figure 8C:
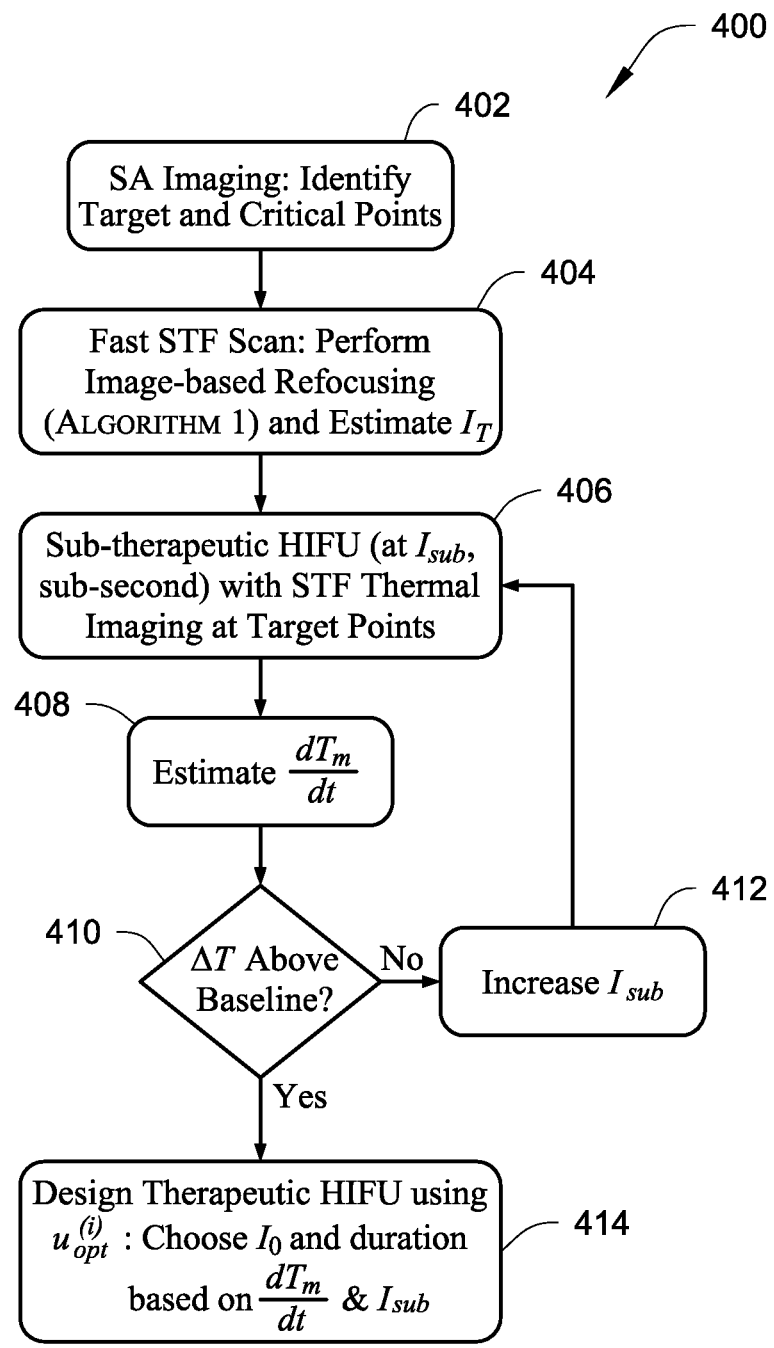

The procedure above for image-based refocusing can be modified to allow image-based calibration of thermal response to HIFU beams at sub-therapeutic levels and with sub-second durations. This allows for calibrated exposure calculation in situ for each therapy sequence. FIG. 8C shows a flowchart of an exemplary image-based method 400 to determine the exposure parameters (e.g., intensity and exposure duration) for a thermal therapy shot (plurality of bursts with intermittent imaging pulses (as shown in FIG. 3).

As shown in FIG. 8C, together with Algorithm shown in FIG. 8D, SA imaging can be used for defining target and critical points (blocks 402) and STF imaging can be used for performing image-based refocusing (block 404) as discussed with reference to FIGS. 8A-8B. In addition, the focal intensity at the target $I_T$ from knowledge of input electrical power at the DC supply, the driver/DMUA efficiency, and average attenuation and reflection measurements based on the path of the therapy beam in the target tissue volume can be estimated (block 404) (e.g., as set forth in FIG. 8D, lines 1-7). A sub-therapeutic beam with intensity level equal to a small fraction of the maximum available (e.g., 5-10 percent) and sub-second duration can be used together with STF imaging and thermal strain calculations at the target points; allowing for estimation of the thermal response to the therapy beam (block 406) (e.g., as set forth in FIG. 8D, lines 8-12). For example, the initial heating rate (IHR) can be computed (block 408), which allows for the design of the therapeutic intensity level and intensity duration in situ (block 414). This, of course, is possible if the sub-therapeutic temperature change is above the baseline (block 410) (e.g., due to tissue motion, vessel pulsation, breathing, etc.) If the sub-therapeutic temperature change is not above the baseline (block 410) then the intensity of the sub-therapeutic beam is increased (block 412) and used again with STF imaging (block 406) allowing for an estimate of thermal response to be generated (block 408). The process 400 can be designed to allow the measurement to be taken at the lowest intensity level that allows for a reliable measurement of IHR. An estimate of the maximum achievable intensity at the target location(s) can be obtained in situ. Once this value is estimated, the duration of the therapy exposure (made up of a plurality of bursts) can be set to achieve the desired therapeutic endpoint for the given shot.

The flowchart shown in FIG. 8C can also be used for identifying and refocusing on blood vessel walls, especially arteries, as these produce distinct strain patterns due to pulsation. Image-based refocusing on blood vessel can also be achieved using the process described with reference to FIGS. 8A-8B where testing the solution involves real-time strain calculation (e.g., using M2D-mode or STF imaging).

Figure 8E:
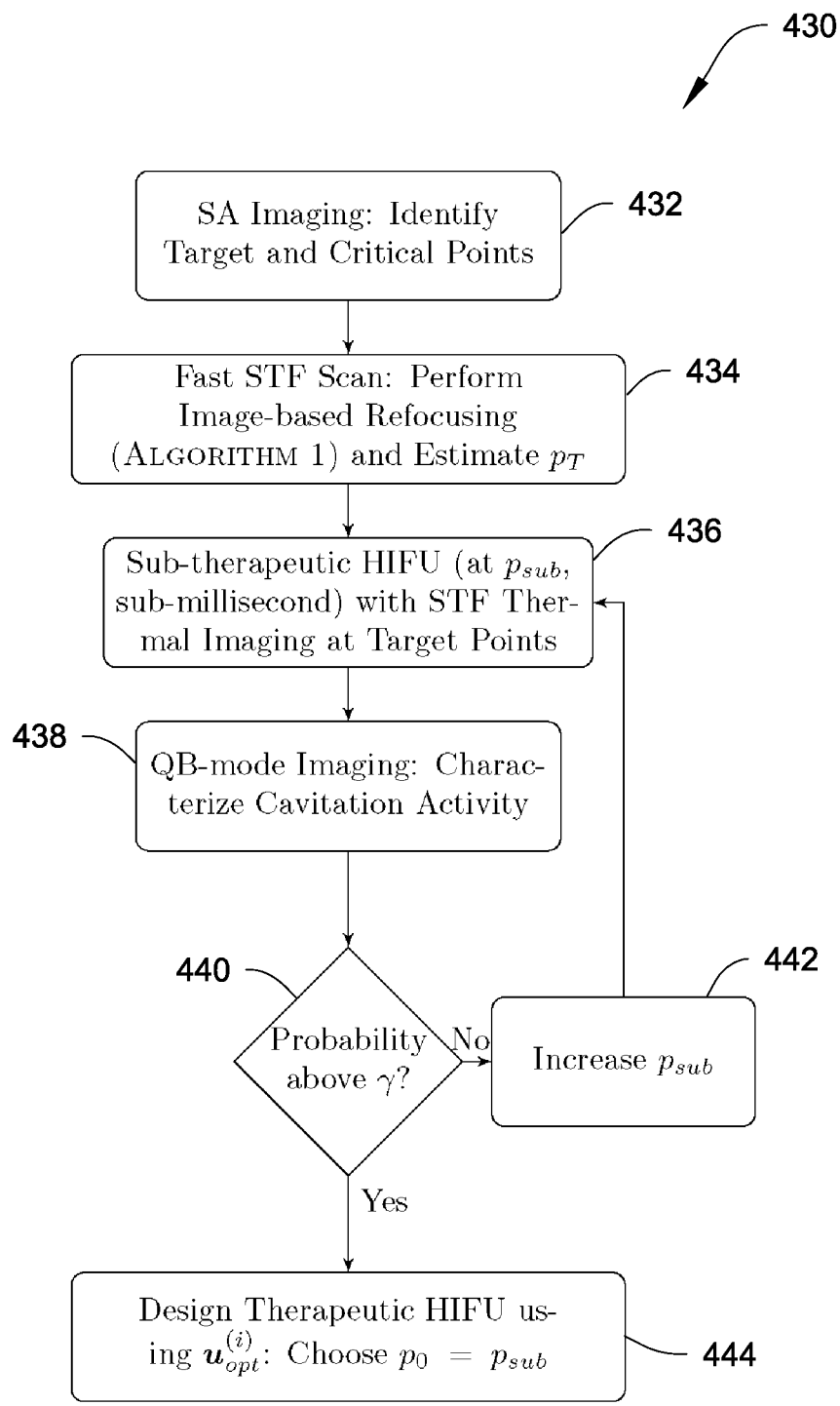

DMUAs can also be used to estimate the cavitation threshold(s) at the target location(s) in real-time as described with reference to the method 430 shown in the flowchart of FIG. 8E, together with Algorithm shown in FIG. 8F. In this case, for example, sub-therapeutic beams with sub-millisecond durations may be used with progressively increasing peak pressure levels at the focus until we reach a level where the probability of a new cavitation event per therapy burst is higher than a set threshold value. QB-mode imaging can be used to detect, localize and characterize the cavitation activity at the HIFU focus and in the path of the therapy beam. In this application, the DMUA concept has a unique advantage in the detection and localization of such events due to the high sensitivity to events and echoes from the focal spot.

Of course, both strain imaging and QB-mode imaging can be run in parallel to allow the characterization of mixed tissue response to the HIFU beam (e.g., thermal and mechanical). In this mode, which may be used by default during the actual therapy sequence, the control image data (e.g., or control sequence) that changes the intensity, duration, and spectral contents of the therapy bursts are derived from the multi-modal imaging (e.g., thermal and mechanical) in parallel.

For example, as shown in the method 430 of FIG. 8E, SA imaging may be used for defining target and critical points (blocks 432) and STF imaging can be used for performing image-based refocusing (block 434) as discussed with reference to FIGS. 8A-8B. In addition, the focal pressure at the target $p_T$ may be estimated (block 434) (e.g., as set forth in FIG. 8F, lines 1-7). A sub-therapeutic beam with pressure levels equal to a small fraction of the maximum available (e.g., 5-10 percent) and sub-second duration can be used together with STF imaging and thermal strain calculations at the target points; allowing for estimation of the pressure response to the therapy beam (block 436) (e.g., as set forth in FIG. 8F, lines 7-9). Further, QB-mode imaging may be performed to characterize cavitation activity (block 438) (e.g., as set forth in FIG. 8F, lines 10-13). For example, where the probability of a new cavitation event is higher than a set level, the estimated and test focal pressure allows for the design of the therapeutic pulses to be generated (block 444). If the sub-therapeutic probability of a new cavitation event is lower than the set probability level then the focal pressure of the sub-therapeutic beam is increased (block 442) and used again with STF imaging (block 406) in combination with the QB-mode imaging (block 438) to further test focal pressure estimates.

Example of Using Directivity Data in the Refocusing Process

As described below, experimental validation of an adaptive, image-based refocusing process using dual-mode ultrasound arrays (DMUAs) in the presence of strongly scattering objects has been implemented (e.g., representative of a noninvasive technique for therapeutic targeting of tumors seated in organs where the therapeutic beam is partially obstructed by the ribcage, e.g., liver and kidney, such as shown in FIG. 4B). The process takes advantage of the imaging capabilities of DMUAs to identify the ribs and the intercostals within the path of the therapeutic beam to produce a specified power deposition at the target while minimizing the exposure at the rib locations. This image-based refocusing takes advantage of the inherent registration between the imaging and therapeutic coordinate systems of DMUAs in the estimation of array directivity vectors at the target and rib locations. These directivity vectors may be used in solving a constrained optimization problem allowing for adaptive refocusing, directing the acoustical energy through the intercostals, and avoiding the rib locations.

Generally, the experimental validation study utilized a 1-MHz, 64-element DMUA in focusing through a block of tissue-mimicking phantom [0.5 dB/(cm·MHz)] with embedded Plexiglas ribs. Single transmit focus (STF) images obtained with the DMUA were used for image-guided selection of the critical and target points to be used for adaptive refocusing. Experimental results showed that the echogenicity of the ribs in STF images provide feedback on the reduction of power deposition at rib locations. This was confirmed by direct comparison of measured temperature rise and integrated backscatter at the rib locations. Direct temperature measurements also confirmed the improved power deposition at the target and the reduction in power deposition at the rib locations. Finally, a comparison was performed of the quality of the image-based adaptive refocusing process with a phase-conjugation solution obtained by direct measurement of the complex pressures at the target location. The adaptive refocusing process achieved similar improvements in power deposition at the target while achieving larger reduction of power deposition at the rib locations.

In this example, the problem of using DMUAs in targeting tumors in organs where the HIFU beam is partially obstructed by the ribcage, e.g., liver and kidney tumors, is addressed. This is illustrated in FIG. 4B, which shows a converging HIFU beam to a focal point in a liver tumor based on homogeneous field calculations. The challenge is to achieve a specified therapeutic dose at the target focus (within the tumor) while minimizing high-power exposure to the ribs. Heating of the ribs and their immediate surroundings is likely to be significantly higher than the normal tissue due to increased absorption of the transmitted wave, increased reflection due to the impedance mismatch, and potential mode conversion due to the tissue-solid interface. The latter could compound the heating problem due to high local absorption of shear waves in the soft tissue (see, Haken, et al., "Effect of mode conversion on ultrasonic heating at tissue interfaces," *J. Ultrasound Med.*, vol. 11, pp. 393-405, 1992).

The approach to the problem as described herein takes advantage of the inherent registration between the imaging and therapeutic coordinate systems of the DMUA by identifying (approximately) the rib and target locations from gray-scale SA or STF images. Since the same beamforming parameters are used in imaging and therapy, the estimate of the rib location is valid even in the presence of tissue aberrations. The DMUA element directivities at the rib locations and the target are estimated from the beamforming parameters. From the element directivities, array directivity vectors to the target and a set of critical points at the rib locations may be formed. The array directivity vectors provide all the necessary information for solving the constrained optimization problem of finding the complex excitation vector that achieves a specified power deposition level at the target while minimizing the power deposition at the critical points. The complex array excitation vector is used to compute the delay profiles necessary to obtain STF images of the treatment region at diagnostic levels. Backscatter from the rib locations in response to these test patterns provides feedback on the success of the refocusing algorithm in reducing the incident power at the rib locations.

DMUA imaging is important to both the identification of the critical points and the assessment of the quality of the refocused beams in terms of minimizing the power deposition at these locations. The latter represents a unique advantage of the approach described herein as STF imaging provides immediate feedback on the power deposition to the critical points. The integrated backscatter from these locations can be obtained within the acquisition time of a single STF frame time for a given test pattern (100-200 microseconds). This allows for the transmission and assessment of multiple test patterns within very short intervals $\mathcal{O}$ (1 millisecond). Thus, it is possible to obtain this diagnostic-level feedback without any significant interruption to the treatment protocol and at acquisition rates that will allow for motion tracking in real time. Such image guidance cannot be matched by other forms of image guidance using separate diagnostic imaging systems as the image guidance described herein provides key feedback features in terms of monitoring and control of the HIFU beam directly at the target and any significant critical points in its path. However, other separate diagnostic image-guidance systems in combination with the use of DMUA may also be used.

Dual-Mode Ultrasound Array Prototype for the Example.

A 64-element, 1-MHz, linear concave array on a spherical shell (100 mm radius) was designed and fabricated using HI-1 piezo-composite technology (Imasonic, Besancon, France) (see, Fleury, et al., "New piezocomposite transducers for therapeutic ultrasound," in *Proc. 2nd Int. Symp. Ther. Ultrasound,* 2002, vol. 1, pp. 428-436) for HIFU applications. Each element in the DMUA has an elevation of 50 mm and pitch of 2.0 mm. The DMUA prototype has a low $f_{number}$ of 0.8 in order to maximize the array focusing gain in the intended therapeutic operating field (ThxOF), and is sampled spatially at 1.33.3λ spacing in the lateral direction that results in grating lobes (established through computer simulation), and are kept at least 25 dB below the focus for every point within the ThxOF (see, Ebbini, et al., "Dual-mode ultrasound phased arrays for image-guided surgery," *Ultrason. Imag.,* vol. 28, pp. 201-220, 2006; and Y. Wan and E. Ebbini, "Imaging with concave large-aperture therapeutic ultrasound arrays using conventional synthetic-aperture beamforming," *IEEE Trans. Ultrason., Ferroelectr., Freq. Control,* vol. 55, no. 8, pp. 1705-1718, August 2008). In therapeutic mode, the array has shown to produce up to 250 W with efficiency ≈60% with a 37% bandwidth around the center frequency of 1.1 MHz (see, Ebbini, et al. (2006)). In pulse-echo mode without matching, the DMUA has two predominant resonance frequencies at 1.1 and 2.1 MHz. These characteristics are consistent with an earlier prototype that is described in Y. Wan and E. Ebbini, "Imaging with concave large-aperture therapeutic ultrasound arrays using conventional synthetic-aperture beamforming," *IEEE Trans. Ultrason., Ferroelectr., Freq. Control,* vol. 55, no. 8, pp. 1705-1718, August 2008; and Simon, et al., "Combined ultrasound image guidance and therapy using a therapeutic phased array," *Med. Imag.,* vol. 3341, pp. 89-98, May 1998.

Instrumentation for the Example.

A DMUA driver system was designed and built employing amplifier boards and matching circuitry allowing for pulsed-wave (PW) and continuous-wave (CW) operation at 1 MHz. A Spartan3 field-programmable gate array (FPGA) (XC3S200, Xilinx, Inc., San Jose, Calif.) was used to generate control signals and driving patterns for the DMUA prototype. The current driver runs at a 300-MHz clock allowing for ≈0.0067 $V_{dc}$ and 1.2° amplitude and phase resolutions, respectively.

The DMUA elements were connected to a transmitter and a receiver through a diplexer and a 4 64 matrix switch (Tektronix, Beaverton, Oreg.). A pulser/receiver (Panametrics 5800, GE, Fairfield, Conn.) was connected to the receive terminals on the matrix switch with the receiver connected to a 20-Msample/s 23-bit digitizer (E1437A, Agilent, Santa Clara, Calif.). For field scan measurements, a hydrophone (TNU001A, NTR, Seattle, Wash.) was used with a 30-dB preamplifier connected to a three-stage position system. The instrumentation was controlled utilizing software developed in MATLAB (Instrument Control Toolbox, Mathworks, Natick, Mass.).

Target Volume for the Example.

Figure 9A:
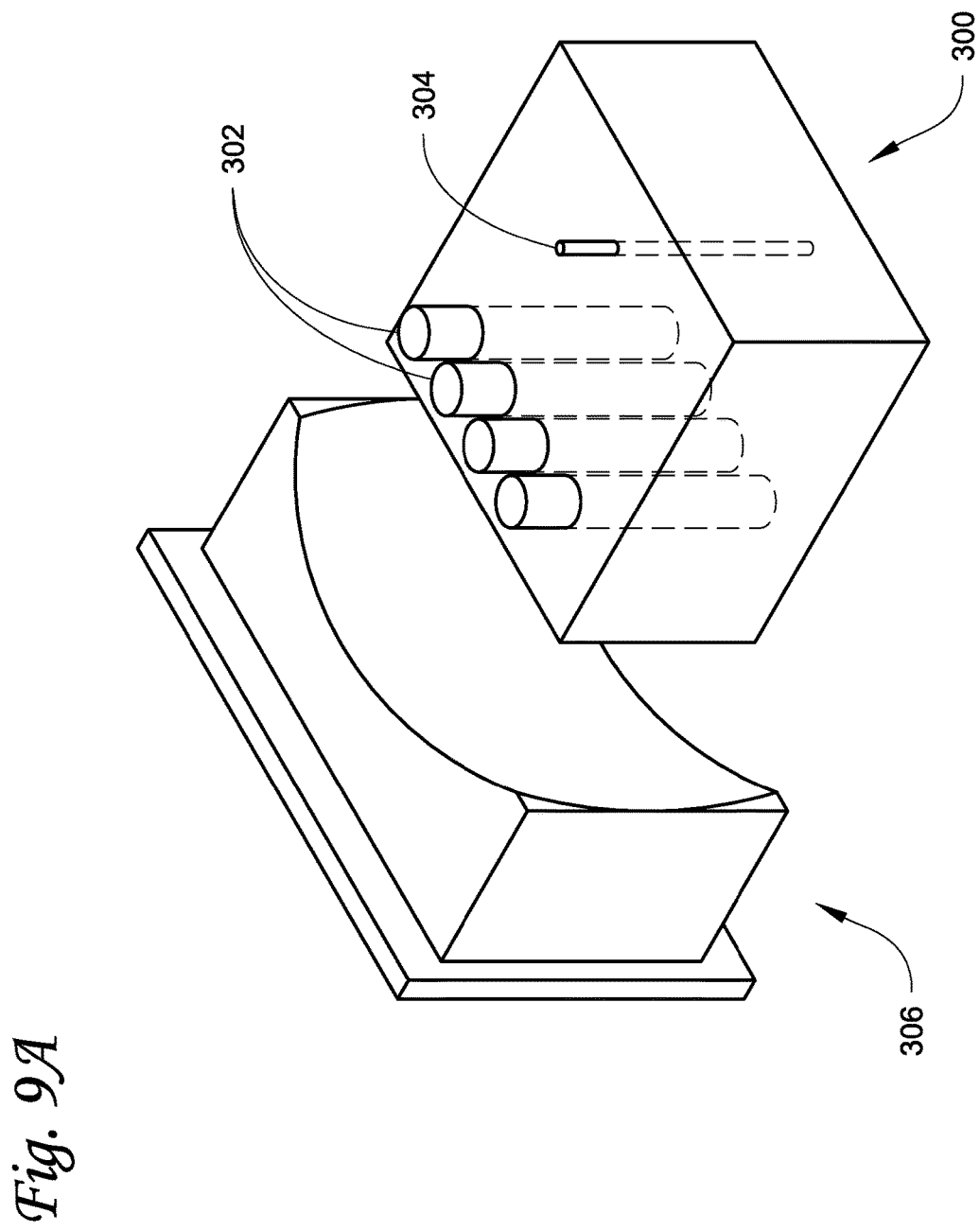

To demonstrate the feasibility of the adaptive focusing method, a tissue-mimicking phantom 300 with four embedded Plexiglas ribs 302 (9.25 mm in diameter) spaced 16 mm apart to simulate the rib cage was designed as shown in FIG. 9A. The phantom 300 measured 90 mm 70 mm 65 mm and was fabricated from gelatin, glutaraldehyde, graphite, propanal, and water, as suggested in Nightingale, et al., "On the feasibility of remote palpation using acoustic radiation force," *J. Acoust. Soc. Amer.,* vol. 110, pp. 625-634, July 2001. The phantom served as an attenuating [0.45 dB/(MHz·cm)] speckle-generating medium. The phantom is 2-D due to the nature of the 1-D 64-element array used to image and provide therapy. A 1.5-mm-diameter needle thermocouple 304 (OMEGA Engineering, Stamford, Conn.) was used as a target in the ThxOF of the DMUA 306 with an additional 1.5 mm needle thermocouple(s) placed on the rib(s) in the simulated rib cage. The thermocouple measurements were taken at a rate of 200 Hz using a data acquisition unit (34970A, Agilent, Santa Clara, Calif.).

Image Formation for the Example.

B-mode images of the phantom were formed using SA beamforming and STF imaging. STF images were taken before and after employing the refocusing algorithm using the setup described in this Example.

1) Synthetic Aperture Imaging:

SA images were obtained by using the full SA technique with two-way (transmit-and-receive) dynamic focusing (see, K. Thomenius, "Evolution of ultrasound beamformers," in *Proc. IEEE Ultrason. Symp.,* 1996, pp. 1615-1622). The SA images are among the highest quality conventional image from any given array (see, Thomenius, (1996)). The echo signal from each pixel location is computed as described in Yao, et al., "Enhanced lesion visualization in image-guided noninvasive surgery with ultrasound phased arrays," in *Proc. 23rd Annu. Int. Conf. IEEE Eng. Med. Biol. Soc.,* October 2001, vol. 3, pp. 2492-2495.

$$I(x_p, z_p) = \sum_{i=1}^{64} \sum_{j=1}^{64} A_i B_j s_{i,j} \left[ \frac{R_{ip} + R_{jp}}{c} \right] \quad (1)$$

where c is the speed of sound, $A_i$ and $B_j$ are, respectively, the transmit and receive apodization weights, $R_{ip}$ and $R_{jp}$ are, respectively, the distances from the transmitting and receiving elements to the image pixel P, and $s_{ij}(t)$ is the echo received by element j when transmitting with element i.

2) Single Transmit Focus Imaging:

STF imaging is a modified version of Equation (1) where the imaging is performed with the pulsed (one to two cycles duration) therapeutic beam as the transmit imaging focus at diagnostic intensity levels. To form a 2-D image throughout the DMUA imaging field of view, dynamic receive focusing is used, which in a uniform speckle region amounts to imaging the therapeutic beam. This imaging mode allows for the visualization (and possible characterization) of strongly scattering objects in the path of the HIFU beam (e.g., bone) at safe diagnostic levels. It provides an imaging method for surveying the treatment volume at diagnostic levels before the therapeutic HIFU beam is applied. The image formation equation for STF images is as follows:

$$I(x_p, z_p) = \sum_{j=1}^{64} B_j s_j \left[ \frac{R_{wp} + R_{jp}}{c} \right] \quad (2)$$

where $s_j$ is the received waveform at element j, and $R_{wp}$ is the minimum distance between the leading edge of the converging wavefront of the STF and pixel P at the time t=0. All other quantities are the same as their counterparts in Equation (1).

Adaptive Refocusing Algorithm Design for the Example.

The B-mode image provides feedback for the determination of target and critical points. The objective of adaptive focusing is to maximize the array intensity gain at a target point(s) $\vec{r}_T$, while minimizing across a set of critical points $\vec{r}_C$ (i), i=1, 2, . . . , $M_c$. This becomes an optimization problem, which can be solved using Lagrange multipliers or a regularized minimum-norm least squares solution (see, Botros, et al., "Two-step hybrid virtual array-ray (var) technique for focusing through the rib cage," *IEEE Trans. Ultrason., Ferroelectr., Freq. Control*, vol. 45, no. 4, pp. 989-1000, July 1998) utilizing the pseudoinverse method (see, E. Ebbini, "Deep localized hyperthermia with ultrasound phased arrays using the pseudoinverse pattern synthesis method," Ph.D. dissertation, Univ. Illinois, Urbana, 1990). In order to solve the optimization problem, the element directivities at the target and critical points must be known. This is generally not the case without direct measurements (e.g., using implantable hydrophones) or detailed computational models for wave propagation in inhomogeneous media. However, these directivities can be estimated from the beamforming parameters used in forming STF or SA images of the treatment region. From these measurements, we define a vector $h_t$ from the N-element array to the target location(s) by the array directivity vectors $h_k(\vec{r}_T)$, k=1, 2, ..., N $$h_T = [h_1(\vec{r}_T), h_2(\vec{r}_T), \ldots, h_N(\vec{r}_T)]. \quad (3)$$

Likewise, vectors from the array to each critical location $h_i$ are defined by the array directivity vectors. A matrix $H_C$ is the collection of these vectors from the critical locations $$h_i = [h_1(\vec{r}_C(i)), h_2(\vec{r}_C(i)), \ldots, h_N(\vec{r}_C(i))]. \quad (4)$$

The weighting matrix $W_c$ is formed with the matrix of critical directivity vectors and an appropriately chosen regularization parameter γ as follows:

$$W_C = [H_C^{*t} H_C + \gamma I]^{-1}. \quad (5)$$

The selection of γ was the smallest nonzero singular value of the singular value decomposition of $H_C$. This leads to the optimal complex array excitation vector for the weighted minimum norm solution as follows:

$$\hat{u} = W_c h_T^{*t} (h_T W_c h_T^{*t})^{-1} p_0 \quad (6)$$

where $p_0$ is the specified complex pressure at the target. Note that, for a single focus at the target, $p_0$ is a scalar and $h_T^{*t}$ is a row vector. For the multiple-focus case, these will be expressed as a vector of complex pressures and a matrix of element directivity vectors, respectively.

As outlined previously in this Example, the element directivity vectors at the target and critical points can be estimated from the beamforming parameters in the imaging mode. Either SA or STF imaging can be used to estimate these quantities from the imaging coordinates. STF imaging is used in the assessment of the reduction of power deposition at the critical points.

Results of Example.

The results may be described with respect to three aspects of the proposed method: 1) the identification of the target and critical points from SA or STF images and the application of the adaptive refocusing algorithm; direct temperature measurements at the target and rib locations are used to assess the resulting changes in power deposition; 2) the use of STF imaging to provide feedback about the power deposition to the ribs upon refocusing; experimental results relating the integrated back scatter from rib locations to the directly measured temperatures are presented; and 3) acoustic characterization of the HIFU beam distribution at the DMUA surface, rib plane, and target plane. The results of the image-based refocusing algorithm are compared with the results of refocusing based on direct hydrophone measurements of the element directivities at the target location. These results demonstrate that our refocusing algorithm produces well-behaved field patterns with well-behaved array excitation vectors, i.e., the inverse problem solved by Equation (6) is well posed.

Figure 9B:
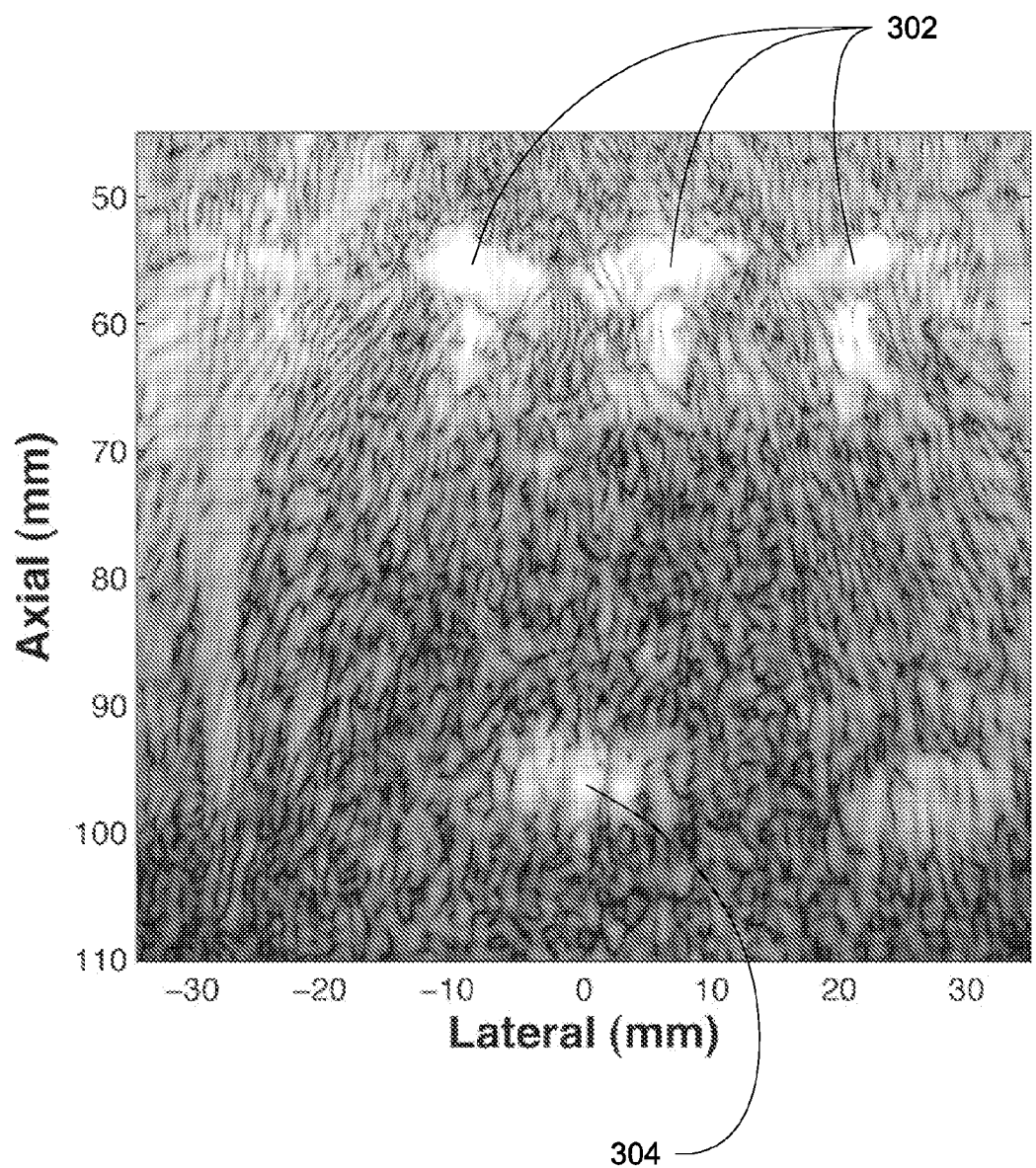

1) Image Guidance:

FIG. 9B shows the SA image (50 dB) of the phantom with the target at the geometric focus (0 mm lateral, 100 mm axial) with the ribs 302 visible at an axial distance of 55 mm. Note that the application of the algorithm does not require a strong scatterer at the target location. A thermocouple 304 is used as a scatterer at the target location to demonstrate the relation between changes in echogenicity and temperature change upon refocusing. It is interesting to note that the image of the target in this image appears quite diffuse with high lateral sidelobes. This is due to beam distortions that were not taken into account in the SA beamforming algorithm. Compared to the image of the target in the absence of the ribs (not shown), this distortion is quite pronounced as one might expect. Nonetheless, the image suggests that the DMUA still achieves certain level of focusing around the target. Based on the image shown, four critical points at the (approximate) center of each rib were chosen in addition to the target point. The matrix Hc was formed by using the array directivity vectors in the vicinity of each critical point. Specifically, for each critical point, we have computed the array directivity vectors for a set of points covering the extent of the corresponding rib in the lateral direction with spatial sampling of λ/2, where λ is the operating wavelength in the soft tissue (1.5 mm in this case). The array directivity vector at the target $h_T^{*t}$ is also obtained from the beamforming parameters at the target point, i.e., without correcting for the inhomogeneity presented by the ribs.

The estimated array directivity vectors were used to refocus the DMUA at the target in the presence of the ribs. Before applying the HIFU beam for therapeutic heating, the DMUA was driven with a diagnostic-level excitation vector resulting from Equation (6) in the pulse mode to obtain STF images of the target medium upon refocusing. FIG. 9C shows STF images (50 dB) of the target region and the ribs using: 1) the geometrically focused HIFU beam (assuming homogeneous medium) and 2) the refocused HIFU beam according to Equation (6). The two images are normalized to the same maximum intensity for comparison purposes. One can see that the echogenicity of the ribs is lower in the refocused image with respect to the echogenicity of the target.

Figure 9D:
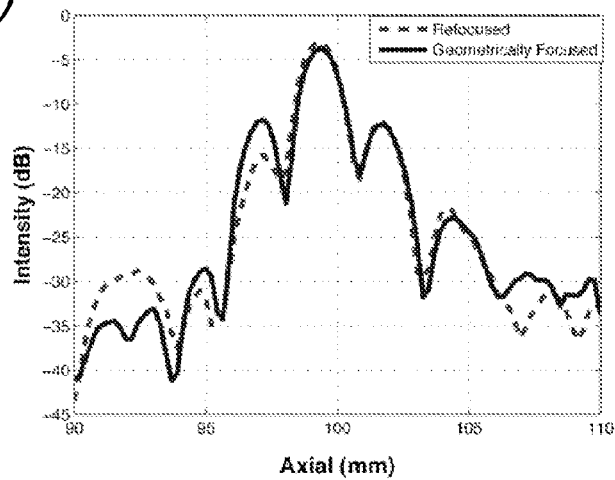
Figure 9D:
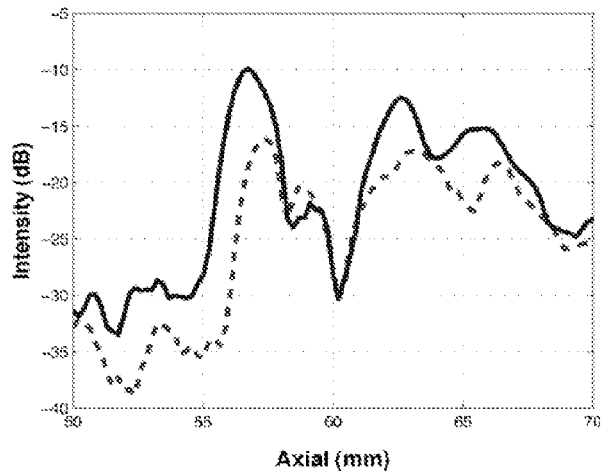
Figure 9D:
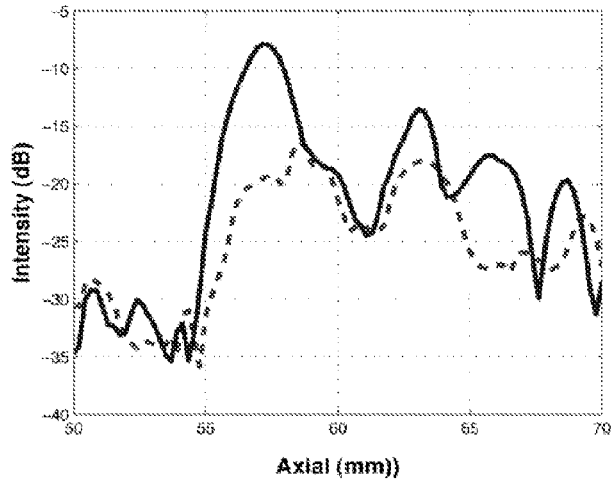

FIG. 9D further illustrates the change in relative echogenicity at the middle rib locations upon refocusing. The line plots show the echogenicity profiles along an axial line through the target (FIG. 9D(a)) and two axial lines through the two central ribs (FIGS. 9D(b) and 9D(c)). The solid lines are obtained from the image in FIG. 9C(a) and the dashed lines are obtained from FIG. 9C(b). The results clearly show that while the relative echogenicity of the target is the same for both HIFU beams, the echogenicity of the ribs drops measurably (6-10 dB) upon refocusing. This result suggests that STF imaging can be used as an early indicator of the success of the refocusing algorithm in lowering the power deposition at the rib locations.

To further demonstrate the usefulness of the feedback provided by the STF imaging using diagnostic-level HIFU beams, a summary of the experimental results of refocusing when targeting points 5 and 10 mm laterally off the DMUA geometric center is also shown below.

Figure 9E:
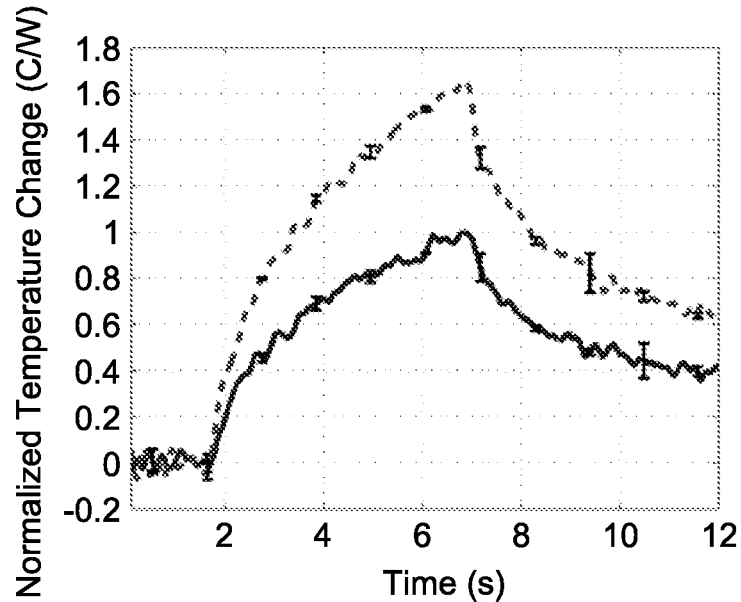
Figure 9E:
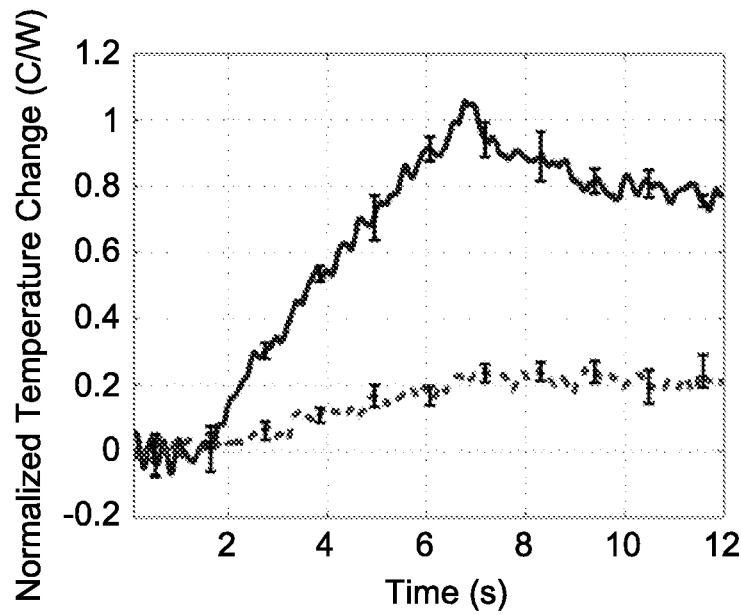

2) Direct Temperature Measurements:

Temperature measurements were taken at the target and rib location(s) before, during, and after a 4-s HIFU exposure. This was done for both the geometrically steered and refocused driving patterns for all three target locations given before. For each case, the dc power delivered to the DMUA was normalized for the adaptively and geometrically focused driving patterns. Furthermore, to show repeatability, each measurement was taken a minimum of five times. The results shown in FIG. 9E show a comparison of normalized temperature change (and variance) at the target and one rib location for the geometrically focused and adaptively refocused driving patterns when the target is at the geometric focus. The temperatures are normalized with respect to the maximum temperature at the target resulting from the geometrically focused HIFU beam. One can see that using the refocused HIFU beam increased the temperature at the target by 65%. At the same time, it decreased the temperature at the rib by nearly 80%. In this case, the target to rib temperature ratio $T_T/T_{rib}$ was increased from 0.94 to 6.1. The Table of FIG. 9F shows the relative temperature change across both the middle ribs as well as at the target location for the cases when the target point is located at (5, 100) and (10, 100) mm, respectively. These results show that the relative temperature increase at the target upon refocusing varies depending on the location of the target with respect to the ribs. Similarly, the degree of relative decrease in temperature at the ribs also varies for the different cases. It is, however, important to note that the trends shown by these results are quite general in that the application of the adaptive refocusing always results in increasing the power deposition at the target and reduction in power deposition at the ribs.

3) Summary of Temperature and Echogenicity Changes:

The STF imaging results shown before suggest that changes in the echogenicity at the target and rib locations upon adaptive refocusing agree with the measured temperature changes at these locations. The Table of FIG. 9F summarizes these changes in terms of the temperature ratio $T_T/T_{rib}$ for each case. The measured echogenicity from the normalized STF images for each case is also reported. For the adaptive refocusing cases, the relative change in target to rib echogenicity in decibels is also shown to be defined as follows:

$$\Delta E = 10 \log_{10}\left[\frac{E_{TR}/E_{TG}}{E_{RR}/E_{RG}}\right]$$

where $E_{TG}(E_{RG})$ and $E_{TR}(E_{RR})$ are the integrated backscatter values from the target (rib) location due to the geometrically focused and the adaptively refocused HIFU beams. The integrated backscatter measurement is formed from the average of five beamformed A-lines centered at the location of interest. One can see that the relative changes in echogenicity appear to have the same trend as the relative changes in temperature ratios. While this is currently not a quantitative measurement, it suggests a monotonic relationship between temperature change (a measure of power deposition) and the integrated backscatter. This relationship allows the use of STF to provide immediate feedback from the target and rib locations on the increase/decrease in power deposition upon refocusing. Given that the frame times of STF imaging is in the 100-200 microsecond range, this form of feedback allows for testing multiple refocused beams during very short intervals on the order of $\mathcal{O}$ (1 millisecond) and choose the best in terms of increasing power deposition at the target while decreasing the power deposition at the rib locations in the path of the HIFU beam.

Image-Based Feedback on Changes in Power Deposition for the Example.

The selection of the critical points from gray-scale images involves some level of uncertainty due to the following reasons. 1) The lateral resolution of the imaging system is limited (1.2 mm for the DMUA prototype used). 2) The geometry of the obstacle with respect to the DMUA produces angular scattering functions that may obscure the shape of the obstacle. This is especially true for our DMUA, which has poor axial resolution of ≈2.6 mm. As can be seen from the images shown before, even a strongly scattering object appears amorphous, especially in STF images. 3) The surrounding speckle from the soft tissue may drown the echoes from the obstacle, except for the strongest specular reflection. This is clearly the case in STF images, but is less so in the SA image shown, which appears to capture the top surface of the ribs.

Due to the aforementioned reasons, it may be necessary to test several "refocused" HIFU beams accounting for the uncertainty in the obstacle locations. To demonstrate this, the estimated position of the critical points associated with one of the middle ribs when focusing at (5, 100) mm was varied. The critical point corresponding to the right rib was used and its position varied by ±0.5 and ±1 mm. Equation (6) was used to find the excitation vector corresponding to each one of these critical points. These excitation vectors were used to obtain six STF images of the treatment region to measure the changes in rib echogenicity corresponding to each driving vector. Finally, the different excitation vectors in the 4-s therapeutic mode described before were applied and the resulting temperature profiles at the target and the rib were recorded. The results demonstrated the feasibility of using STF imaging for providing feedback on reduction/increase in power deposition at a given obstacle resulting from the use of different HIFU beams in focusing at a specific target. This feedback is practically instantaneous. For example, all six STF images can be obtained in approximately 900 microseconds. With dedicated beamforming and image processing hardware/software, it is possible to select the most appropriate pattern (in terms of maximum power deposition at the target with minimum power deposition at the critical point) within milliseconds. This will have negligible effect on the treatment protocol and will still allow for real-time treatment control, including motion tracking.

Acoustic Field Characterization for the Example.

Additional insight on the workings of the refocusing algorithm was provided by direct measurement of the acoustic field profiles in the rib and target planes for different HIFU excitation vectors in the presence of the ribs. To do this, the ribs were placed in front of the DMUA, as shown in FIG. 4B, without the speckle-generating phantom present. A needle hydrophone was used to measure the intensity profiles directly behind the ribs (as seen from the DMUA) and in the target plane in degassed water (3 ppm dissolved oxygen). Three HIFU beams were used: 1) a geometrically focused beam (0, 100); 2) an adaptively focused beam using (6); and 3) a phase-conjugation solution obtained by measuring the complex pressures from the DMUA elements at the target location. Phase conjugation is the spatial matched-filter solution (see, Seip, et al., "Dynamic focusing in ultrasound hyperthermia treatments using implantable hydrophone arrays," *IEEE Trans. Ultrason., Ferroelectr., Freq. Control*, vol. 41, no. 5, pp. 706-713, September 1994), which maximizes the array gain at the measurement point. This measurement amounts to measuring the DMUA element directivities directly at the target point. This is the CW equivalent of the time-reversal solution previously proposed (see, Aubry, et al., "Transcostal high-intensity-focused ultrasound: Ex vivo adaptive focusing feasibility study," *Phys.*

Med. Biol., vol. 53, pp. 2937-2951, 2008; M. Fink, "Time reversal of ultrasonic fields. I. basic principles," *IEEE Trans. Ultrason., Ferroelectr., Freq. Control*, vol. 39, no. 5, pp. 555-566, September 1992; Wu, et al., "Time reversal of ultrasonic fields. II. Experimental results," *IEEE Trans. Ultrason., Ferroelectr., Freq. Control*, vol. 39, no. 5, pp. 567-578, September 1992; and Prada, et al., "The iterative time reversal process: Analysis of the convergence," *J. Acoust. Soc. Amer.*, vol. 95, pp. 62-71, 1995). This solution may serve as a standard for the refocusing problem described in this paper as it incorporates the full knowledge of the array directivity at the target (subject to measurement error).

FIG. 9G shows the results of this experiment for the three driving patterns. FIG. 9G1 shows the focal plane intensity profiles for the geometrically focused (solid), the adaptively refocused (dotted), and the phase-conjugation refocused (dashed-dotted) HIFU beams. The intensity profiles just behind the ribs (as, seen from the DMUA) are shown in FIG. 9G2. All patterns are normalized with respect to the peak intensity of the geometrically focused HIFU beam in the focal plane. One can see that both the adaptively refocused and the phase-conjugation refocused HIFU beams nearly double the focal intensity for the same dc power input to the DMUA. This is a significant improvement in the array gain compensating for the effects of the ribs. Comparison between the two refocused beam profiles not only shows the general agreement between them, but also reveals some subtle differences. In particular, the adaptively refocused HIFU beam relies more on the intercostals in producing the focused field at the target while the phase-conjugation refocused HIFU beam appears to allow for relatively higher partial transmission through the ribs, as shown in FIG. 9G1. The relative distributions of power in the rib plane due to the different refocusing algorithms must be compared in terms of their ability to achieve the specified therapeutic endpoint at the target while minimizing the heating of both the ribs and the intercostals. One embodiment of the adaptive refocusing approach described herein is based on treating the ribs as critical structures where the power deposition is to be minimized, thus favoring the transmission through the intercostals. This criterion can be modified to allow for some partial transmission through the ribs if it is determined that it will be safe to do so at power levels necessary to achieve a specified intensity gain at the target.

Comparing the focal plane intensity profiles, one observes increased grating lobe levels for all three patterns, but especially for the adaptively refocused HIFU beam. These grating lobes are not due to the DMUA elements sampling. They are due to the presence of a "virtual array" in the intercostals due to the partial blocking of the HIFU beams by the ribs. The height of the grating lobes can be explained by the relative level of partial blocking.

Finally, examination of the typical magnitude and phase distributions of the DMUA excitation vector resulting from the application of adaptive refocusing according to Equation was also performed. These distributions resulted from refocusing the DMUA at (5, 100) mm in the presence of the Plexiglas ribs as described before. All the array elements were activated, even those elements shadowed by the ribs. This is due to the fact that all elements are needed to obtain the highest level of destructive interference at the rib locations while maximizing constructive interference at the target. Further, the adaptive refocusing based on Equation (6) was compared with a ray tracing solution, which shuts off the DMUA shadowed by the ribs. The results have shown that the ray tracing solution consistently results in higher power deposition at the rib location. Therefore, our adaptive refocusing algorithm intelligently uses all the degrees of freedom (DMUA elements) to meet the constraints at the target while minimizing the power deposition at the ribs.

Discussion Regarding the Example.

The results of the Example are applicable to practical applications based on imaging with DMUAs. It has been shown that DMUA imaging in the tissue and speckle-generating quality assurance phantoms produces images that can be compared with those obtained using diagnostic scanners with the following differences. 1) A typical DMUA with 30% fractional bandwidth produces images with axial resolution of approximately 2.6 mm, which is significantly poorer than diagnostic probes (generally in the submillimeter range). 2) Due to their large aperture and concave geometry, DMUAs produce excellent lateral resolution typically around 1 mm. DMUA image quality can be improved using coded excitation and pulse compression inverse filtering together with explicit accounting to some of the element and array geometry in beamforming. However, even without these improvements, the feasibility of identifying strongly scattering structures like the ribs, even when they are embedded in tissue-mimicking phantoms has been demonstrated. Both our SA and STF imaging have been largely based on conventional beamforming, and therefore represent a form of backscatter imaging. With the large-aperture array, SA imaging captures the proximal edge of the ribs, which may allow for reasonable selection of the critical points associated with each obstacle and its extent from the specular reflections. STF images, on the other hand, currently do not capture the geometry of the obstacle, but only the critical point obtained from the dominant specular reflection. This can be appreciated by comparing the specular reflections from the ribs in the SA image in FIG. 9B and the STF image in FIG. 9C. One can see a more contiguous specular reflection from the proximal edge of each rib in the SA image as compared to the spot-like specular reflections in the STF image. In practice, this may mean that one may use SA imaging for the initial survey of the scene to estimate the extent of each obstacle and perform the real-time tracking of the critical point associated with each obstacle using STF imaging. As illustrated herein, uncertainty in the location of the critical point can be overcome by using several test patterns and choosing the one that minimizes the backscatter from the rib location.

The adaptive refocusing algorithm discussed herein achieves a specified power level at the target while minimizing the power level at the ribs. Comparisons with the phase-conjugation method for refocusing show that both approaches improve the DMUA focusing gain at the target and direct the power flow into the intercostals with minimum differences. These differences primarily stem from the different levels of partial transmission through the ribs, but may be attributed to other factors. For example, the adaptive refocusing method uses the uncorrected array directivity vector $h_T$ as opposed to the measured directivity vector used by the phase conjugation method.

There are several variations on the current adaptive refocusing algorithm that may be used. For example, a two-step procedure that performs the synthesis problem in the soft tissue first from a virtual array within the intercostals to the target followed by a second synthesis problem from the physical DMUA to the virtual array. This approach will also allow one to incorporate the partial transmission through the ribs as part of the optimization problem (by extending the virtual array to the distal edges of the ribs). In order to do this meaningfully, however, this approach needs to be developed along with a reliable forward scattering model phase and amplitude distortions due to propagation through bone. The two-step approach may also useful in designing (or configuring) an appropriate DMUA for a given target (defined by the tumor depth and size) and an available discontinuous acoustical window.

Experimental verification of an image based, adaptive transthoracic refocusing algorithm has been described for improved therapeutic targeting of tumors in organs where the HIFU beam is partially obstructed by the ribcage. The results have demonstrated the feasibility of controlling the flow of acoustical power through the intercostals to achieve a specified level of power deposition at the target while minimizing the power deposition at the ribs (e.g., critical points). We have also shown that gray-scale STF images provide suitable feedback on the improved quality of the adaptively refocused HIFU beams in terms of lowering the power deposition at the rib locations. This form of feedback is fast (100-200 μs per STF frame) and spatially accurate, especially at the proximal side of the ribs. This allows for several HIFU beams targeting the same point to be tested at sub-therapeutic levels below 1 ms to determine which beam produces minimal heating of the ribs in the path of the HIFU beam. In addition, linear and nonlinear imaging methods using DMUAs can be used to assess tissue response to HIFU lesion formation. Therefore, DMUA imaging provides the necessary feedback to refocus HIFU beams in the presence of strongly scattering structures as well as the assessment of the target tissue to the application of the HIFU beam. This feedback is valuable due to the inherent registration between the imaging and therapeutic coordinate systems for DMUAs (e.g., useful for providing noninvasive, image-guided surgery).

Example of Using Thermal Response Data in the Refocusing Process

As described below, a system for the real-time generation and control of multiple-focus ultrasound phased-array heating patterns is presented. Generally, the system employs a 1-MHz, 64-element array and driving electronics capable of fine spatial and temporal control of the heating pattern. The driver is integrated with a real-time 2D temperature imaging system implemented on a commercial scanner. The coordinates of the temperature control points are defined on B-mode guidance images from the scanner, together with the temperature set points and controller parameters. The temperature at each point is controlled by an independent proportional, integral, and derivative (PID) controller that determines the focal intensity at that point. Optimal multiple-focus synthesis is applied to generate the desired heating pattern at the control points. The controller dynamically reallocates the power available among the foci from the shared power supply upon reaching the desired temperature at each control point. Furthermore, anti-windup compensation is implemented at each control point to improve the system dynamics. In vitro experiments in tissue mimicking phantom demonstrate the robustness of the controllers for short (2-5 sec) and longer multiple-focus HIFU exposures. Thermocouple measurements in the vicinity of the control points confirm the dynamics of the temperature variations obtained through noninvasive feedback.

Phased array applicators offer unparalleled level of spatial and temporal control over the heating pattern, including simultaneous heating at multiple-focus locations. This has many potential advantages in thermal therapy, including reduction in treatment time, improved localization of therapeutic effects to the target volume, compensating for heterogeneous blood perfusion, etc. Phased array drivers are capable of dynamic control of heating patterns using a variety of man-machine interfaces with millisecond resolution. Real-time temperature control algorithms with spatial and temporal resolutions matching those of the drivers are used to realize the full potential of phased array technology in thermal therapy. Furthermore, to preserve the noninvasive nature of the treatment, the algorithm utilizes a noninvasive method for measuring temperature change within the treatment volume.

Various ultrasound thermography methods may be used. For example, a speckle tracking based method implemented in real-time using a diagnostic scanner and general-purpose graphics processing unit (GPGPU) may be used. In addition, real-time control of a 64-element dual-mode ultrasound array (DMUA) system may be accomplished. For example, a temperature imaging system may be integrated with the DMUA driver allowing for the selection of multiple temperature control points within a treatment volume (as seen on the B-mode real-time images). The spatially distributed feedback available through noninvasive real-time ultrasound thermography allows for real-time control of spatially distributed multiple-focus phased-array heating patterns.

As described in this example, an ultrasound phased array system for image-guided thermal therapy applications with illustrative examples of multiple-focus heating patterns is provided. Further, a multipoint (multiple-focus) control algorithm with emphasis on multiple-focus heating patterns is provided. In particular, an implementation is described of dynamic power reallocation among different focal points upon reaching set points. Examples of long-exposure (used in hyperthermia) and short-exposure (used in ablative therapy) multiple-focus patterns are given and their potential applications are discussed.

Experiment Setup for the Example.

The setup shown in FIG. 10A was used to generate the results presented herein for this example. A 1-MHz, 64-element ultrasound phased array 350 was used for generating single and multiple focus heating patterns (Imasonic, Inc., Voray sur lOgnon, France). A tissue mimicking phantom 352 fabricated according to the procedure described in Nightingale, et al., "On the feasibility of remote palpation using acoustic radiation force," *J. Acoust. Soc. Amer.*, vol. 110, pp. 625-634, July 2001 was used as a target. A linear array imaging probe 354 (LA14-5) was used to acquire ultrasound images for guidance and noninvasive thermography. A needle thermocouple 356 (TMQSS-020U-6) was used to monitor the temperature rise in the phantom in response to the array heating patterns. The needle shaft was carefully positioned at the boundary of the imaging slice to minimize distortion of the RF data collected using the imaging probe 354.

1) Array Driver and Control System:

The therapeutic array driver employs a 1000 W programmable DC power supply (Agilent 6030A). The supply is capable of providing DC voltage, $V_{DC}$ of up to 200 V and a maximum current up to 17 A (within the 1000 W limit). The DC supply feeds the 64-channel amplifier driving the array elements through series matching inductors (an updated version of the system described in ES Ebbini and CA Cain, "Experimental evaluation of a prototype cylindrical section ultrasound hyperthermia phased-array applicator," TREE TRANSACTIONS ON ULTRASONICS FERROELECTRICS AND FREQUENCY CONTROL, vol. 38, no. 5, pp. 510-520, September 1991. The supply voltage, together with the matching circuit and the power factor of a given array element, determine the maximum particle velocity achieved on the surface of that element, $U_{max}$. The current drawn from the supply is determined by the amplitude distribution of the active array channels. This is subject to the maximum current limitation, a user-specified value up to 17 A for the DC supply used in these experiments. The instantaneous current value supplied by the Agilent 6030A was interrogated during each heating experiment at a sampling rate of 12.5 Hz with time stamp information. For the experiments described in this example, $V_{DC}$ was set to achieve a desired heating rate at a given control point in the heating pattern, e.g., 1_C/s for typical long exposure experiment. This may be adjusted up or down to meet certain requirements on the heating rate as may be dictated by the application, e.g. slower values in drug activation and larger values in high-temperature applications.

2) Multiple-Focus Synthesis:

Phase and amplitude control is achieved through a 200-MHz FPGA-based digital control circuit (see, Ebbini, et al., "Dual-mode ultrasound arrays for image-guided surgery," Ultrasonic Imaging, vol. 28, pp. 65-82, April 2006) allowing for $0.01V_{DC}$ and 1.8° amplitude and phase resolution, respectively. The phase and amplitude distributions are obtained using the optimal pattern synthesis method introduced in ES Ebbini and CA Cain, "Multiple-focus ultrasound phased array pattern synthesis—Optimal driving signal distributions for hyperthermia," IEEE TRANSACTIONS ON ULTRASONICS FERROELECTRICS AND FREQUENCY CONTROL, vol. 36, no. 5, pp. 540-548, September 1989. The weighted minimum-norm solution described in ES Ebbini and CA Cain (1989) was used to obtain an equal-magnitude distribution, which achieves the highest driving efficiency from the DC supply. Mathematically, the pressures at a set of M control points are specified as the vector $p=[p_1\ p_2\ \ldots\ p_M]'$, where [.]' indicates matrix (vector) transpose. For an N-element array, an M×N matrix propagation operator, H, is defined with the mth element defining the directivity of the nth array element at the mth control point. The N-element array excitation vector is obtained through a weighted minimum-norm solution, $$\hat{u} = WH^H(HWH^H)^\dagger p \qquad (1)$$

where W is a positive definite weighting matrix with [.]' and [.]$^\dagger$ representing, respectively, the Hermitian transpose and the regularized pseudo inverse.

Temperature Measurements for the Example

1) Direct Measurements:

A needle thermocouple (Omega, Stamford, Conn.) connected to a GPIB-controlled data acquisition system (Agilent 34970A) was used to directly measure the temperature at one of the control points for verification purposes. The needle shaft was inserted into the phantom in parallel to both the imaging and therapeutic array faces. It was carefully placed at the edge of the imaging slice of the diagnostic system with the junction just past the (geometric) focal plane of the therapeutic array. The raw thermocouple readings were acquired at a rate of 100 Hz and stored in the Agilent 34970A buffer. The sampled data was uploaded to the controlling workstation at the conclusion of each heating experiment. The thermocouple data shown in the Results of this example below are filtered using an 8-point moving average.

2) Noninvasive Thermography:

the LA14-5 linear array probe on the Sonix RP was used to acquire 2D RF data in real-time. The system described in D. Liu and E. S. Ebbini, "Real-Time 2-D Temperature Imaging Using Ultrasound," IEEE TRANSACTIONS ON BIOMEDICAL ENGINEERING, vol. 57, no. 1, pp. 12-46, January 2010 was used to obtain 2D temperature change images at 99 fps. The estimated temperature values were determined based on the measured material properties of the tissue-mimicking phantom used according to the algorithm described in Simon, et al., "Two-dimensional temperature estimation using diagnostic ultrasound," IEEE Trans. Ultrason., Ferroelect., Freq. Contr., vol. 45, pp. 989-1000, July 1998; and Liu and Ebbini, (2010). The temperature imaging equation used:

$$\Delta T(z) = \frac{c(T_0)}{2}\left[\frac{1}{\beta - \alpha}\right]\frac{\partial}{\partial z}(\delta t(z)), \qquad (2)$$

where $\alpha=(\partial d(T)/\partial T)/d(T)$ and $\beta=(\partial c(T)/\partial T)/c(T)$. For the phantom material used to obtain the experimental results shown in this example, FIG. 10C shows the speed of sound vs. temperature curves used to determine the material constant suggested in Simon et al. (1998). This result shows that the temperature dependence of the speed of sound in the phantom material is consistent with many in vitro tissues.

Real-Time Feedback Control for the Example.

For the experiment setup described in FIG. 10A, the coordinates of the control points (e.g., target points for focus of therapy) were placed on the line of intersection between the imaging (xz) and therapeutic (xy) planes. Two control points or foci were defined for each heating experiment to illustrate the operation of real-time temperature control, but the methods described herein apply to larger number of foci. A proportional integral (PI) controller represented by the block diagram shown in FIG. 10D was used to determine the power level at each control point. Anti-windup compensation was implemented digitally using a limiter in the integral component path as shown in FIG. 10D. It functions by preventing the integral term from accumulating above or below pre-determined bounds (see, C. Bohn and D. P. Atherton, "An analysis package comparing pid antiwindup strategies," Control Systems Magazine, IEEE, vol. 15, no. 2, pp. 34-40, April 1995). This technique is widely used in conjunction with PI control applications where the control output (CO) values are subject to upper or lower limits, or both. In this case, the CO cannot be negative, which sets a lower limit of zero. In addition, the power delivered to any control point is limited by a maximum value determined by the available power at the supply and/or power allocation scheme to the individual control points. The set point temperatures at the control points can be defined independently as long as the control points are sufficiently spaced. There are two factors guiding the judicious choice of control points: 1) The conditioning of the propagation operator in Equation (1) (see, E. Ebbini, Deep Localized Hyperthermia with Ultrasound Phased Arrays Using the Psudoinverse Pattern Synthesis Method, Ph.D. thesis, University of Illinois, 1990), and 2) the thermal properties of the medium, together with the duration of the heating. It should be noted that the multipoint control algorithm described herein is fundamentally different from the control algorithm described in Seip, et al., "Noninvasive real-time multipoint temperature control for ultrasound phased array treatments," IEEE TRANSACTIONS ON ULTRASONICS FERROELECTRICS AND FREQUENCY CONTROL, vol. 43, no. 6, pp. 1063-1073, November 1996 (which describes an algorithm for multipoint temperature control by changing the dwell times of precomputed single- or multiple-focus patterns, i.e. no modification of the driving signal distributions). In this example, the real-time control of multiple-focus heating patterns by resynthesizing the heating patterns according the demand of the HD controllers associated with the control points is described. This mode is well-suited for the relatively short exposures used in ablative thermal therapies.

1) Efficient Generation of Multiple-Focus Heating Patterns:

As discussed in Ebbini and Cain, "Multiple-focus ultrasound phased array pattern synthesis—Optimal driving signal distributions for hyperthermia," IEEE TRANSACTIONS ON ULTRASONICS FERROELECTRICS AND FREQUENCY CONTROL, vol. 36, no. 5, pp. 540-548, September 1989, the pseudo inverse solution to the pattern synthesis problem often results in driving signal vectors with variable amplitude distribution. This may limit the power deposition at the focal spots when the voltage across some of the array elements is at or near the maximum value determined by $V_{DC}$ and the matching circuit topology (see, Ebbini and Cain, "Experimental evaluation of a prototype cylindrical section ultrasound hyperthermia phased-array applicator," IEEE TRANSACTIONS ON ULTRASONICS FERROELECTRICS AND FREQUENCY CONTROL, vol. 38, no. 5, pp. 510-520, September 1991). The weighting algorithm described in Ebbini and Cain (1989) allows for compressing the dynamic range of the magnitude distribution to improve the array driving efficiency defined by $$\eta_A = \frac{\sum_{n=1}^{N}|u_n|^2}{NU_{max}^2} \times 100\%, \quad (3)$$

where $U_{max}$ is the maximum achievable value of the driving signal on the surface of the array. A maximum efficiency of 100% indicates equal-amplitude (or phase-only) synthesis, which is highly desirable provided the phase distribution does not result in evanescent modes on the surface of the array. It is shown in Ebbini and Cain (1989) that the improved efficiency achieved using the iterative weighting algorithm results in corresponding improvement in power deposition at the foci.

2) Dynamic Power Reallocation:

The multiple-focus synthesis problem, as given in Equation (1), gives the complex particle velocities at the surface of the array elements in terms of the specified complex pressures at the control points. The complex pressures at the control points can be determined from the desired initial heating rate at the mth point, $$\frac{dT_m}{dt} = \frac{1}{\rho C}Q_m = \frac{\alpha}{\rho^2 cC}|p_{md}|^2, \quad (4)$$

where $\rho$, c, C and $\alpha$ are the density, speed of sound, specific heat, and absorption, respectively. The complex particle velocity distribution obtained using Equation (1) is directly related to the terminal voltage, which determines the current supplied by the DC supply to the amplifier circuits driving the array elements. The maximum particle velocity, $U_{max}$ may be determined by the transducer technology. For example, the therapeutic array described in this example is designed to provide a maximum surface intensity of 5 W/cm². The driving circuitry may limit the maximum achievable particle velocity, e.g. saturation current in matching inductors or current limitation of the amplifier transistors. Finally, the DC supply may limit the total current supplied to the array driver. For these reasons, $U_{max}$ must be predetermined based on the requirements of the therapy and the capabilities and/or limitations of the driving circuitry.

Knowledge of the initial heating rate and approximate tissue properties in the treatment region, together with the propagation model allow for the computation of the needed power deposition at each focal spot. Assuming an initial power distribution among the control points (e.g. equal distribution), the total acoustic power requirement can be determined. The DC supply power can be determined from the acoustic power and the efficiency of the driving circuitry. For the system used in this example, $V_{DC}$ and $I_{DCmax}$ are set on the DC supply at the outset of the heating experiment. This defines the available DC power, which will not be exceeded during the experiment.

The above considerations, coupled with the PID control strategy at the individual control points, necessitate a dynamic power reallocation strategy for minimizing the time to reach the set point temperatures. Simply stated, the controller needs to be aware of the power requirement for each focus to maximize the heating rate at the points that have not yet reached the set point temperatures. Once a set point temperature has been reached, the power delivered to the focus controlling it can be significantly reduced, leaving a larger fraction of the supply power to be directed to the remaining foci controlling points below their set point temperatures.

Figure 10B:
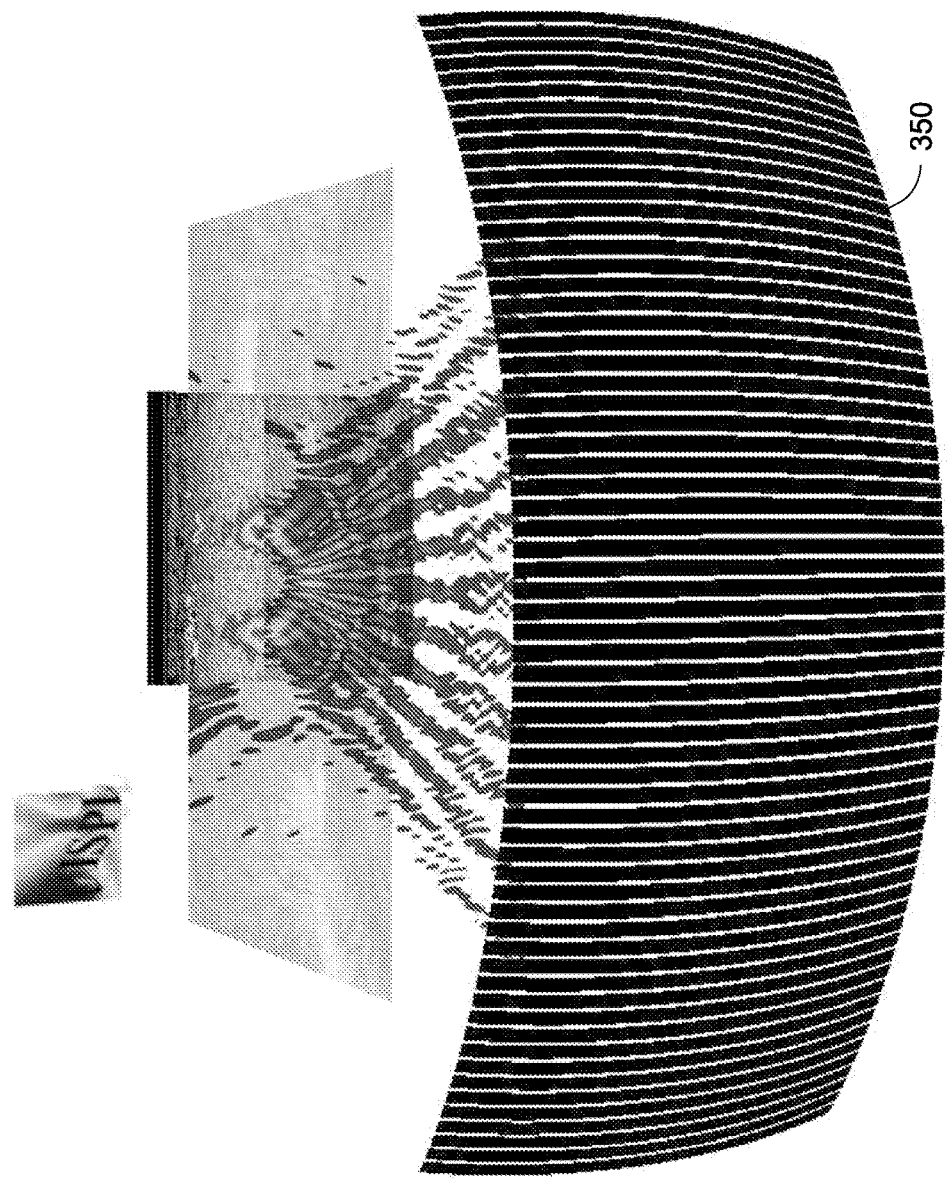
Figure 10C:
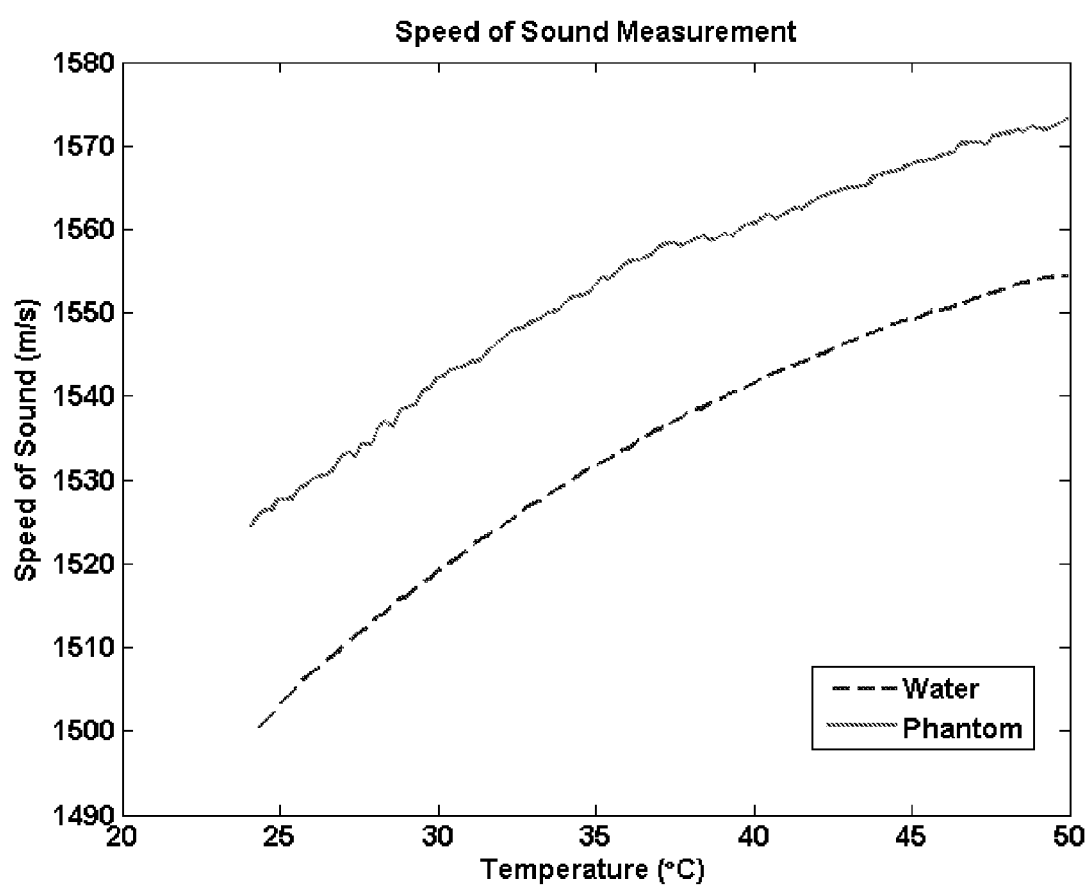
Figure 10D:
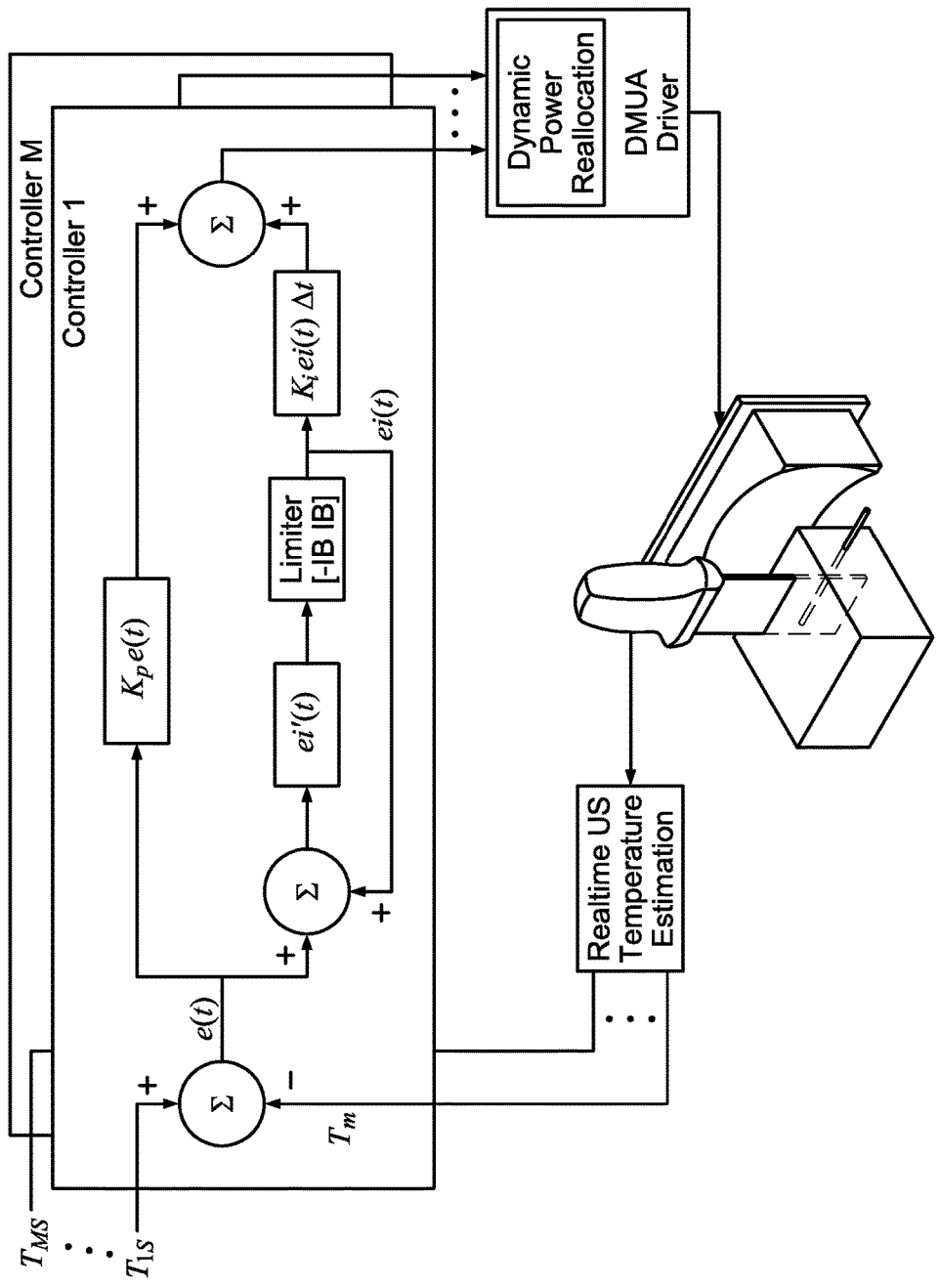
Figure 10E:
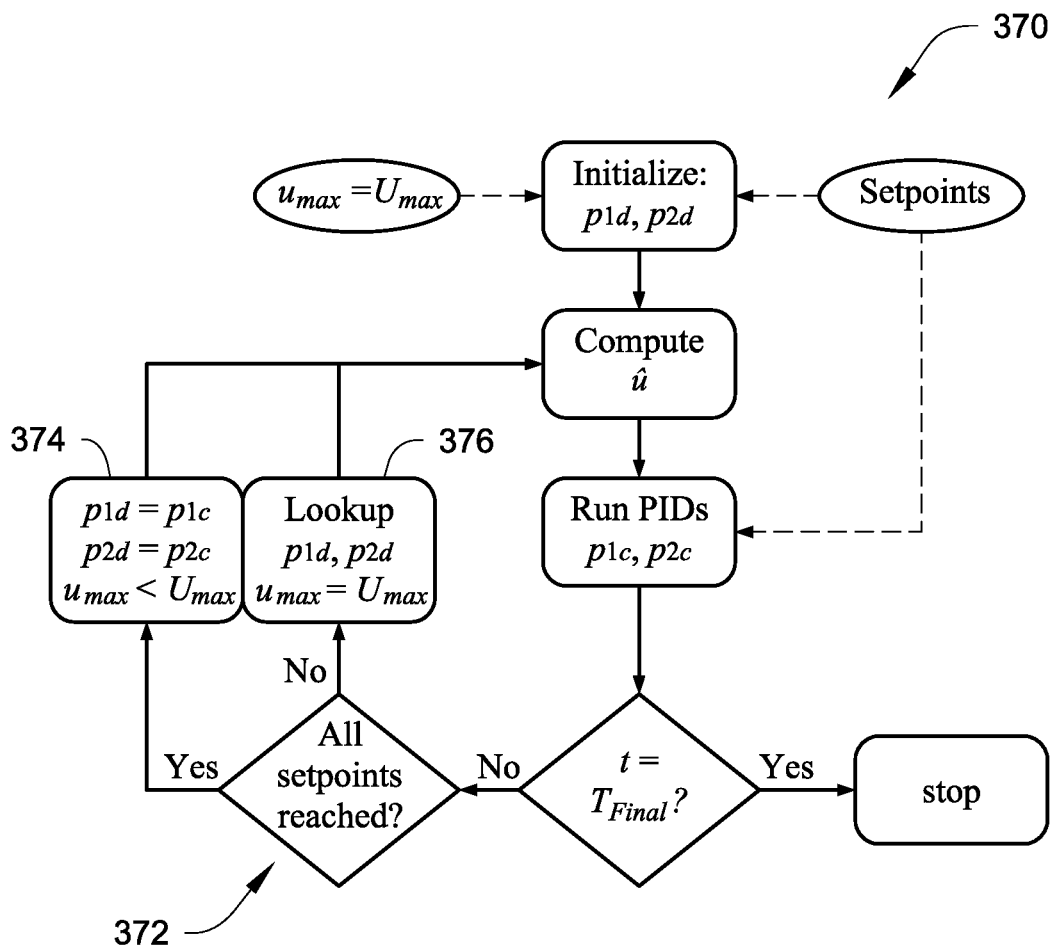

The logic driving the dynamic power reallocation while the PID controllers are active relies on testing the truth of the statement "All set point temperatures have been reached" (block 372 of FIG. 10E). This determines the output of the PID controllers according to the flowchart and method 370 shown in FIG. 10E. If yes, only a fraction of the available power is needed to maintain control ($u_{max}<U_{max}$); each focus will receive its requested power as specified by the PIDs (block 374). If no, the algorithm attempts to use 100% of the available power ($u_{max}=U_{max}$) by shifting excess power from points which are not using their full share, to points which are requesting more than their share (block 376). This can be performed adaptively (e.g., based on online measurement of temperature response) or in a prespecified manner (e.g. equal fractions of the available power).

Figure 10F:
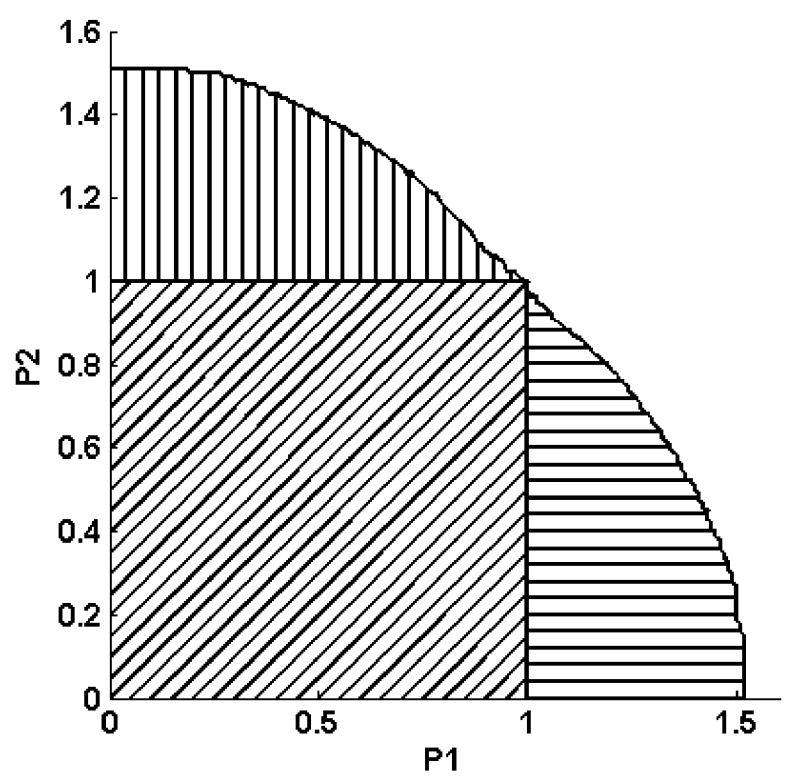

In order to share power between multiple focal points a function must exist that relates the maximum complex pressure for any set of focal points, given the pressures at the remaining focal points, such that $u_{max}=U_{max}$. FIG. 10F shows such a function for a double-focus pattern where power has initially been split evenly between the foci. The hatched region under the curve represents all realizable combinations of pressures. The diagonally hatched region represents the pressures achievable without power reallocation, i.e. each PID receives its requested power. The horizontally and vertically hatched regions represent the additional pressures made available by power reallocation. As an example, assume the two focal points were being heated to the same temperature, but focal point 1 was to heat faster than focal point 2. Once focal point 1 reached its set point temperature and its controller asked for less power, the function in FIG. 10F would be used to determine how much the pressure at focal point 2 could increase. In this way, an array that utilizes power reallocation is able to adaptively compensate for tissue inhomogeneities and tissue changes during therapy without any user input. In addition, the algorithm guarantees the use of maximum array efficiency as long as any of the control points is below its set point temperature. This minimizes the time to reach all set point temperatures and, consequently, minimize the treatment time when multiple-focus patterns are used.

For the purposes of this example, a table-lookup approach was developed for determining the magnitude of the complex pressure at the mth control point as a function of the desired values at the remaining control points. Briefly, assuming equal power sharing for points below their set point temperatures, the desired value at the mth control point, $p_{md}$, can be raised to a higher value based on the available power fraction. As an example, assume a two-focus pattern initialized with 50% of the available supply power delivered to each focus ($p_{1d} = p_{2d} = p_{max}$, where $p_{max}$ is the pressure magnitude achievable using 50% of the available power). Once one of the two control points (say Point 1) has reached its temperature set point, PID1 requests $p_{1d} < p_{max}$ leaving a larger fraction for PID2 to request $p_{2d} > p_{max}$. This accelerates the heating rate at Point 2 to minimize the time to reach its temperature set point. This control approach with dynamic power reallocation is summarized in FIG. 10E-10F. The hatched regions in FIG. 10F show when the lookup table is used (horizontal and vertical lines) and when direct calculation is used (diagonal lines). As illustrated by the figure, the lookup table is used whenever the desired pressure on any of the control points exceeds the maximum pressure preallocated to that point.

Results of the Example.

The performance of the multiple-focus control algorithm with two sets of experiments referred to as long exposure and short exposure with heating durations of 15 seconds and 5 seconds, respectively, is demonstrated. The latter is an example of typical exposure duration in high-temperature surgery using BIM. The former is long enough to demonstrate the workings of the algorithm in lower temperature applications such as drug delivery and hyperthermia. While heating durations in these applications may be much longer than 15 seconds, this duration s long enough to demonstrate the well-behaved nature algorithm in reaching the specified set point temperatures with typical settings of the PID parameters.

A. Long Exposure Temperature Control.

A two-focus pattern similar to that shown in FIG. 10B was used (FIG. 10B shows an imaging slice with temperature overlay together with the intensity profile of a double-focus pattern generated using the therapeutic array. The timing of the control experiment was as follows: Five seconds of baseline data was collected before the application of the heating pattern. The two-focus pattern was applied at 5 seconds with equal power applied to both foci. The set point temperatures were 3° C. for the primary focus (on the left) and 2, 3, 4, 5, and 6° C. at the secondary focus. The supply voltage, $V_{DC}$, was arbitrarily set to achieve approximately 1° C./s heating rate at the primary focus. The PID constants were selected to achieve a short settling time and minimum overshoot for the selected initial heating rate and given the values $k_p=2$; $k_i=4$; and $k_d=0$.

While the power was on (15-second duration): (1) Both PIDs were active according to the flowchart shown in FIG. 4; (2) For all set point combinations, equal power was allocated to each of the two foci at the start. While the temperatures at the primary and secondary focus remained below the set point temperatures, each PID requested the maximum available, which was 50% of the available DC power for the two-focus heating pattern used; (3) Once a set point temperature has been reached, the corresponding PID requested less power to maintain the temperature, which left some fraction of the DC power to be reallocated to the other focus; (4) The dynamic power reallocation algorithm recalculated the fraction of power delivered to each focus. This resulted in an increase in the heating rate at the focal point with temperature below the set point temperature; and (5) Once all set point temperatures have been reached, all the PIDs requested only the necessary power to maintain the temperature. This typically resulted in reducing the total power required from the DC supply. Temperature imaging continued for another 12 seconds after the array was turned off to monitor the temperature decay in the target plane.

Note that the thermocouple was carefully placed so that it was barely visible in the imaging plane (at the edge of the imaging slice). At the same time, it was also placed within the focal spot of the secondary focus, but below the focal point. This ensured that the thermocouple junction was directly heated by the secondary focus, but with minimum distortion to the therapy and imaging beams. The direct heating of the thermocouple produced a self-heating artifact that served as an indicator of the change in acoustic intensity at the thermocouple junction, which allowed us to observe the dynamic power reallocation.

Figure 10G:
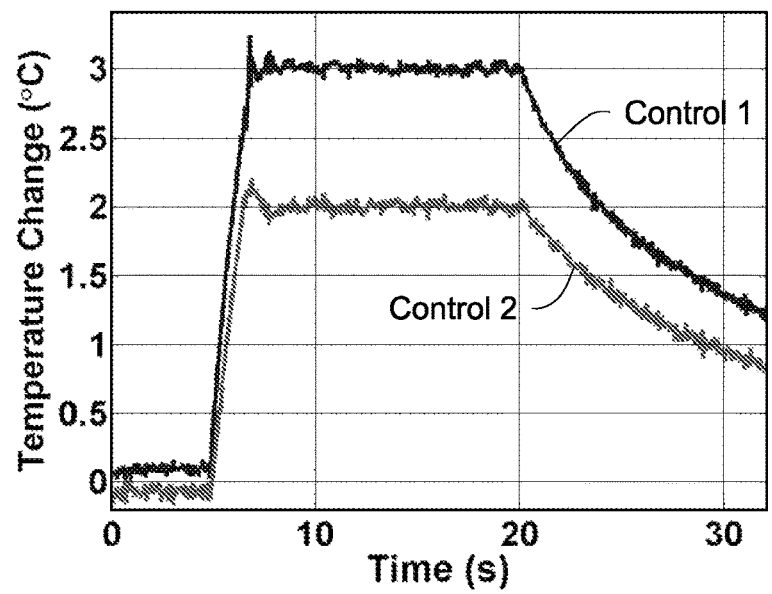
Figure 10G:
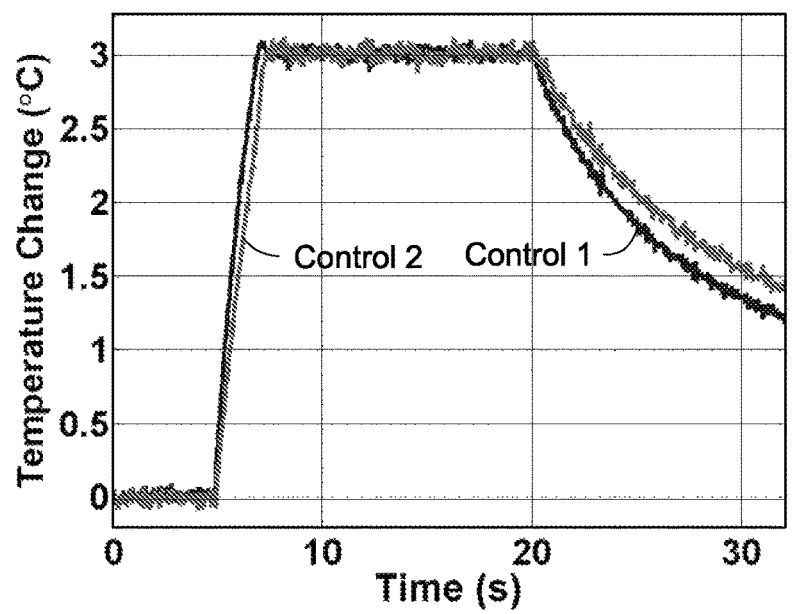
Figure 10G:
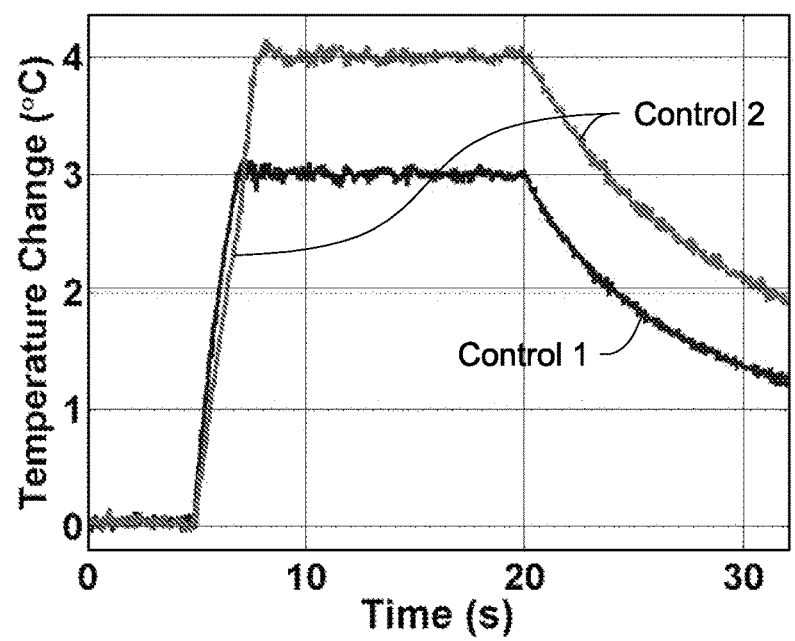
Figure 10G:
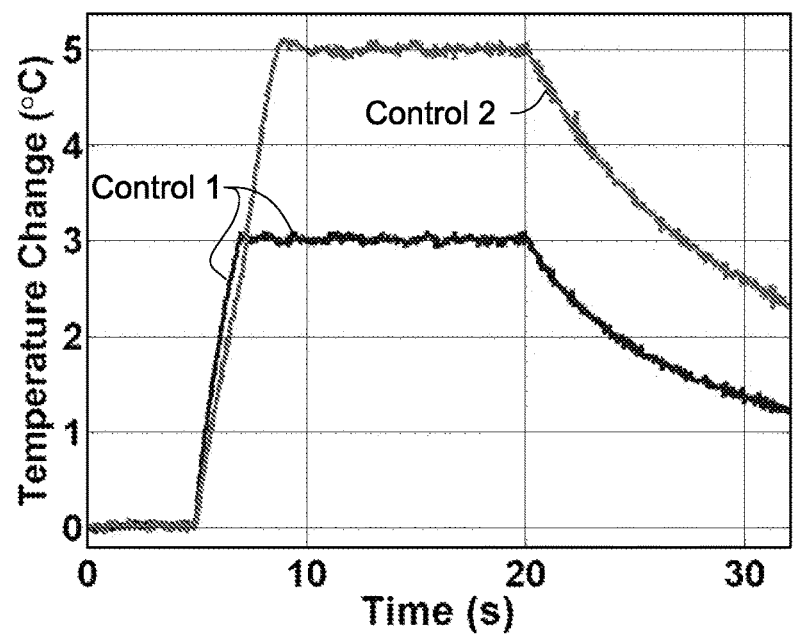
Figure 10G:
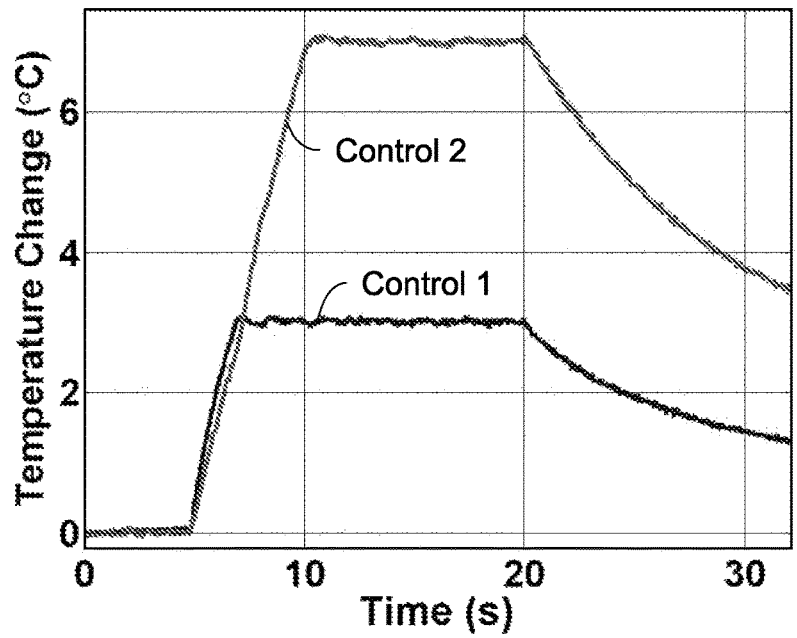
Figure 10G:
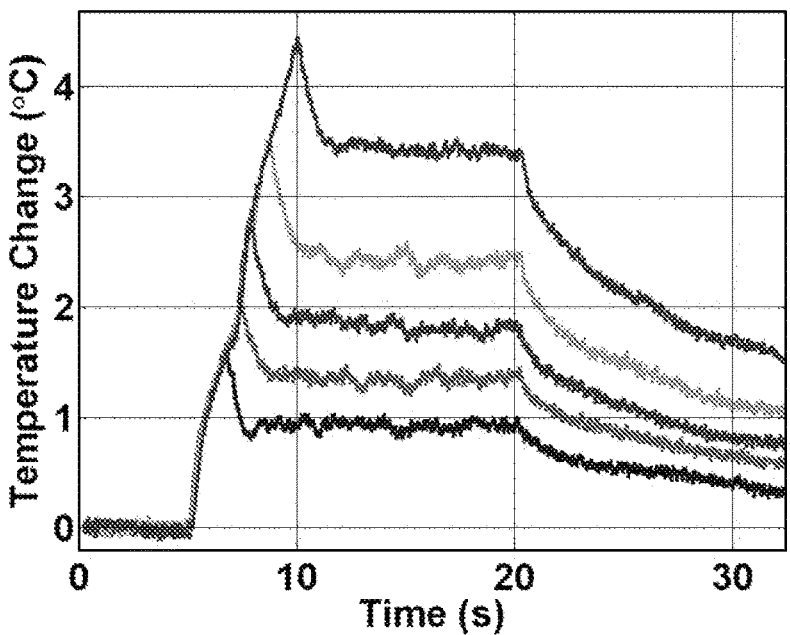

The results of this set of long-exposure experiments are shown in FIG. 10G. The estimated temperature profiles at the primary and secondary control points are shown in FIGS. 10G(a)-(e) for $T_{sec}$=2; 3; 4; 5; 7° C., respectively. FIG. 10G(f) shows the corresponding thermocouple measurements recorded near the secondary control point. For the cases where $T_{sec}$ was set equal to 4, 5, and 7° C., it is easy to see the change in the heating rate at the secondary control point upon reaching the set point at the primary control point in FIGS. 10G(c)-(e) and the corresponding thermocouple measurement. Additionally, the thermocouple measurements exhibit self-heating artifacts that appear as overshoot before decaying to the control temperature at the thermocouple junction location. These dynamics reflect the sudden increase of power delivered to the secondary focus upon reaching the set point temperature at the primary control point. It is also interesting to note that, for $T_{sec}$=2° C., a small but measurable change in the heating rate can be observed at the primary control point upon reaching the set point temperature at the secondary control point.

Figure 10H:
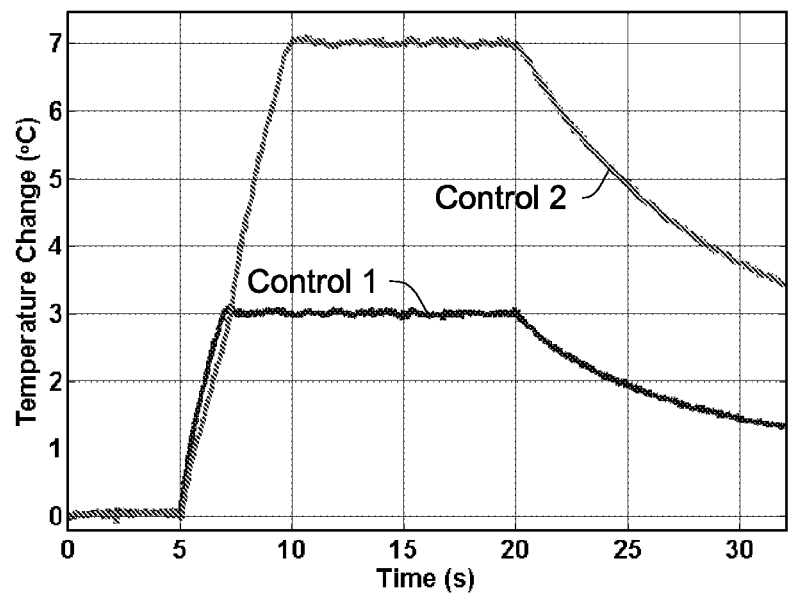
Figure 10H:
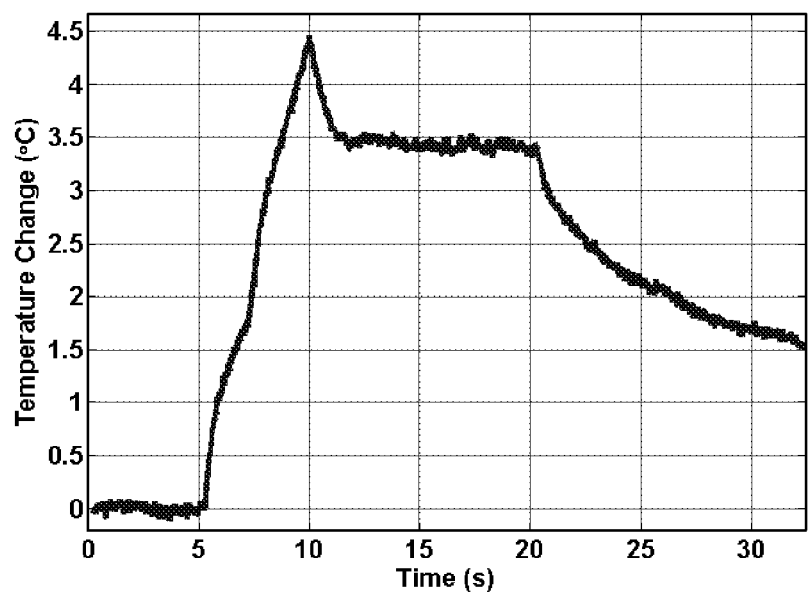
Figure 10I:
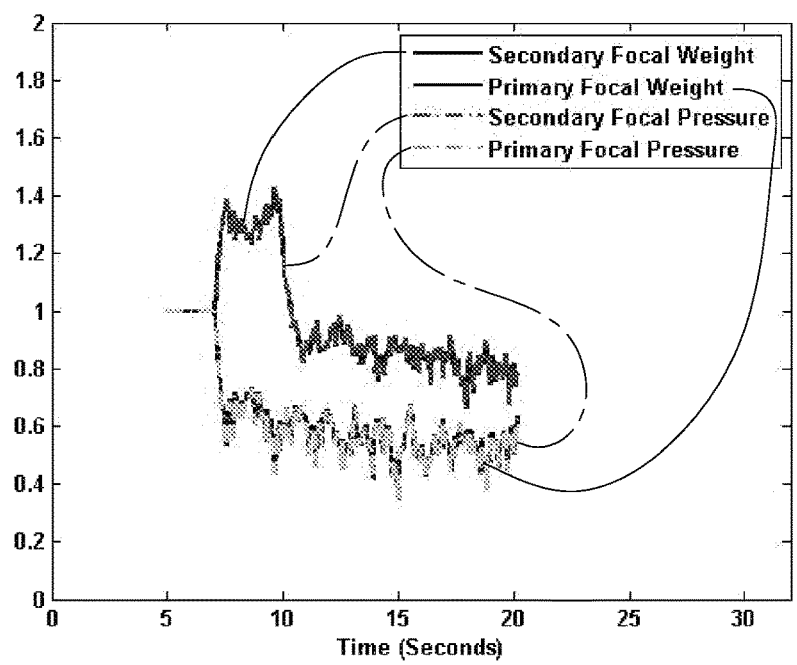
Figure 10I:
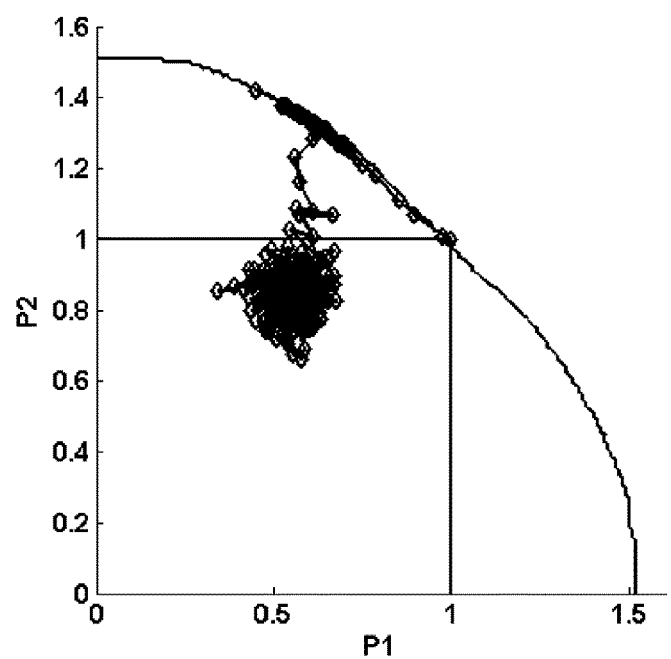

To further illustrate the dynamic power reallocation for the multiple-focus pattern, we show the profiles of the various parameters of the two-focus pattern used similar to the control experiments shown in FIG. 10G for the case $T_{sec}$=7° C. FIGS. 10H(a)-(b) shows the estimated temperatures at the primary and secondary control points and the corresponding thermocouple measurement near the secondary control point. The changes in the heating rate at the secondary point are clearly visible in both the estimated and directly measured temperature profiles. These occur at 5 sec (POWER ON time), ≈7 sec (primary set point temperature reached), and ≈10 sec (secondary set point temperature reached). These changes in the heating rate reflect the changes in power deposition at the secondary control point in response to the request of PID2 controller subject to the constraints on the power supply and the dynamic power reallocation described with reference to FIG. 10E. FIG. 10I(a) shows the relative pressure magnitudes at the primary and secondary points during the experiment. The profiles show both the synthesized (solid) and actually achieved pressure values (dashed, taking the discretization in the driver into account). It is clear that the amplitude control with <0:01 $U_{max}$ precision allows for excellent realization of the theoretically specified (desired) pressure values at the control points. FIG. 10I(b) shows a mapping of the control weights on the decision regions described in FIG. 10F starting at POWER ON time with ($p_{1d}$; $p_{2d}$)=(1; 1). For 5<t<7 sec (both control points below set point temperatures), $p_{1d}=p_{2d}=1$ and no power reallocation occurs. When one or more of the set point temperature is reached, $p_{1d}$ and $p_{2d}$ will be increasing (indicated by ↑), decreasing (indicated by ↓), or fluctuating (indicated by ↑↓). For 7<t<7.5 s (just after reaching set point temperature at primary control point), $p_{1d}<1$ ↓ and $p_{2d}>1$ ↑ with $p_{2d}$ maximum allowable for a given value of $p_{1d}$ as determined by the lookup table. For 7.5<t<10 sec (PID1 actively controlling primary set point temperature), $p_{1d}<1$ ↑↓ and $p_{2d}>1$ ↑↓ excess power reallocated to the secondary point, but limited by the fluctuation in $p_{1d}$ values to maintain control of the primary control point. For 10<t<11 (just after reaching secondary set point temperature), $p_{1d}<1$ ↑↓ and $p_{2d}>1$ ↑↓ PID2 requesting less than the maximum allowable as it moves toward maintaining the temperature at the secondary control point. Finally, for t>11 sec, $p_{1d}<1$ ↑↓ and $p_{2d}<1$ ↑↓ both PID1 and PID2 are actively controlling the primary and secondary control points around their respective set point temperatures. This is a result that clearly illustrates the fast, but well-behaved, response of the PID controllers to reaching the various set point temperatures.

Figure 10J:
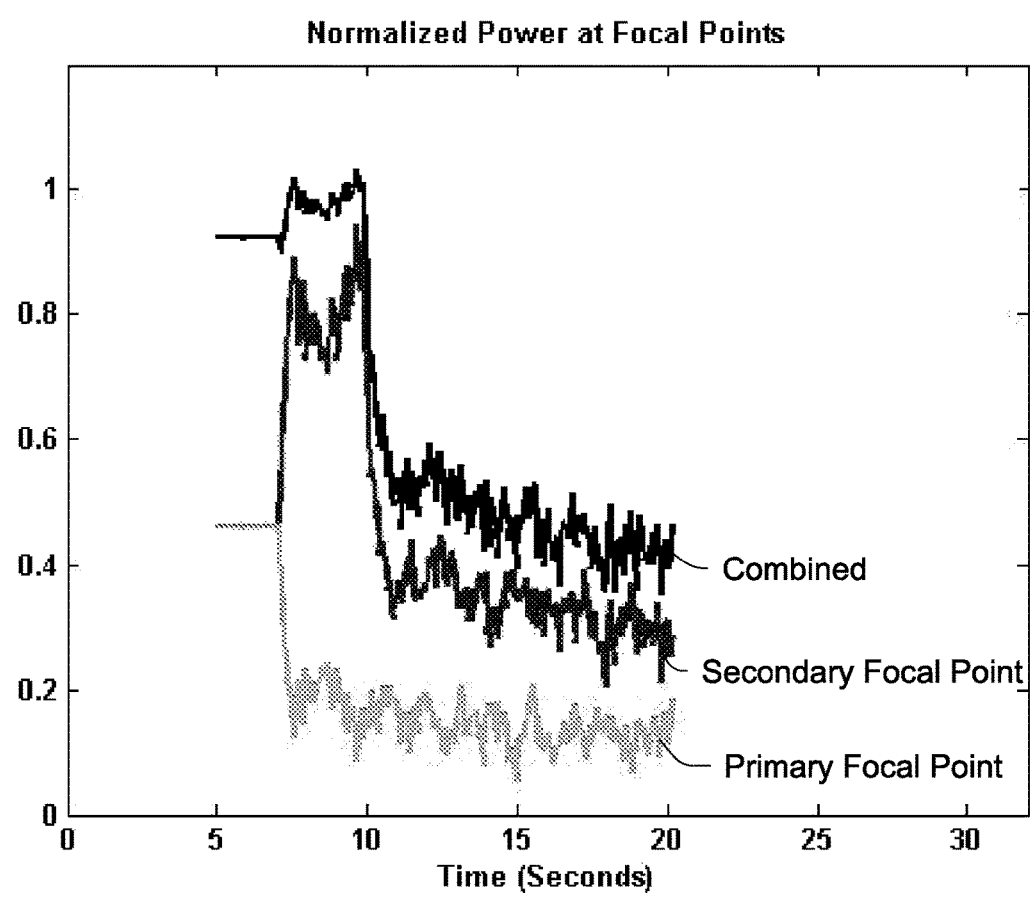

To confirm the dynamics of power reallocation, the power delivered in the vicinity of each control point for each set of weights shown in FIG. 10I was computed. The result is shown in FIG. 10J. One can see three distinct intervals in terms of power sharing and total power delivered to the focal plane. These can be described as follows:

(1) 0<t<2 s after POWER ON: Equal power was delivered to each focus before the set point temperature at the primary control point was reached. In this case, both PIDs were asking for the maximum available power since the error was negative. The power sharing was set at 50%, but other ratios could have been set to satisfy specific treatment considerations. The relative weights of the pressure at both control points was set to 1 as can be seen in FIG. 10I.

(2) 2.5<t<5 s after POWER ON: Set point temperature at the primary control point is reached and PID1 requested less power. The relative weight at the primary control point dropped while that at the secondary increased. Correspondingly, the power allocated to the focus at the primary control point was approximately 20% of the total power in the focal plane while the power delivered to the secondary was 80%.

(3) 6<t<15 s after POWER ON: Set point temperatures were reached at both control points and both PIDs requested less power to maintain the temperature. The supply power was reduced and the power share at each focus was determined by the relative weight requirement (both <1, but not necessarily equal).

Other results (not shown) included a normalized DC supply power and the array efficiency predicted by Equation 3 for the $T_{sec}=7°$ C. experiment. The DC supply power was determined by the set voltage on the Agilent 6030A and the actual current measured during operation using the GPM interface. The result provided the normalized DC supply power and the normalized power deposition in the focal plane for the same experiment. This result served to demonstrate that the synthesis process results in well-behaved multiple-focus patterns where the power delivered to the focal points is proportional to the input (DC supply) power. This would not have been the case, for example, if the multiple-focus patterns required high spatial frequencies at the array surface resulting in evanescent waves. This serves to demonstrate the robustness of the synthesis process in response to dynamic changes dictated by the PID requirements at the different control points.

B. Short Exposure Temperature Control.

A similar set of experiments were carried out to demonstrate the performance of the algorithm in the control of multiple focus patterns with shorter exposure durations. As was done above, the set point temperature at the primary control point, $T_{pri}$ was fixed at 3° C. in all experiments. On the other hand, the temperature set point at the secondary control point, $T_{sec}$ was set at 2, 3, 4, 5, and 6° C. for the different experiments. The DC supply voltage was fixed at higher value (approximately 2× to achieve a faster heating rate of ≈4° per second. The PID constants, $k_p$; $k_i$; $k_d$, were the same as in the long exposure experiments to provide an idea about the dynamic behavior of the controllers when faster heating rates are sought.

The estimated and measured temperature profiles for the short exposure experiments (not shown) indicated that the heating rate at the control points is such that the temperature response exhibits an overshoot and oscillations in both the noninvasive estimates and the thermocouple measurements. As before, the overshoot in the thermocouple measurement was more pronounced (compared to the noninvasive estimate) due to the direct heating at the thermocouple junction. It was clear from the results, however, that the thermocouple measurements reflect the dynamics of the control and dynamic power reallocation algorithm. The results also indicated that both PIDs achieve control within a fraction of the POWER ON time for this short exposure protocol.

Discussion Regarding the Example.

The results in this example provide a real-time demonstration of temperature control using multiple-focus phased array patterns based on noninvasive temperature feedback and with sub-second resolution. This example provides a configuration of an ultrasound-guided focused ultrasound system employing phased array technology for generating single or multiple-focus patterns that may be tailored to achieve the treatment objectives, e.g. hyperthermia, drug activation, high temperature ablative therapies, etc. This system is operational in real-time for use in real-time thermal therapy applications.

While control is a focus of this example, the control objectives may be implemented in any suitable control system. Although standard PID controllers were used for the individual control points as an example of a commonly used conventional controller, other control algorithms could be used (see, Siep et al. (1996) or those discussed in the context of the transient bioheat equation (tBHTE) as a distributed model of the treatment volume and possibly thermal dose calculations in Sapareto and Dewey, "Thermal dose determination in cancer therapy," Int. J. Rad Onc. Biol. Phys., vol. 10, no. 6, pp. 787-800, 1984; and Wan, et al. "Ultrasound surgery: Comparison of strategies using phased array systems," IEEE Trans. UFFC, vol. 43, no. 6, pp. 1085-1098, November 1996)).

In at least this example, a an important aspect of the controller implementation, however, is the dynamic power reallocation algorithm, which was used to dynamically (adaptively) determine the power directed to the individual focal points (based on PID commands). This may be important to the successful use of multiple-focus pattern synthesis in achieving specific heating rates at the control points given the characteristics/limitations of the available power supply. The results shown demonstrate how the dynamic power reallocation algorithm achieves: (1) Maximize the array efficiency by compressing the dynamic range of the driving signal distribution resulting from the theoretical multiple-focus synthesis; and (2) Distribute the available power among the individual foci to satisfy the PID requirements.

For the feedback control system described in this example, it was achieved in real-time at 25 Hz update rate. It should be noted that the update rate could have been done at the full frame rate of the temperature feedback of 99 Hz. In fact, the GPU/FPGA beam synthesis/driver for the array allows update rates in the 400-600 Hz range. Therefore, with the advent of high frame rate ultrasound systems, this allows for exquisite control over the spatial and temporal dynamics of the heating/lesion formation process in ways that are improved over other guidance modalities, e.g. MRI. Regardless of the method used for obtaining noninvasive temperature measurements at the control points, however, the dynamic power reallocation and optimal synthesis methods described in this example may be used for generating multiple-focus patterns in therapeutic applications.

The ultrasound thermography algorithm described in this example, may be used with M2D imaging (see, Liu and Ebbini, "Real-Time 2-D Temperature Imaging Using Ultrasound," IEEE TRANSACTIONS ON BIOMEDICAL ENGINEERING, vol. 57, no. 1, pp. 12-16, January 2010). For example, in Liu and Ebbini (2010), M2D imaging mode is introduced as a tool in capturing the full range of thermal and mechanical strains in 2D spatial coordinates with high temporal resolution (100 s of fps with limited FOV). This may be used to remove tissue motion/deformation artifacts through new formulations dealing with the temperature imaging as an image reconstruction problem (e.g., strain components due to temperature change can be reliably separated from strain components resulting from natural deformations, e.g. due to breathing).

This example demonstrates the real-time control of multiple-focus phased array heating patterns for thermal therapy based on noninvasive ultrasound thermography (e.g., thermal control image data). The results are relevant to the control of short-exposure multiple-focus patterns suitable for ablative therapy as well as longer exposure patterns suitable for hyperthermia, drug delivery and other they therapy applications. Further, the use of dynamic power reallocation method designed to maintain maximum array driving efficiency with multiple-focus patterns has also been demonstrated. Dynamic power reallocation may be a factor in successful use of multiple focus patterns in reducing treatment time. Even for the simple, double-focus, patterns shown in this example, the driver would have failed to provide adequate heating at the primary and secondary foci if the weighting and dynamic power reallocation algorithms were not employed. The results also demonstrate the fact that dynamic power reallocation is observed through changes in the heating rate at the control points, which can be reliably computed from noninvasive temperature estimation. Thermocouple measurements in the vicinity of the HIFU focus confirm the dynamics of temperature variation in response to the control algorithm, including the effects of power reallocation method. Further, the results presented in this example, demonstrate the feasibility of using multiple focus heating patterns to achieve treatment objectives without compromising the driving efficiency of the phased array.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

The invention claimed is:

1. A dual mode ultrasound transducer system for integrated image-guided therapy comprising:
 a refocusable array of ultrasound transducer elements configured to provide synthesized ultrasound wavefronts, the ultrasound transducer elements configured to deliver one or more therapy shots to at least a portion of a target region and to transmit/receive imaging ultrasound wavefronts to/from the target region, wherein each of the one or more therapy shots comprises a plurality of sequential therapy bursts of ultrasound wavefronts; and
 control apparatus comprising at least one processor configured to:
  control conveyance of imaging signals to/from one or more of the plurality of ultrasound transducer elements;
  generate treatment region image data usable to identify at least one or more target points within a target region based on imaging signals conveyed to/from one or more of the plurality of ultrasound transducer elements;
  generate one or more signals to drive one or more of the plurality of ultrasound transducer elements to provide a synthesized ultrasound wavefront using image-based refocusing;
  generate therapy signals to drive one or more of the plurality of ultrasound transducer elements to deliver one or more therapy shots to at least a portion of a target region, wherein each therapy shot is configured to achieve a therapeutic endpoint comprising at least one of a desired thermal and mechanical change in the target region, wherein delivery of each of the one or more therapy shots comprises delivery of a plurality of sequential therapy bursts of ultrasound wavefronts to at least one of the one or more target points in the target region configured to achieve the therapeutic endpoint within the therapy shot using accumulated exposure over the plurality of sequential therapy bursts, wherein each of the plurality of sequential therapy bursts is a continuous therapy burst having an amplitude, a duration, and a spectral content separated in time from a subsequent therapy burst, wherein each of the continuous therapy bursts has a duration less than 10 milliseconds, and further wherein the time between the continuous therapy bursts is less than 10 milliseconds; and
  generate control image data based on at least one of imaging signals from one or more of the plurality of ultrasound transducer elements during delivery of each therapy burst of a plurality of sequential therapy bursts and imaging signals from one or more of the plurality of ultrasound transducer elements following delivery of each therapy burst of a plurality of sequential therapy bursts to monitor tissue response in the target region to the delivery of the sequential therapy bursts in real-time, wherein the control image data is used as feedback to generate therapy signals to drive one or more of the plurality of ultrasound transducer elements to deliver at least one subsequent continuous therapy burst within the therapy shot, wherein the control image data is used as feedback to adjust at least one of the amplitude, the duration, and the spectral content of at least one subsequent continuous therapy burst to be delivered to achieve the therapeutic endpoint within the therapy shot being delivered to the target region.

2. The system of claim 1, wherein the control apparatus is configured to generate at least one imaging signal using transmit focus at one or more points in the target region to drive one or more of the plurality of ultrasound transducers to transmit at least one ultrasound wavefront to produce single transmit focus (STF) imaging data for control image data.

3. The system of claim 1, wherein the control apparatus is further configured to generate treatment region image data usable to identify one or more critical points representative of intervening tissue in the path between the plurality of ultrasound transducer elements and the one or more target points within the target region based on imaging signals conveyed to/from one or more of the plurality of ultrasound transducer elements.

4. The system of claim 3, wherein, to generate control image data the control apparatus is configured to generate at least one imaging signal to drive one or more of the plurality of ultrasound transducers elements to transmit at least one single transmit energy pulse focused to one or more of the critical points resulting in pulse-echo data to be captured.

5. The system of claim 2, wherein the control apparatus is configured to generate imaging signals using transmit focus at one or more points in the target region to drive one or more of the plurality of ultrasound transducers to transmit sequential single transmit focus (STF) ultrasound wavefronts focused to at least one of one or more target points within the target region and one or more critical points resulting in pulse-echo data to be captured.

6. The system of claim 1, wherein the control apparatus is further configured to use coded excitation to generate at least two signals to drive one or more of the plurality of ultrasound transducers to produce at least two overlapping continuous bursts of ultrasound wavefronts, wherein each overlapping continuous burst is configured to provide a different waveform to one or more target points.

7. The system of claim 1, prior to delivery of a subsequent therapy burst of the plurality of sequential therapy bursts at therapeutic levels based on therapy signals generated using the control image data generated the control apparatus is configured to control a test of the subsequent therapy burst at sub-therapeutic levels.

8. The system of claim 1, wherein the control apparatus is further configured to generate one or more signals to drive one or more of the plurality of ultrasound transducer elements to provide at least one of the sequential therapy bursts based on imaging at least one of a reversible thermal change and a reversible mechanical change at one or more points in the target region caused by a sub-therapeutic burst of ultrasound.

9. The system of claim 1, wherein the control apparatus is configured to generate at least one imaging signal to drive one or more of the plurality of ultrasound transducers to transmit at least one ultrasound energy pulse to the target region resulting in pulse-echo data to be captured by one or more of the plurality of ultrasound transducer elements between the generation of therapy signals that result in each sequential therapy burst of ultrasonic energy to be delivered to the target region via the plurality of ultrasound transducer elements.

10. The system of claim 1, wherein to generate control image data the control apparatus is configured to generate control image data comprising ultrasound transducer element directivity data, wherein at least the ultrasound transducer element directivity data is used to generate therapy signals to drive one or more of the plurality of ultrasound transducer elements to deliver a subsequent therapy burst of the plurality of sequential therapy bursts.

11. The system of claim 1, wherein to generate control image data the control apparatus is configured to generate control image data comprising thermal response data, wherein at least the thermal response data is used to generate therapy signals to drive one or more of the plurality of ultrasound transducer elements to deliver a subsequent therapy burst of the plurality of sequential therapy bursts.

12. The system of claim 1, wherein to generate control image data the control apparatus is configured to generate control image data comprising at least one of displacement and strain data associated with at least the target region, wherein the at least one of the displacement and strain data is used to generate therapy signals to drive one or more of the plurality of ultrasound transducer elements to deliver a subsequent therapy burst of the plurality of sequential therapy bursts.

13. The system of claim 1, wherein to generate control image data the control apparatus is configured to generate control image data comprising data indicative of cavitation, wherein at least the data indicative of cavitation is used to generate therapy signals to drive one or more of the plurality of ultrasound transducer elements to deliver a subsequent therapy burst of the plurality of sequential therapy bursts.

14. The system of claim 1, wherein the system comprises a control channel associated with each of a plurality of ultrasound transducer elements of the array, wherein each control channel associated with each of the plurality of ultrasound transducer elements comprises a configurable diplexer between analog to digital converter apparatus and a corresponding ultrasound element to isolate the analog to digital converter apparatus from high voltage therapy signals applied to the ultrasound transducer element but still allow low level imaging signals from pulse echo data to pass through, and further wherein each of the configurable diplexers comprises an amplifier controllable to have its output set to an impedance state when a therapy signal is not being transmitted that is higher than an impedance state of the output when a therapy signal is being transmitted, and further wherein the control apparatus is configured to:

generate multiple channel therapy signals for driving the plurality of ultrasound transducer elements via the respective control channels to deliver energy to at least one target point in the target region, wherein each of the plurality of ultrasound transducer elements is driven at one or more drive parameters to focus the ultrasound energy for delivery of each sequential therapy burst;

generate control image data based on at least one of imaging signals received via the respective control channels from one or more of the plurality of ultrasound transducer elements during delivery of each therapy burst of a plurality of sequential therapy bursts and imaging signals received via the respective control channels from one or more of the plurality of ultrasound transducer elements following delivery of each therapy burst of a plurality of sequential therapy bursts to monitor tissue response in the target region;

adjust one or more of the drive parameters of one or more of the plurality of ultrasound transducer elements based on the control image data; and set the output of the amplifier associated with each of the plurality of ultrasound transducer elements, when a therapy signal is not being transmitted, to an impedance state that is higher than an impedance state of the output when a therapy signal is being transmitted.

15. The system of claim 1, wherein the system further comprises a display apparatus to display image data and a user interface to allow a user to input one or more commands for real-time control of the delivery of the plurality of sequential therapy bursts, and further wherein the user interface is configured to allow a user to select at least one of one or more target points and one or more critical points for use in controlling delivery of the plurality of sequential therapy bursts.

16. The system of claim 14, wherein the configurable diplexer further comprises a selectable voltage divider to attenuate a pulse echo signal received by the transducer element, and further wherein the control apparatus is configured to control the selectable voltage divider to at least one of attenuate the pulse echo signal or leave the pulse echo signal at its current level.

17. The system of claim 1, wherein the control apparatus comprises at least one processor coupled to a multimodal imaging apparatus, wherein the multimodal imaging apparatus comprises at least one processor configured to fuse image data resulting from a plurality of different imaging modes, wherein the control apparatus is configured to provide the fused image data for at least one of display and use to generate control image data.

18. The system of claim 1, wherein the system further comprises at least one other ultrasound diagnostic apparatus comprising an imaging probe configured to capture ultrasound pulse-echo data of at least a portion of the target region in response to the delivery of one or more of the plurality of sequential therapy bursts.

19. The system of claim 1, wherein the control apparatus is configured to generate therapy signals usable for thermal treatments.

20. The system of claim 1, wherein the control apparatus is configured to generate therapy signals usable for non-thermal treatments.

21. The system of claim 1, wherein the control apparatus is configured to generate therapy signals to drive one or more of the plurality of ultrasound transducer elements to deliver a plurality of sequential therapy bursts of ultrasonic energy to at least one of the one or more target points in the target region using coded excitation.

22. The system of claim 1, wherein the system further comprises a control channel associated with each of a plurality of ultrasound transducer elements of the array,
wherein the control apparatus comprises a multichannel driver configured to drive the plurality of ultrasound transducer elements with therapy signals and imaging signals, wherein the multichannel driver is configurable to store and control the therapy signals and imaging signals used to drive the plurality of ultrasound transducer elements,
wherein the multichannel driver comprises a plurality of buffers, wherein the plurality of buffers comprises:
at least a first buffer to provide storage of a therapy protocol of therapy signals to be delivered by the plurality of ultrasound transducer elements during a current time period for use in driving the plurality of ultrasound transducer elements via the respective control channels to deliver energy to at least one target point in the target region, wherein each of the plurality of ultrasound transducer elements is driven at one or more drive parameters to focus the ultrasound energy for delivery of each sequential therapy burst, the one or more drive parameters corresponding to at least one of the amplitude, the duration, and the spectral content defining each continuous therapy burst of the plurality of sequential therapy bursts; and
a second buffer to store a therapy protocol of therapy signals to be delivered in a next time period following the current time period; and
further wherein the control apparatus comprising the at least one processor is configured to:
generate control image data based on at least one of imaging signals received via the respective control channels from one or more of the plurality of ultrasound transducer elements during delivery of each therapy burst of a plurality of sequential therapy bursts and imaging signals received via the respective control channels from one or more of the plurality of ultrasound transducer elements following delivery of each therapy burst of a plurality of sequential therapy bursts to monitor tissue response in the target region; and
adjust one or more of the drive parameters of one or more of the plurality of ultrasound transducer elements based on the control image data for storage by the second buffer of the therapy protocol comprising the adjusted drive parameters to be delivered in the next time period following the current time period for use in driving the plurality of ultrasound transducer elements via the respective control channels to deliver energy to at least one target point in the target region, wherein each of the plurality of ultrasound transducer elements is driven at the adjusted drive parameters to focus the ultrasound energy for delivery of the subsequent therapy burst, the adjusted drive parameters corresponding to at least one of the amplitude, the duration, and the spectral content defining the continuous therapy burst corresponding to the subsequent therapy burst of the plurality of sequential therapy bursts.

23. The system of claim 22, wherein the control apparatus is configured to manage the first and second buffers to provide a reconfigurable silencing period with a granularity of less than 1 microsecond, the reconfigurable silencing period being below the mechanical and thermal response time of the tissue.

24. The system of claim 1, wherein, to generate control image data to monitor tissue response in the target region to the delivery of the sequential therapy bursts in real-time, the control image data is generated based on at least one of imaging signals from one or more of the plurality of ultrasound transducer elements during delivery of each therapy burst of a plurality of sequential therapy bursts and imaging signals from one or more of the plurality of ultrasound transducer elements following delivery of each therapy burst of a plurality of sequential therapy bursts and before each next therapy burst.

25. A dual mode ultrasound transducer therapy method for integrated image-guided therapy comprising:
providing a refocusable array of ultrasound transducer elements configured to provide synthesized ultrasound wavefronts, the ultrasound transducer elements configured to deliver one or more therapy shots to at least a portion of a target region and to transmit/receive imaging ultrasound wavefronts to/from the target region, wherein each of the one or more therapy shots comprises a plurality of sequential therapy bursts of ultrasound wavefronts;
generating treatment region image data and identifying at least one or more target points within a target region thereof based on pulse echo data received by one or more of the plurality of ultrasound transducer elements;

generating one or more signals to drive one or more of the plurality of ultrasound transducer elements to provide a synthesized ultrasound wavefront using image-based refocusing;

generating therapy signals to drive one or more of the plurality of ultrasound transducer elements to deliver one or more therapy shots to at least a portion of a target region, wherein each therapy shot is configured to achieve a therapeutic endpoint comprising at least one of a desired thermal and mechanical change in the target region, wherein delivery of each of the one or more therapy shots comprises delivery of a plurality of sequential therapy bursts of ultrasound wavefronts to at least one of the one or more target points in the target region to produce a response at the one or more target points within the target region configured to achieve the therapeutic endpoint within the therapy shot using accumulated exposure over the plurality of sequential therapy bursts, wherein each of the plurality of sequential therapy bursts is a continuous therapy burst having an amplitude, a duration, and a spectral content separated in time from a subsequent therapy burst, wherein each of the continuous therapy bursts has a duration less than 10 milliseconds, and further wherein the time between the continuous therapy bursts is less than 10 milliseconds; and generating control image data based on at least one of pulse echo data received by one or more of the plurality of ultrasound transducer elements during delivery of each therapy burst of a plurality of sequential therapy bursts and pulse echo data received by one or more of the plurality of ultrasound transducer elements following delivery of each therapy burst of a plurality of sequential therapy bursts to monitor tissue response in the target region to the delivery of the sequential therapy bursts in real-time, wherein the control image data is used as feedback to generate therapy signals to drive one or more of the plurality of ultrasound transducer elements to deliver at least one subsequent continuous therapy burst within the therapy shot, wherein the control image data is used as feedback to adjust at least one of the amplitude, the duration, and the spectral content of at least one subsequent continuous therapy burst to be delivered to achieve the therapeutic endpoint within the therapy shot being delivered to the target region.

26. The method of claim 25, wherein generating at least one imaging signal using transmit focus at one or more points in the target region to drive one or more of the plurality of ultrasound transducers to transmit at least one ultrasound wavefront to produce single transmit focus (STF) imaging data for control image data.

27. The method of claim 25, wherein the method further comprises identifying one or more critical points within the treatment region representative of intervening tissue in the path between the plurality of ultrasound transducer elements and the one or more target points within the target region.

28. The method of claim 27, wherein generating control image data comprises generating at least one imaging signal to drive one or more of the plurality of ultrasound transducers to transmit at least one single transmit energy pulse focused to one or more of the critical points resulting in pulse-echo data to be captured.

29. The method of claim 26, wherein generating at least one imaging signal comprises generating imaging signals using transmit focus at one or more points in the target region to drive one or more of the plurality of ultrasound transducers to transmit sequential single transmit focus (STF) ultrasound wavefronts focused to each of a plurality of one or more target points within the target region or one or more critical points resulting in pulse-echo data to be captured.

30. The method of claim 25, further comprising using coded excitation to generate at least two signals to drive one or more of the plurality of ultrasound transducers to produce at least two overlapping continuous bursts of ultrasound wavefronts, wherein each overlapping continuous burst is configured to provide a different waveform to one or more target points.

31. The method of claim 25, prior to delivery of a subsequent therapy burst of the plurality of sequential therapy bursts based on therapy signals generated using control image data generated, the method comprises testing the subsequent therapy burst at sub-therapeutic levels lower than therapeutic levels associated with the subsequent therapy burst.

32. The method of claim 25, generating one or more signals to drive one or more of the plurality of ultrasound transducer elements to provide at least one of the sequential therapy bursts based on imaging at least one of a reversible thermal change and a reversible mechanical change at one or more points in the target region caused by a sub-therapeutic burst of ultrasound.

33. The method of claim 25, wherein control image data is generated between the generation of therapy signals that result in each sequential therapy burst of ultrasonic energy to be delivered to the target region via the plurality of ultrasound transducer elements.

34. The method of claim 25, wherein generating control image data comprises generating control image data comprising at least one of ultrasound transducer element directivity data, displacement data, strain data, thermal response data, and data indicative of cavitation, wherein the control image data is used to generate therapy signals to drive one or more of the plurality of ultrasound transducer elements to deliver a subsequent therapy burst of the plurality of sequential therapy bursts.

35. The method of claim 25, wherein a control channel is associated with each of a plurality of ultrasound transducer elements of the array, wherein each control channel associated with each of the plurality of ultrasound transducer elements comprises a configurable diplexer between analog to digital converter apparatus and a corresponding ultrasound element to isolate the analog to digital converter apparatus from high voltage therapy signals applied to the ultrasound transducer element but still allow low level imaging signals from pulse echo data to pass through, and further wherein each of the configurable diplexers comprises an amplifier controllable to have its output set to an impedance state when a therapy signal is not being transmitted that is higher than an impedance state of the output when a therapy signal is being transmitted, and further wherein the method comprises:

generating multiple channel therapy signals for driving the plurality of ultrasound transducer elements via the respective control channels to deliver energy to at least one target point in the target region, wherein each of the plurality of ultrasound transducer elements is driven at one or more drive parameters to focus the ultrasound energy for delivery of each sequential therapy burst;

generating control image data based on at least one of pulse echo data received via the respective control channels from one or more of the plurality of ultrasound transducer elements during delivery of each therapy burst of a plurality of sequential therapy bursts and pulse echo data received via the respective control channels from one or more of the plurality of ultrasound transducer elements following delivery of each therapy burst of a plurality of sequential therapy bursts to monitor tissue response in the target region;
adjusting the one or more drive parameters to drive each of the plurality of ultrasound transducer elements based on the control image data; and
setting the output of the amplifier associated with each of the plurality of ultrasound transducer elements, when a therapy signal is not being transmitted, to an impedance state that is higher than an impedance state of the output when a therapy signal is being transmitted.

36. The method of claim 25, wherein the method further comprises:
displaying image data;
providing a user interface to allow a user to input one or more commands for real-time control of the delivery of the plurality of sequential therapy bursts; and
selecting, by a user using the user interface, at least one of one or more target points and one or more critical points for use in controlling delivery of the plurality of sequential therapy bursts.

37. The method of claim 25, wherein the method further comprises:
fusing image data resulting from a plurality of different imaging modes; and
providing the fused image data for at least one of display and use to generate control image data.

38. The method of claim 25, wherein generating the control image data comprises generating the control image data in real-time relative to the therapy signals.

39. The method of claim 25, wherein the method further comprises using at least one other ultrasound diagnostic apparatus to capture ultrasound pulse-echo data of at least a portion of the target region in response to the delivery one or more of the plurality of sequential therapy bursts.

40. The method of claim 25, wherein generating therapy signals comprises generating therapy signals to drive one or more of the plurality of ultrasound transducer elements to deliver a plurality of sequential therapy bursts of ultrasonic energy to at least one of the one or more target points in the target region using coded excitation.

41. The system of claim 1, wherein control image data is generated based at least in part on imaging performed at least in part during delivery of one or more therapy bursts using coded excitation.

42. The method of claim 25, wherein therapy signals are generated for use in one or more non-thermal treatments, wherein the one or more non-thermal treatments comprise at least one of delivery of therapy to a target region in which a vessel of the patient is located, delivery of therapy to a target region in which a nerve is located, activation of a drug in a target region, and delivery of therapy to a target region in which a tumor is located.

43. The method of claim 25, wherein therapy signals are generated for use in one or more thermal treatments, wherein the one or more thermal treatments comprise at least one of delivery of therapy to a target region in which a blood vessel is located, delivery of therapy to a target region in which a tumor is located, delivery of therapy to a target region in which a nerve is located, activation of a drug in a target region, and delivery of therapy to a target region in which a vessel of the patient is located.

44. The method of claim 35, wherein the configurable diplexer further comprises a selectable voltage divider to attenuate a pulse echo signal received by the transducer element, and further wherein the method comprises controlling the selectable voltage divider to at least one of attenuate the pulse echo signal or leave the pulse echo signal at its current level.

45. The method of claim 25, wherein a control channel is associated with each of a plurality of ultrasound transducer elements of the array,
wherein a multichannel driver is configured to drive the plurality of ultrasound transducer elements with therapy signals and imaging signals, wherein the multichannel driver is configurable to store and control the therapy signals and imaging signals used to drive the plurality of ultrasound transducer elements,
wherein the multichannel driver comprises a plurality of buffers, wherein the plurality of buffers comprises:
at least a first buffer to provide storage of a therapy protocol of therapy signals to be delivered by the plurality of ultrasound transducer elements during a current time period for use in driving the plurality of ultrasound transducer elements via the respective control channels to deliver energy to at least one target point in the target region, wherein each of the plurality of ultrasound transducer elements is driven at one or more drive parameters to focus the ultrasound energy for delivery of each sequential therapy burst, the one or more drive parameters corresponding to at least one of the amplitude, the duration, and the spectral content defining each continuous therapy burst of the plurality of sequential therapy bursts; and
a second buffer to store a therapy protocol of therapy signals to be delivered in a next time period following the current time period; and
further wherein the method comprises:
generating control image data based on at least one of pulse echo data received via the respective control channels from one or more of the plurality of ultrasound transducer elements during delivery of each therapy burst of a plurality of sequential therapy bursts and pulse echo data received via the respective control channels from one or more of the plurality of ultrasound transducer elements following delivery of each therapy burst of a plurality of sequential therapy bursts to monitor tissue response in the target region; and
adjusting one or more of the drive parameters of one or more of the plurality of ultrasound transducer elements based on the control image data for storage by the second buffer of the therapy protocol comprising the adjusted drive parameters to be delivered in the next time period following the current time period for use in driving the plurality of ultrasound transducer elements via the respective control channels to deliver energy to at least one target point in the target region, wherein each of the plurality of ultrasound transducer elements is driven at the adjusted drive parameters to focus the ultrasound energy for delivery of the subsequent therapy burst, the adjusted drive parameters corresponding to at least one of the amplitude, the duration, and the spectral content defining the continuous therapy burst corresponding to the subsequent therapy burst of the plurality of sequential therapy bursts.

46. The method of claim 45, wherein the method includes managing the first and second buffers to provide a reconfigurable silencing period with a granularity of less than 1 microsecond, the reconfigurable silencing period being below the mechanical and thermal response time of the tissue.

47. The method of claim 25, wherein, in generating control image data to monitor tissue response in the target region to the delivery of the sequential therapy bursts in real-time, the control image data is generated based on at least one of pulse echo data received by one or more of the plurality of ultrasound transducer elements during delivery of each therapy burst of a plurality of sequential therapy bursts and pulse echo data received by one or more of the plurality of ultrasound transducer elements following delivery of each therapy burst of a plurality of sequential therapy bursts and before each next therapy burst.

* * * * *